(12) United States Patent
Church et al.

(10) Patent No.: US 12,343,436 B2
(45) Date of Patent: Jul. 1, 2025

(54) SYSTEM AND METHODS FOR IMPLEMENTING A BIOLOGICAL FLUID TREATMENT DEVICE

(71) Applicant: Cerus Corporation, Concord, CA (US)

(72) Inventors: Daniel Church, Danville, CA (US); Lloyd Ison, Livermore, CA (US); Seyhan Akkoyun, Concord, CA (US)

(73) Assignee: Cerus Corporation, Concord, CA (US)

( * ) Notice: Subject to any disclaimer, the term of this patent is extended or adjusted under 35 U.S.C. 154(b) by 37 days.

(21) Appl. No.: 18/536,905

(22) Filed: Dec. 12, 2023

(65) Prior Publication Data

US 2024/0108767 A1 Apr. 4, 2024

Related U.S. Application Data

(62) Division of application No. 16/914,229, filed on Jun. 26, 2020, now Pat. No. 11,883,544.

(60) Provisional application No. 62/868,859, filed on Jun. 28, 2019.

(51) Int. Cl.
| | | |
|---|---|---|
| *A61L 2/00* | (2006.01) | |
| *A61L 2/24* | (2006.01) | |
| *B01F 31/00* | (2022.01) | |
| *B01F 35/221* | (2022.01) | |

(Continued)

(52) U.S. Cl.
CPC ............... *A61L 2/007* (2013.01); *A61L 2/24* (2013.01); *B01F 31/00* (2022.01); *B01F 35/2214* (2022.01); *B01F 35/3204* (2022.01); *A61L 2202/11* (2013.01); *A61L 2202/14* (2013.01); *A61L 2202/22* (2013.01); *B01F 2101/23* (2022.01)

(58) Field of Classification Search
CPC ........ A61L 2/007; A61L 2/24; A61L 2202/11; A61L 2202/14; A61L 2202/22; B01F 31/00; B01F 35/2214; B01F 35/3204
See application file for complete search history.

(56) References Cited

U.S. PATENT DOCUMENTS

| | | | |
|---|---|---|---|
| 5,167,656 | A | 12/1992 | Lynn |
| 5,221,608 | A | 6/1993 | Cimino et al. |
| 5,288,605 | A | 2/1994 | Lin et al. |

(Continued)

FOREIGN PATENT DOCUMENTS

| | | |
|---|---|---|
| CN | 1284886 A | 2/2001 |
| CN | 1450916 A | 10/2003 |

(Continued)

OTHER PUBLICATIONS

International Preliminary Report on Patentability, issued Apr. 13, 2023 for PCT Application No. PCT/US2021/071920, filed Oct. 18, 2021, 7 pages.

(Continued)

*Primary Examiner* — Sean E Conley
(74) *Attorney, Agent, or Firm* — MORRISON & FOERSTER LLP

(57) ABSTRACT

Electronic devices for treating a biological fluid and methods of operating the devices are disclosed. In some embodiments, the electronic device includes a plurality of non-safety critical components, a first controller communicatively coupled to the plurality of non-safety critical components, a plurality of safety critical components, and a second controller communicatively coupled to the plurality of safety critical components. In some embodiments, the electronic device includes a treatment interface.

20 Claims, 17 Drawing Sheets

(51) Int. Cl.
*B01F 35/32* (2022.01)
*B01F 101/23* (2022.01)

(56) References Cited

U.S. PATENT DOCUMENTS

| | | |
|---|---|---|
| 5,399,719 A | 3/1995 | Wollowitz et al. |
| 5,405,343 A | 4/1995 | Mohr |
| 5,418,130 A | 5/1995 | Platz et al. |
| 5,459,030 A | 10/1995 | Lin et al. |
| 5,482,828 A | 1/1996 | Lin et al. |
| 5,556,958 A | 9/1996 | Carroll |
| 5,556,993 A | 9/1996 | Wollowitz |
| 5,559,250 A | 9/1996 | Cook |
| 5,571,082 A | 11/1996 | Bashikirov |
| 5,578,736 A | 11/1996 | Wollowitz |
| 5,585,503 A | 12/1996 | Wollowitz |
| 5,589,462 A | 12/1996 | Patat |
| 5,593,823 A | 1/1997 | Wollowitz et al. |
| 5,618,662 A | 4/1997 | Lin et al. |
| 5,625,079 A | 4/1997 | Wollowitz et al. |
| 5,654,443 A | 8/1997 | Wollowitz |
| 5,691,132 A | 11/1997 | Wollowitz et al. |
| 5,709,991 A | 1/1998 | Lin et al. |
| 5,712,085 A | 1/1998 | Wollowitz |
| 5,871,900 A | 2/1999 | Wollowitz |
| 5,908,742 A | 6/1999 | Lin et al. |
| 5,965,349 A | 10/1999 | Lin |
| 5,972,593 A | 10/1999 | Wollowitz |
| 6,004,741 A | 12/1999 | Wollowitz |
| 6,004,742 A | 12/1999 | Wollowitz |
| 6,017,691 A | 1/2000 | Wollowitz et al. |
| 6,093,725 A | 7/2000 | Cook et al. |
| 6,133,460 A | 10/2000 | Wollowitz et al. |
| 6,143,490 A | 11/2000 | Cook et al. |
| 6,171,777 B1 | 1/2001 | Cook |
| 6,177,441 B1 | 1/2001 | Cook et al. |
| 6,194,139 B1 | 2/2001 | Wollowitz |
| 6,218,100 B1 | 4/2001 | Wollowitz |
| 6,251,580 B1 | 6/2001 | Lin |
| 6,270,952 B1 | 8/2001 | Cook et al. |
| 6,277,337 B1 | 8/2001 | Goodrich, Jr. et al. |
| 6,281,225 B1 | 8/2001 | Hearst et al. |
| 6,410,219 B1 | 6/2002 | Cook et al. |
| 6,420,570 B1 | 7/2002 | Wollowitz |
| 6,433,343 B1 | 8/2002 | Cimino et al. |
| 6,455,286 B1 | 9/2002 | Wollowitz |
| 6,469,052 B2 | 10/2002 | Wollowitz |
| 6,503,699 B1 | 1/2003 | Wollowitz et al. |
| 6,514,987 B1 | 2/2003 | Cook et al. |
| 6,544,727 B1 | 4/2003 | Hei |
| 6,548,242 B2 | 4/2003 | Horowitz et al. |
| 6,565,802 B1 | 5/2003 | Hanley |
| 6,586,749 B2 | 7/2003 | Cimino |
| 6,686,480 B2 | 2/2004 | Wollowitz |
| 6,709,810 B2 | 3/2004 | Cook |
| 6,843,961 B2 | 1/2005 | Hlavinka et al. |
| 6,949,753 B2 | 9/2005 | Cimino |
| 6,951,713 B2 | 10/2005 | Hei et al. |
| 6,986,867 B2 | 1/2006 | Hanley et al. |
| 7,025,877 B1 | 4/2006 | De |
| 7,037,642 B2 | 5/2006 | Hei et al. |
| 7,105,093 B2 | 9/2006 | De |
| 7,293,985 B2 | 11/2007 | Cook |
| 7,425,304 B2 | 9/2008 | De |
| 7,433,030 B2 | 10/2008 | Waldo et al. |
| 7,459,695 B2 | 12/2008 | Hanley et al. |
| 7,601,298 B2 | 10/2009 | Waldo et al. |
| 7,611,831 B2 | 11/2009 | Hei |
| 7,655,392 B2 | 2/2010 | Stassinopoulos |
| 7,788,038 B2 | 8/2010 | Oshita |
| 7,829,867 B2 | 11/2010 | Hlavinka et al. |
| 8,296,071 B2 | 10/2012 | Edrich et al. |
| 8,492,162 B2 | 7/2013 | Kippenhan |
| 8,778,263 B2 | 7/2014 | Walker et al. |
| 8,900,805 B2 | 12/2014 | Mufti et al. |
| 9,259,525 B2 | 2/2016 | Hei |
| 9,320,817 B2 | 4/2016 | Walker et al. |
| 9,713,627 B2 | 7/2017 | Mufti |
| 10,004,821 B2 | 6/2018 | Dobrinsky |
| 10,357,516 B2 | 7/2019 | Mufti |
| 10,506,915 B2 | 12/2019 | Iwasaki |
| 10,758,868 B2 | 9/2020 | Fulkerson |
| 10,799,533 B2 | 10/2020 | Corash |
| 10,842,818 B2 | 11/2020 | Vermeij |
| 11,096,963 B2 | 8/2021 | Corash et al. |
| 11,554,185 B2 | 1/2023 | Church et al. |
| 11,660,365 B2 | 5/2023 | Thompson |
| 11,883,544 B2 | 1/2024 | Church |
| 2001/0009756 A1 | 7/2001 | Hei |
| 2001/0018179 A1 | 8/2001 | Hei |
| 2002/0006393 A1 | 1/2002 | Wollowitz |
| 2002/0028432 A1 | 3/2002 | Cook |
| 2002/0042043 A1 | 4/2002 | Stassinopoulos |
| 2002/0115585 A1 | 8/2002 | Hei |
| 2002/0192632 A1 | 12/2002 | Hei |
| 2003/0035751 A1 | 2/2003 | Hanley et al. |
| 2003/0062483 A1 | 4/2003 | Cimino |
| 2003/0105339 A1 | 6/2003 | Wollowitz |
| 2003/0113704 A1 | 6/2003 | Stassinopoulos |
| 2003/0146162 A1 | 8/2003 | Metzel et al. |
| 2003/0185804 A1 | 10/2003 | Wollowitz et al. |
| 2003/0207247 A1 | 11/2003 | Stassinopoulos et al. |
| 2003/0219354 A1 | 11/2003 | Hlavinka et al. |
| 2004/0021809 A1 | 2/2004 | Sumiyoshi et al. |
| 2004/0029897 A1 | 2/2004 | Cook |
| 2004/0088189 A1 | 5/2004 | Veome et al. |
| 2004/0172007 A1 | 9/2004 | Grimm et al. |
| 2004/0180321 A1 | 9/2004 | Cook |
| 2004/0185544 A9 | 9/2004 | Hei |
| 2004/0185553 A9 | 9/2004 | Hei |
| 2004/0197343 A1 | 10/2004 | Dubensky et al. |
| 2004/0228877 A1 | 11/2004 | Dubensky et al. |
| 2005/0142542 A1 | 6/2005 | Hei |
| 2005/0175625 A1 | 8/2005 | Jaffee et al. |
| 2005/0202395 A1 | 9/2005 | Edrich et al. |
| 2005/0249748 A1 | 11/2005 | Dubensky et al. |
| 2005/0281783 A1 | 12/2005 | Kinch et al. |
| 2006/0093999 A1 | 5/2006 | Hei |
| 2006/0115466 A1 | 6/2006 | Stassinopoulos |
| 2006/0197031 A1 | 9/2006 | De et al. |
| 2006/0221329 A1 | 10/2006 | Waldo et al. |
| 2007/0031457 A1 | 2/2007 | Dubensky et al. |
| 2007/0190029 A1 | 8/2007 | Pardoll et al. |
| 2007/0190063 A1 | 8/2007 | Bahjat et al. |
| 2007/0207170 A1 | 9/2007 | Dubensky et al. |
| 2007/0207171 A1 | 9/2007 | Dubensky et al. |
| 2007/0235376 A1 | 10/2007 | Daniel |
| 2009/0250626 A1 | 10/2009 | Schlesser et al. |
| 2010/0133160 A1 | 6/2010 | Hei |
| 2011/0286987 A1 | 11/2011 | Mufti |
| 2012/0070339 A1 | 3/2012 | Lawal |
| 2012/0153783 A1 | 6/2012 | Shoenfeld |
| 2012/0313014 A1 | 12/2012 | Stibich et al. |
| 2013/0320299 A1 | 12/2013 | Li |
| 2013/0323128 A1 | 12/2013 | Owen et al. |
| 2014/0303547 A1 | 10/2014 | Loupis et al. |
| 2014/0346370 A1 | 11/2014 | Dobrinsky et al. |
| 2014/0353519 A1 | 12/2014 | Wang |
| 2015/0157665 A1 | 6/2015 | Mufti |
| 2015/0299000 A1 | 10/2015 | Smith et al. |
| 2016/0354533 A1 | 12/2016 | Hei |
| 2017/0014538 A1 | 1/2017 | Rantala |
| 2017/0027986 A1 | 2/2017 | Corash et al. |
| 2017/0028121 A1 | 2/2017 | Manzella et al. |
| 2017/0050046 A1 | 2/2017 | Walder et al. |
| 2017/0054687 A1 | 2/2017 | Ishigaki |
| 2017/0202882 A1 | 7/2017 | Vermeij |
| 2017/0252474 A1 | 9/2017 | Thompson et al. |
| 2017/0304363 A1 | 10/2017 | Corash |
| 2018/0008639 A1 | 1/2018 | Mufti |
| 2018/0113066 A1 | 4/2018 | Freitag et al. |
| 2018/0147306 A1 | 5/2018 | Crawley et al. |
| 2018/0184985 A1 | 7/2018 | Håkansson et al. |
| 2018/0185484 A1 | 7/2018 | Greenman et al. |

(56) References Cited

U.S. PATENT DOCUMENTS

| | | |
|---|---|---|
| 2018/0193500 A1 | 7/2018 | Safavi et al. |
| 2018/0289873 A1 | 10/2018 | David |
| 2018/0318348 A1 | 11/2018 | Corash et al. |
| 2018/0369437 A1 | 12/2018 | Grossman et al. |
| 2019/0085289 A1 | 3/2019 | Greenman |
| 2019/0099543 A1 | 4/2019 | Sasaki |
| 2019/0100718 A1 | 4/2019 | Estes et al. |
| 2019/0209718 A1 | 7/2019 | Church |
| 2019/0321407 A1 | 10/2019 | Erickson et al. |
| 2019/0369087 A1 | 12/2019 | North et al. |
| 2020/0063179 A1 | 2/2020 | Eghbal |
| 2020/0078406 A1 | 3/2020 | Weiner et al. |
| 2020/0397931 A1 | 12/2020 | Church et al. |
| 2020/0397935 A1 | 12/2020 | Church et al. |
| 2020/0405891 A1 | 12/2020 | Church et al. |
| 2021/0038802 A1 | 2/2021 | Madsen |
| 2021/0052804 A1 | 2/2021 | Madsen |
| 2021/0187020 A1 | 6/2021 | Corash et al. |
| 2021/0260114 A1 | 8/2021 | Corash et al. |
| 2021/0322479 A1 | 10/2021 | Vermeij |
| 2022/0031917 A1 | 2/2022 | Cahyadi et al. |
| 2022/0118136 A1 | 4/2022 | Church et al. |
| 2023/0226232 A1 | 7/2023 | Church et al. |
| 2024/0108767 A1 | 4/2024 | Church |

FOREIGN PATENT DOCUMENTS

| | | |
|---|---|---|
| CN | 203017432 U | 6/2013 |
| CN | 105412960 A | 3/2016 |
| CN | 106421864 A | 2/2017 |
| CN | 107075478 A | 8/2017 |
| CN | 107852359 A | 3/2018 |
| EP | 1181061 B1 | 8/2006 |
| EP | 3009946 A1 | 4/2016 |
| JP | 2006501978 A | 1/2006 |
| JP | 2006505349 A | 2/2006 |
| JP | 2011036683 A | 2/2011 |
| JP | 2015042266 A | 3/2015 |
| JP | 2015171440 A | 10/2015 |
| JP | 2017029717 A | 2/2017 |
| JP | 2017077247 A | 4/2017 |
| JP | 2017153966 A | 9/2017 |
| JP | 2017184725 A | 10/2017 |
| WO | 199300005 A1 | 1/1993 |
| WO | 199317553 A1 | 9/1993 |
| WO | 199403054 A1 | 2/1994 |
| WO | 199420090 A1 | 9/1994 |
| WO | 199427433 A1 | 12/1994 |
| WO | 199428120 A1 | 12/1994 |
| WO | 199500141 A1 | 1/1995 |
| WO | 199512973 A1 | 5/1995 |
| WO | 199519705 A1 | 7/1995 |
| WO | 199608965 A1 | 3/1996 |
| WO | 199614737 A1 | 5/1996 |
| WO | 199614739 A1 | 5/1996 |
| WO | 199614740 A1 | 5/1996 |
| WO | 199639815 A1 | 12/1996 |
| WO | 199639818 A1 | 12/1996 |
| WO | 199639820 A1 | 12/1996 |
| WO | 199640857 A1 | 12/1996 |
| WO | 199721346 A1 | 6/1997 |
| WO | 199737536 A1 | 10/1997 |
| WO | 199818908 A1 | 5/1998 |
| WO | 199830327 A1 | 7/1998 |
| WO | 199830545 A1 | 7/1998 |
| WO | 199903976 A2 | 1/1999 |
| WO | 199903976 A3 | 5/1999 |
| WO | 199926476 A1 | 6/1999 |
| WO | 199934839 A1 | 7/1999 |
| WO | 199934914 A1 | 7/1999 |
| WO | 199934915 A1 | 7/1999 |
| WO | 199959645 A1 | 11/1999 |
| WO | 199963981 A2 | 12/1999 |
| WO | 199963981 A3 | 4/2000 |
| WO | 200074731 A1 | 12/2000 |
| WO | 200191775 A2 | 12/2001 |
| WO | 200191775 A3 | 6/2002 |
| WO | 02053209 A1 | 7/2002 |
| WO | 2003047650 A2 | 6/2003 |
| WO | 2003049784 A2 | 6/2003 |
| WO | 2003049784 A3 | 6/2003 |
| WO | 2003061379 A2 | 7/2003 |
| WO | 2003065787 A2 | 8/2003 |
| WO | 2003078023 A1 | 9/2003 |
| WO | 2003061379 A3 | 10/2003 |
| WO | 2003090794 A1 | 11/2003 |
| WO | 2003065787 A3 | 12/2003 |
| WO | 2003047650 A3 | 2/2004 |
| WO | 2004018471 A1 | 3/2004 |
| WO | 2004033081 A2 | 4/2004 |
| WO | 2004044810 A1 | 5/2004 |
| WO | 2004033081 A3 | 6/2004 |
| WO | 2004049914 A2 | 6/2004 |
| WO | 2004050029 A2 | 6/2004 |
| WO | 2004050848 A2 | 6/2004 |
| WO | 2004050897 A2 | 6/2004 |
| WO | 2004050897 A3 | 8/2004 |
| WO | 2004050029 A3 | 10/2004 |
| WO | 2004084936 A2 | 10/2004 |
| WO | 2004050848 A3 | 12/2004 |
| WO | 2004110481 A2 | 12/2004 |
| WO | 2004049914 A3 | 2/2005 |
| WO | 2005009463 A2 | 2/2005 |
| WO | 2004110481 A3 | 3/2005 |
| WO | 2005037233 A2 | 4/2005 |
| WO | 2004084936 A3 | 6/2005 |
| WO | 2005009463 A3 | 6/2005 |
| WO | 2005067460 A2 | 7/2005 |
| WO | 2005071088 A2 | 8/2005 |
| WO | 2005092372 A2 | 10/2005 |
| WO | 2005071088 A3 | 11/2005 |
| WO | 2005037233 A3 | 1/2006 |
| WO | 2006021314 A2 | 3/2006 |
| WO | 2006050328 A1 | 5/2006 |
| WO | 2005092372 A3 | 6/2006 |
| WO | 2005067460 A3 | 10/2006 |
| WO | 2007022511 A2 | 2/2007 |
| WO | 2007022520 A2 | 2/2007 |
| WO | 2007022520 A3 | 5/2007 |
| WO | 2007022511 A3 | 9/2007 |
| WO | 2007103225 A2 | 9/2007 |
| WO | 2007103261 A2 | 9/2007 |
| WO | 2007103225 A3 | 5/2008 |
| WO | 2007103261 A3 | 12/2008 |
| WO | 2008156813 A1 | 12/2008 |
| WO | 2009126786 A2 | 10/2009 |
| WO | 2009126786 A3 | 7/2010 |
| WO | 2011120172 A1 | 10/2011 |
| WO | 2012018484 A2 | 2/2012 |
| WO | 2012018484 A3 | 4/2012 |
| WO | 2012071135 A2 | 5/2012 |
| WO | 2012071135 A3 | 8/2012 |
| WO | 2014022717 A1 | 2/2014 |
| WO | 2014051882 A1 | 4/2014 |
| WO | 2014051906 A1 | 4/2014 |
| WO | 2015168783 A1 | 11/2015 |
| WO | 2016014854 A1 | 1/2016 |
| WO | 2016057965 A1 | 4/2016 |
| WO | 2016115535 A1 | 7/2016 |
| WO | 2016149055 A2 | 9/2016 |
| WO | 2016149055 A3 | 12/2016 |
| WO | 2016210374 A1 | 12/2016 |
| WO | 2017009534 A1 | 1/2017 |
| WO | 2017047119 A1 | 3/2017 |
| WO | 2017062260 A2 | 4/2017 |
| WO | 2017070619 A1 | 4/2017 |
| WO | 2017062260 A3 | 5/2017 |
| WO | 2017120545 A2 | 7/2017 |
| WO | 2017120545 A3 | 8/2017 |
| WO | 2018119462 A1 | 6/2018 |
| WO | 2018125994 A1 | 7/2018 |
| WO | 2018161020 A1 | 9/2018 |
| WO | 2019060610 A1 | 3/2019 |
| WO | 2019133929 A1 | 7/2019 |

(56) References Cited

FOREIGN PATENT DOCUMENTS

| WO | 2020061537 A1 | 3/2020 |
|---|---|---|
| WO | 2020263745 A1 | 12/2020 |
| WO | 2020263759 A2 | 12/2020 |
| WO | 2020263759 A3 | 1/2021 |
| WO | 2022087580 A1 | 4/2022 |

OTHER PUBLICATIONS

Alhumaidan, H. et al. (2012). "Current Status of Additive Solution for Platelets," J. Clin Apheresis 27:93-98.

Anonymous (2018). "DS9900 Series Corded Hybrid Imager for Labs," ZEBRA, 4 pages.

International Preliminary Report on Patentability, issued Dec. 28, 2021, for PCT Application No. PCT/US2020/038950, filed Jun. 22, 2020, 9 pages.

International Preliminary Report on Patentability, issued Dec. 28, 2021, for PCT Application No. PCT/US2020/039011, filed Jun. 22, 2020, 13 pages.

International Preliminary Report on Patentability, issued Dec. 28, 2021, for PCT Application No. PCT/US2020/039984, filed Jun. 26, 2020, 8 pages.

International Preliminary Report on Patentability, issued Jun. 30, 2020, for PCT Application No. PCT/US2018/068048, 11 pages.

International Search Report and Written Opinion, mailed Aug. 19, 2002, for PCT Application No. PCT/US2020/038950, filed Jun. 22, 2020, 16 pages.

International Search Report and Written Opinion, mailed Dec. 23, 2020, for PCT Application No. PCT/US2020/039011, filed Jun. 22, 2020, 18 pages.

International Search Report and Written Opinion, mailed Jan. 17, 2022, for PCT Application No. PCT/US2021/0071920, filed Oct. 18, 2021, 14 pages.

International Search Report and Written Opinion, mailed May 3, 2019, for PCT Application No. PCT/US2018/068048, filed on Dec. 28, 2018 18 pages.

International Search Report and Written Opinion, mailed Sep. 29, 2020, for PCT Application No. PCT/US2020/039984, filed Jun. 26, 2020, 14 pages.

Irsch, J. et al. (2011, e-pub. Jan. 27, 2011). "Pathogen Inactivation of Platelet and Plasma Blood Components for Transfusion Using the Intercept Blood System™," Transfus. Med. Hemother. 38:19-31.

Oxford English Dictionary (Date Unknown). "System," located at https://www.oed.com/search/dictionary/?scope=Entries&q=system &tl=true, last visited on Sep. 26, 2023, one page.

Prodouz, K.N. et al. (1992). "Effects of Two Viral Inactivation Methods on Platelets: Laser-UV Radiation and Merocyanie 540-Mediated Photoinactivation," Blood Cells 18(1): 101-116.

Prowse, C.V. (Apr. 2013, e-pub. Nov. 8, 2012). "Component Pathogen Inactivation: A Critical Review," Vox Sanguinis, 104(3): 183-199.

Reikvam, H. et al. (2010). "The Mirasol® Pathogen Reduction Technology System and Quality of Platelets Stored in Platelet Additive Solution," Blood Transfus. 8:186-192.

Ringwald, J. et al. (Apr. 2006). "The New Generation of Platelet Additivie Solution for Storage at 22: Development and Current Experience," Transfusion Medicine Reviews, 20(2):158-164.

Schlenke, P. (2014, e-pub. Jul. 21, 2014). "Pathogen Inactivation Technologies for Cellular Blood Components: an Update," Transfus. Med. Hemother. 41:309-325.

Schlenke, P. et al. (2008). "Photochemical Treatment Of Plasma With Amotosalen and UVA Light: Process Validation In Three European Blood Centers," Transfusion 48:697-705, 9 pages.

Seltsam, A. et al. (2011, e-pub. Jan. 22, 2011). "UVC Irradiation For Pathogen Reduction of Platelet Concentrates and Plasma," Transfusion Medicine and Hemotherapy 38:43-54.

Sofer, G. (Aug. 2002). "Virus Inactivation In The 1990s—and Into the 21st Century: Part 2, Red Blood Cells and Platelets," BioPharm pp. 42-49.

U.S. Appl. No. 09/238,355, Greenman, W. et al., filed on Jan. 27, 1999. (waiver of 37 C.F.R. § 1.98(a)(2)(iii) issued by the Office on Sep. 21, 2004.).

U.S. Appl. No. 17/277,680, Cahyadi, H. et al., filed on Mar. 18, 2021. (waiver of 37 C.F.R. § 1.98(a)(2)(iii) issued by the Office on Sep. 21, 2004.).

U.S. Appl. No. 17/451,311, Church, D. et al., filed on Oct. 18, 2021. (waiver of 37 C.F.R. § 1.98(a)(2)(iii) issued by the Office on Sep. 21, 2004.).

SYSTEM AND METHODS FOR IMPLEMENTING A BIOLOGICAL FLUID TREATMENT DEVICE

CROSS REFERENCE TO RELATED APPLICATIONS

This application is a divisional of U.S. Ser. No. 16/914,229, filed on Jun. 26, 2020, which claims the priority benefit of U.S. Provisional Application No. 62/868,859, filed on Jun. 28, 2019, the contents of which are incorporated herein by reference in their entirety.

FIELD OF THE DISCLOSURE

This disclosure relates generally to systems, methods, and devices for treating biological fluids, including mixtures of biological fluids and photochemical agents, with light, and more specifically to a system architecture for implementing and coordinating various systems and sub-systems of a biological fluid treatment device.

BACKGROUND OF THE DISCLOSURE

Systems and methods for treating biological fluids with light are well known. For example, U.S. Pat. Nos. 7,459,695, 6,986,867, and 5,593,823 describe a system for treating a biological fluid with light to inactivate pathogens in the biological fluid. Light is emitted within a selected range of wavelengths that are effective to inactivate pathogens in the biological fluid, particularly by photochemical inactivation of pathogens. Other systems and methods for treating biological fluids with light may include, for example, systems and methods described in U.S. Pat. Nos. 6,843,961, 7,829,867, 9,320,817 and 8,778,263, and Schlenke, 2014, Transfus. Med. Hemother. 41:309-325.

For blood products including for example, platelets and plasma components and their derivatives, it is important to ensure that the blood products are free of pathogens to minimize the risk of infecting an individual receiving a blood product. Testing for the presence of a pathogen in blood is limited by the pathogens for which tests are available and assay sensitivity. As an alternative or supplement to testing for pathogens, methods are known in the art for inactivating pathogens using various compound (e.g., chemical, photochemical)-based inactivation methods to reduce the risk of transfusion-transmitted infection (e.g., as disclosed in Schlenke et al., Transfus Med Hemother, 2014, 41, 309-325 and Prowse, Vox Sanguinis, 2013, 104, 183-199). Photochemical pathogen inactivation systems based on psoralens and ultraviolet light for treating blood products include the commercially available INTERCEPT® Blood System (Cerus Corporation), which utilizes disposable processing sets and an ultraviolet illumination device (INT-100). Blood products such as plasma or platelets are mixed with a psoralen, amotosalen, in the processing sets and then illuminated with ultraviolet A light. Multiple different disposable processing sets may be used, depending on the type of blood product to be treated and particular properties of those blood products, such as for example volume and platelet number.

Electronic devices that are configured to treat biological fluids can often include a diverse set of systems and sub-systems that are required to work in coordination with one another to treat a biological fluid. For example, an electronic device that is configured to illuminate (e.g., irradiate) a biological fluid (e.g., with or without a pathogen inactivation compound) to inactivate potential pathogens in the fluid can include a plurality of systems such as a lighting system, an agitator, a safety system, etc. These various systems must work together to ensure proper application of the treatment to the biological fluid.

While previous systems and methods for treating biological fluids, such as blood products including for example, platelets and plasma and derivatives thereof, have generally performed satisfactorily, due to the high level of coordination that may be required of the components within a device, the process of treating the fluid may be inefficient and costly from a computing and hardware resource perspective. Furthermore, the system architectures of these device may not be ideal for changes made to the device. For instance if a safety critical or non-safety critical component of the device is replaced or modified, such as for example due to improvements or obsolescence, or if one or more additional safety critical or non-safety critical components are added to the device, the change may have a significant impact on other components within the device. This impact may include regulatory approvals or standards that such components, and the overall device, are required to maintain in order for the device to be approved for commercial use.

Furthermore, the device may include components that are externally accessible (i.e., via a connection to an external computing network) which can make them vulnerable to hacking or intrusion. Since the device contains many safety critical components, if a malicious user were able to exploit the devices external accessibility to gain control of the device, they could endanger the safety and efficacy of the treatment protocols the device performs.

In light of the high-level coordination between complex systems that can be necessary when operating a biological fluid treatment device, there can be a need for a system and method of implementing a biological fluid treatment device that maximizes the coordination of various systems of the device while minimizing the cost, inefficiency, and/or security risk associated with operating such a device.

SUMMARY OF THE DISCLOSURE

Disclosed here in are electronic devices for treating a biological fluid and methods of operating the devices are disclosed. Some examples of the disclosure are directed to an electronic device, wherein the electronic device includes a plurality of components collectively configured to treat one or more biological fluids, the device comprising: a first group of components, wherein the first group of components includes one or more components configured to receive one or more inputs from a user of the device, a first controller communicatively coupled to the first group of components and configured to operate the first group of components using one or more commands formatted using a first communications protocol, a second group of components, wherein the second group of components comprise: one or more platforms, wherein each platform of the one or more platforms is configured to carry a biological fluid of the one or more biological fluids, one or more light engines, wherein each light engine is configured to illuminate a biological fluid of the one or more biological fluids; and a second controller communicatively coupled to the second group of components and communicatively coupled to the first controller, wherein the second controller is configured to coordinate one or more operations involving the second group of components, wherein the second controller communicates with the first controller and the second group of components using a second communications protocol, wherein the second communications protocol is configured such that the second group of components operate in response to one or commands from the second controller using the second communications protocol.

Additionally or alternatively to one or more examples disclosed above the second group of components are configured to operate only in response to one or more commands transmitted from the second controller using the second communications protocol. Additionally or alternatively to one or more examples disclosed above a message transmitted in the second communications protocol includes information about the component that generated the message. Additionally or alternatively to one or more examples disclosed above the first group of components include one or more components configured to allow an external user to interface with the device. Additionally or alternatively to one or more examples disclosed above the first group of components includes a display configured to provide visual cues to the user of the device and configured to accept one or more inputs. Additionally or alternatively to one or more examples disclosed above the wherein the device is configured to accept one or more inputs from a component of the device, including a scanner and sensor. Additionally or alternatively to one or more examples disclosed above the display is a touchscreen display configured to accept one or more touch inputs from the user of the device. Additionally or alternatively to one or more examples disclosed above the first group of components includes a scanner configured to collect identifying information associated with a biological fluid being treated. Additionally or alternatively to one or more examples disclosed above the scanner is configured to collect the identifying information in a visible form (e.g., barcode, Q-code, etc.) or in the form of a radio wave (e.g., RFID) associated with the biological fluid (e.g., on a container associated with the container.) Additionally or alternatively to one or more examples disclosed above the second group of components further includes one or more agitators, wherein each agitator is configured to agitate a biological fluid of the one or more biological fluids so as to distribute the biological fluid within a container that is disposed on a platform of the one or more platforms of the device. Additionally or alternatively to one or more examples disclosed above the device further comprises one or more treatment chambers configured to receive a biological fluid of the one or more biological fluids, and wherein each platform of the one or more platforms are configured to be positioned in a treatment chamber of the one or more treatment chambers. Additionally or alternatively to one or more examples disclosed above the second group of components further comprise one or more sensors configured to detect an operating condition of the device or a property of the biological fluid. Additionally or alternatively to one or more examples disclosed above the one or more light engines includes one or more arrays of light sources positioned to illuminate the biological fluid and wherein the one or more arrays of light sources are configured to emit light in an ultraviolet light spectrum. Additionally or alternatively to one or more examples disclosed above the one or more arrays of light sources each comprise a first light source channel configured to emit ultraviolet light with a first peak wavelength from about 315 nm to about 350 nm. Additionally or alternatively to one or more examples disclosed above the first light source channel comprises one or light sources, and each of which emits light having a full-width half-maximum (FWHM) spectral bandwidth of less than 20 nanometers. Additionally or alternatively to one or more examples disclosed above the one or more arrays of light sources comprise one or more light sources each of which emits light having a full-width half-maximum (FWHM) spectral bandwidth of less than 20 nanometers. Additionally or alternatively to one or more examples disclosed above the first light source channel comprises one or more light sources, and wherein the one or more light sources are light emitting diodes (LEDs). Additionally or alternatively to one or more examples disclosed above the one or more arrays of light sources comprise one or more light sources, and wherein the one or more light sources are light emitting diodes (LEDs). Additionally or alternatively to one or more examples disclosed above the one or more light engines further comprise one or more sensors configured to detect light energy from the one or more arrays of light sources. Additionally or alternatively to one or more examples disclosed above the second controller is configured to turn one or more of the second group of components on or off based on one or more signals transmitted by the one or more sensors. Additionally or alternatively to one or more examples disclosed above, the device further comprises: a first treatment chamber configured to receive a first biological fluid, a second treatment chamber configured to receive a second biological fluid: a first platform configured to carry the first biological fluid and to be positioned in the first treatment chamber, a second platform configured to carry the second biological fluid and to be positioned in the second treatment chamber, and a first array of light sources positioned to illuminate the first biological fluid in the first treatment chamber and a second array of light sources positioned to illuminate the second biological fluid in the second treatment chamber. Additionally or alternatively to one or more examples disclosed above the device is further configured to receive one or more inputs from a user of the device, and the device is configured to: transmit one or more commands using the first communications protocol to the first controller, wherein the one or more commands are configured to initiate a treatment process on a biological fluid of the one or more biological fluids, at the first controller, convert the one or more commands in the first communications protocol into one or more commands in the second communications protocol and transmit the one or more commands in the second communications protocol to the second controller, and at the second controller, convert the received one or more commands in the second communications protocol into one or more commands to control one or more components of the second group of components and transmit the one or more commands to the one or more components of the second group of components, wherein the one or more commands to control the one or more components of the second group of components are configured to cause the device to treat a biological fluid of the one or more biological fluids. Additionally or alternatively to one or more examples disclosed above wherein treating the one or more biological fluids comprises illuminating the biological fluids for a duration and at an intensity sufficient to inactivate a pathogen in the biological fluids.

Some examples of the disclosure are directed to a method for treating one or more biological fluids at an electronic device, the method comprising: receiving one or more inputs from a user of the device, transmitting one or more commands using a first communications protocol to a first controller of the device, wherein the one or more commands are configured to initiate a treatment process on biological fluid of the one or more biological fluids, and wherein the first controller is communicatively coupled to a first group of components device and configured to operate the first group of components using one or more commands formatted using the first communications protocol, at the first controller, converting the one or more commands in the first communications protocol into one or more commands in a second communications protocol and transmitting the one or more commands in the second communications protocol to a second controller of the device, and at the second controller, converting the received one or more commands in the second communications protocol into one or more commands to control one or more components of a second group of components of the device and transmitting the one or more commands to one or more components of the second group of components, wherein the one or more commands to control the one or more components of the second group of components are configured to cause the device to treat a biological fluid of the one or more biological fluids.

Additionally or alternatively to one or more examples disclosed above the second group of components comprise: one or more platforms, wherein each platform of the one or more platforms is configured to carry a biological fluid of the one or more biological fluids; and one or more light engines, wherein each light engine is configured to illuminate a biological fluid of the one or more biological fluids. Additionally or alternatively to one or more examples disclosed above the second group of components are configured to operate only in response to one or more commands transmitted from the second controller using the second communications protocol. Additionally or alternatively to one or more examples disclosed above a message transmitted in the second communications protocol includes information about the component that generated the message. Additionally or alternatively to one or more examples disclosed above, the first group of components include one or more components configured to allow an external user to interface with the device. Additionally or alternatively to one or more examples disclosed above, the first group of components includes a display configured to provide visual cues to the user of the device and configured to accept one or more inputs. Additionally or alternatively to one or more examples disclosed above the display is a touchscreen display configured to accept one or more touch inputs from the user of the device. Additionally or alternatively to one or more examples disclosed above, the first group of components includes a scanner configured to collect identifying information associated with a biological fluid being treated. Additionally or alternatively to one or more examples disclosed above, the second group of components further includes one or more agitators, wherein each agitator is configured to agitate a biological fluid of the one or more biological fluids so as to distribute the biological fluid within a container that is disposed on a platform of the one or more platforms of the device. Additionally or alternatively to one or more examples disclosed above, the electronic device comprises one or more treatment chambers configured to receive a biological fluid of the one or more biological fluids, and wherein each platform of the one or more platforms are configured to be positioned in a treatment chamber of the one or more treatment chambers. Additionally or alternatively to one or more examples disclosed above the second group of components further comprise one or more sensors configured to an operating condition of the device or a property of the biological fluid. Additionally or alternatively to one or more examples disclosed above the one or more light engines includes one or more arrays of light sources positioned to illuminate a biological fluid of the one or more biological fluids and wherein the one or more arrays of light sources are configured to emit light in an ultraviolet light spectrum. Additionally or alternatively to one or more examples disclosed above the one or more arrays of light sources each comprise a first light source channel configured to emit ultraviolet light with a first peak wavelength from about 315 nm to about 350 nm. Additionally or alternatively to one or more examples disclosed above the first light source channel comprises one or light sources, and each of which emits light having a full-width half-maximum (FWHM) spectral bandwidth of less than 20 nanometers. Additionally or alternatively to one or more examples disclosed above the one or more arrays of light sources comprise one or more light sources each of which emits light having a full-width half-maximum (FWHM) spectral bandwidth of less than 20 nanometers. Additionally or alternatively to one or more examples disclosed above the first light source channel comprises one or more light sources, and wherein the one or more light sources are light emitting diodes (LEDs). Additionally or alternatively to one or more examples disclosed above the one or more arrays of light sources comprise one or more light sources, and wherein the one or more light sources are light emitting diodes (LEDs). Additionally or alternatively to one or more examples disclosed above the one or more light engines further comprise one or more sensors configured to detect light energy from the one or more arrays of light sources. Additionally or alternatively to one or more examples disclosed above the second controller is configured to turn one or more of the second group of components on or off based on one or more signals transmitted by the one or more sensors. Additionally or alternatively to one or more examples disclosed above, the device further comprises: a first treatment chamber configured to receive a first biological fluid, a second treatment chamber configured to receive a second biological fluid: a first platform configured to carry the first biological fluid and to be positioned in the first treatment chamber, a second platform configured to carry the second biological fluid and to be positioned in the second treatment chamber, and a first array of light sources positioned to illuminate the first biological fluid in the first treatment chamber and a second array of light sources positioned to illuminate the second biological fluid in the second treatment chamber. Additionally or alternatively to one or more examples disclosed above the device is further configured to receive one or more inputs from a user of the device, and the device is configured to: transmit one or more commands using the first communications protocol to the first controller, wherein the one or more commands are configured to initiate a treatment process on a biological fluid of the one or more biological fluids, at the first controller, convert the one or more commands in the first communications protocol into one or more commands in the second communications protocol and transmit the one or more commands in the second communications protocol to the second controller, and at the second controller, convert the received one or more commands in the second communications protocol into one or more commands to control one or more components of the second group of components and transmit the one or more commands to the one or more components of the second group of components, wherein the one or more commands to control the one or more components of the second group of components are configured to cause the device to treat a biological fluid of the one or more biological fluids. Additionally or alternatively to one or more examples disclosed above wherein treating the one or more biological fluids comprises illuminating the biological fluids for a duration and at an intensity sufficient to inactivate a pathogen in the biological fluids.

Some examples of the disclosure are directed to a computer readable storage medium storing one or more programs, the one or more programs comprising instructions, which when executed by an electronic device configured to treat one or more biological fluids, cause the device to: receive one or more inputs from a user of the device, transmit one or more commands using a first communications protocol to a first controller of the device, wherein the one or more commands are configured to initiate a treatment process on a biological fluid of the one or more biological fluids, and wherein the first controller is communicatively coupled to a first group of components device and configured to operate the first group of components using one or more commands formatted using the first communications protocol, at the first controller, convert the one or more commands in the first communications protocol into one or more commands in a second communications protocol and transmitting the one or more commands in the second communications protocol to a second controller of the device, and at the second controller, convert the received one or more commands in the second communications protocol into one or more commands to control one or more components of a second group of components of the device and transmitting the one or more commands to one or more components of the second group of components, wherein the one or more commands to control the one or more components of the second group of components are configured to cause the device to treat a biological fluid of the one or more biological fluids.

Additionally or alternatively to one or more examples disclosed above the second group of components comprise: one or more platforms, wherein each platform of the one or more platforms is configured to carry a biological fluid of the one or more biological fluids; and one or more light engines, wherein each light engine is configured to illuminate a biological fluid of the one or more biological fluids. Additionally or alternatively to one or more examples disclosed above the second group of components are configured to operate only in response to one or more commands transmitted from the second controller using the second communications protocol. Additionally or alternatively to one or more examples disclosed above a message transmitted in the second communications protocol includes information about the component that generated the message. Additionally or alternatively to one or more examples disclosed above, the first group of components include one or more components configured to allow an external user to interface with the device. Additionally or alternatively to one or more examples disclosed above, the first group of components includes a display configured to provide visual cues to the user of the device and configured to accept one or more inputs. Additionally or alternatively to one or more examples disclosed above the display is a touchscreen display configured to accept one or more touch inputs from the user of the device. Additionally or alternatively to one or more examples disclosed above, the first group of components includes a scanner configured to collect identifying information associated with a biological fluid being treated. Additionally or alternatively to one or more examples disclosed above, the second group of components further includes one or more agitators, wherein each agitator is configured to agitate a biological fluid of the one or more biological fluids so as to distribute the biological fluid within a container that is disposed on a platform of the one or more platforms of the device. Additionally or alternatively to one or more examples disclosed above, the electronic device comprises one or more treatment chambers configured to receive a biological fluid of the one or more biological fluids, and wherein each platform of the one or more platforms are configured to be positioned in a treatment chamber of the one or more treatment chambers. Additionally or alternatively to one or more examples disclosed above the second group of components further comprise one or more sensors configured to an operating condition of the device or a property of the biological fluid. Additionally or alternatively to one or more examples disclosed above the one or more light engines includes one or more arrays of light sources positioned to illuminate a biological fluid of the one or more biological fluids and wherein the one or more arrays of light sources are configured to emit light in an ultraviolet light spectrum. Additionally or alternatively to one or more examples disclosed above the one or more arrays of light sources each comprise a first light source channel configured to emit ultraviolet light with a first peak wavelength from about 315 nm to about 350 nm. Additionally or alternatively to one or more examples disclosed above the first light source channel comprises one or light sources, and each of which emits light having a full-width half-maximum (FWHM) spectral bandwidth of less than 20 nanometers. Additionally or alternatively to one or more examples disclosed above the one or more arrays of light sources comprise one or more light sources each of which emits light having a full-width half-maximum (FWHM) spectral bandwidth of less than 20 nanometers. Additionally or alternatively to one or more examples disclosed above the first light source channel comprises one or more light sources, and wherein the one or more light sources are light emitting diodes (LEDs). Additionally or alternatively to one or more examples disclosed above the one or more arrays of light sources comprise one or more light sources, and wherein the one or more light sources are light emitting diodes (LEDs). Additionally or alternatively to one or more examples disclosed above the one or more light engines further comprise one or more sensors configured to detect light energy from the one or more arrays of light sources. Additionally or alternatively to one or more examples disclosed above the second controller is configured to turn one or more of the second group of components on or off based on one or more signals transmitted by the one or more sensors. Additionally or alternatively to one or more examples disclosed above, the device further comprises: a first treatment chamber configured to receive a first biological fluid, a second treatment chamber configured to receive a second biological fluid: a first platform configured to carry the first biological fluid and to be positioned in the first treatment chamber, a second platform configured to carry the second biological fluid and to be positioned in the second treatment chamber, and a first array of light sources positioned to illuminate the first biological fluid in the first treatment chamber and a second array of light sources positioned to illuminate the second biological fluid in the second treatment chamber. Additionally or alternatively to one or more examples disclosed above the device is further configured to receive one or more inputs from a user of the device, and the device is configured to: transmit one or more commands using the first communications protocol to the first controller, wherein the one or more commands are configured to initiate a treatment process on a biological fluid of the one or more biological fluids, at the first controller, convert the one or more commands in the first communications protocol into one or more commands in the second communications protocol and transmit the one or more commands in the second communications protocol to the second controller, and at the second controller, convert the received one or more commands in the second communications protocol into one or more commands to control one or more components of the second group of components and transmit the one or more commands to the one or more components of the second group of components, wherein the one or more commands to control the one or more components of the second group of components are configured to cause the device to treat a biological fluid of the one or more biological fluids. Additionally or alternatively to one or more examples disclosed above wherein treating the one or more biological fluids comprises illuminating the biological fluids for a duration and at an intensity sufficient to inactivate a pathogen in the biological fluids.

BRIEF DESCRIPTIONS OF THE DRAWINGS

DETAILED DESCRIPTION

Figure 1:
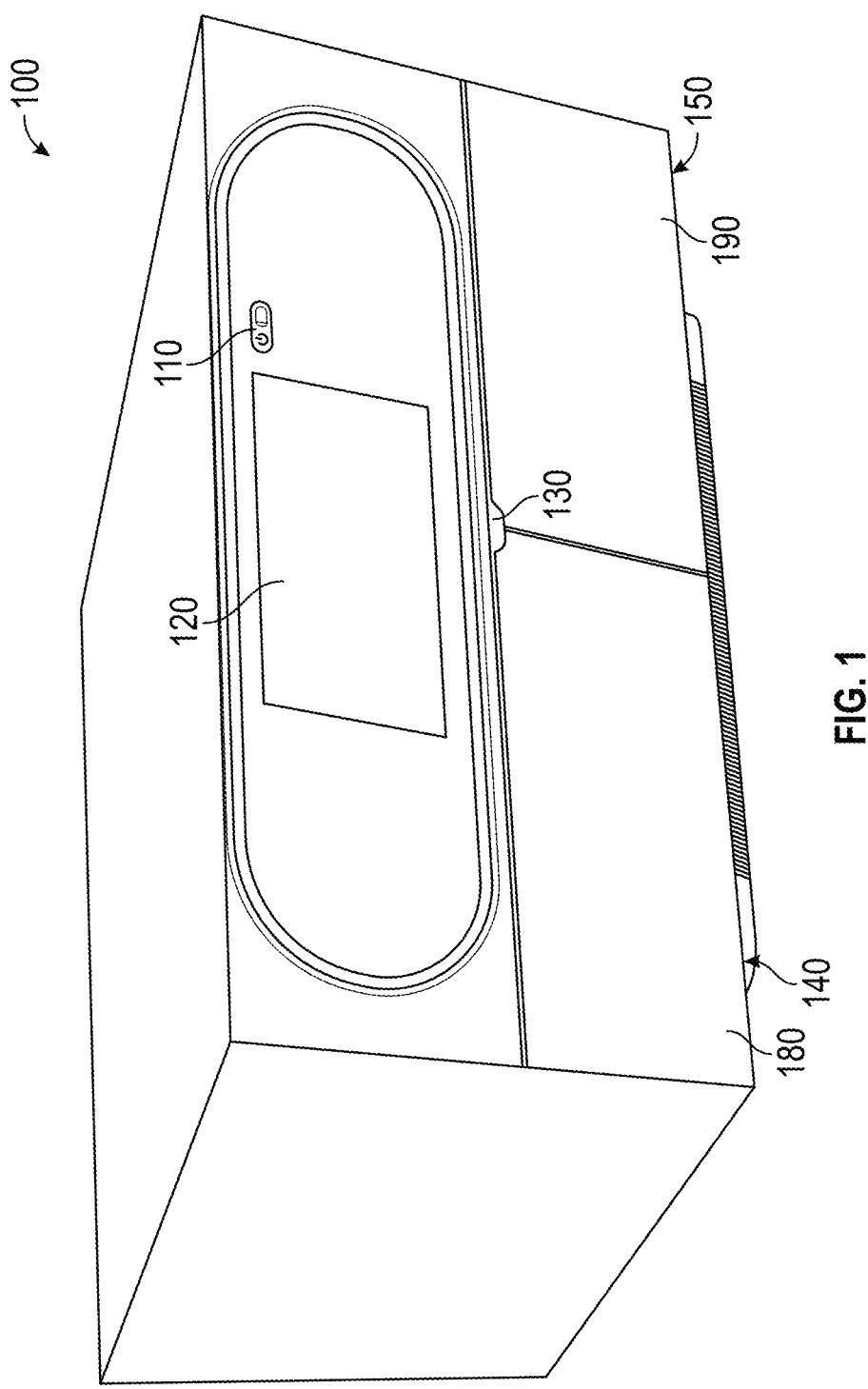
FIG. 1 illustrates an exemplary device for treating biological fluids according to examples of the disclosure.

The following description sets forth exemplary methods, parameters, and the like. It should be recognized, however, that such description is not intended as a limitation on the scope of the present disclosure but is instead provided as a description of exemplary embodiments.

In the following description of the disclosure and embodiments, reference is made to the accompanying drawings in which are shown, by way of illustration, specific embodiments that can be practiced. It is to be understood that other embodiments and examples can be practiced, and changes can be made, without departing from the scope of the disclosure.

In addition, it is also to be understood that the singular forms "a," "an," and "the" used in the following description are intended to include the plural forms as well unless the context clearly indicates otherwise. It is also to be understood that the term "and/or" as used herein refers to and encompasses any and all possible combinations of one or more of the associated listed items. It is further to be understood that the terms "includes," "including," "comprises," and/or "comprising," when used herein, specify the presence of stated features, integers, steps, operations, elements, components, and/or units but do not preclude the presence or addition of one or more other features, integers, steps, operations, elements, components, units, and/or groups thereof.

Some portions of the detailed description that follow are presented in terms of algorithms and symbolic representations of operations on data bits within a computer memory. These algorithmic descriptions and representations are the means used by those skilled in the data processing arts to most effectively convey the substance of their work to others skilled in the art. An algorithm is here, and generally, conceived to be a self-consistent sequence of steps (instructions) leading to a desired result. The steps are those requiring physical manipulations of physical quantities. Usually, though not necessarily, these quantities take the form of electrical, magnetic, or optical signals capable of being stored, transferred, combined, compared, and otherwise manipulated. It is convenient at times, principally for reasons of common usage, to refer to these signals as bits, values, elements, symbols, characters, terms, numbers, or the like. Furthermore, it is also convenient at times to refer to certain arrangements of steps requiring physical manipulations of physical quantities as modules or code devices without loss of generality.

However, all of these and similar terms are to be associated with the appropriate physical quantities and are merely convenient labels applied to these quantities. Unless specifically stated otherwise as apparent from the following discussion, it is appreciated that, throughout the description, discussions utilizing terms such as "processing," "computing," "calculating," "determining," "displaying," or the like refer to the action and processes of a computer system, or similar electronic computing device, that manipulates and transforms data represented as physical (electronic) quantities within the computer system memories or registers or other such information storage, transmission, or display devices.

Certain aspects of the present invention may include process steps and instructions described herein in the form of an algorithm. It should be noted that the process steps and instructions of the present invention could be embodied in software, firmware, or hardware, and, when embodied in software, they could be downloaded to reside on, and be operated from, different platforms used by a variety of operating systems.

FIG. 1 illustrates an exemplary system 100 for treating biological fluids. As used herein, a "biological fluid" refers to any fluid that is found in or derived from an organism (e.g., human, animal, plant, microorganism), or that comprises one or more components (e.g., biologics) found in, isolated from, or derived from an organism, including synthetic versions thereof. Biological fluids may include, but are not limited to, blood and blood products, vaccines, cells (e.g., primary cells, cell lines, cell cultures), natural and recombinant peptides or proteins (e.g., therapeutics, antibodies), bacterial cultures, virus suspensions and the like. As used herein, "blood product" refers to blood (e.g., whole blood) or a component or derivative of blood such as, for example, red blood cells, white blood cells, platelets, plasma or components thereof (e.g., coagulation factors, albumin, fibrinogen), cryoprecipitate and cryo-poor (e.g., cryo-reduced) plasma, or a combination of one or more of such components that have been separated from blood. In one more examples, a biological fluid may further comprise a non-biological fluid, such as for example, a physiological solution (e.g., diluent solution), including but not limited to saline, buffered solution, nutrient solution, platelet additive solution (PAS) and/or anticoagulant solution. In one more examples, when the biological fluid is positioned (e.g., the biological fluid is in a container, such as a treatment bag positioned or carried on a platform) in a chamber (not shown) of the biological fluid treatment system, the biological fluid is illuminated by light (e.g., visible light, ultraviolet light) having a certain spectral profile at specified intensities for a determined time period.

System 100 includes a power switch 110, display 120, scanner 130, platform 140, and platform 150. Although system 100 in FIG. 1 includes the described elements, examples of system 100 can include different combinations of the described elements or additional elements without departing from the scope of the disclosure. In some examples, the system 100 can couple, via a wired or a wireless connection, to a computing device (e.g., computer, mobile device) (not shown).

In some examples, in response to an input to the power switch 110, power is provided to the system 100. For example, the power switch 110 can be mechanical button. When the system 100 is off, in response to a push of the power switch 110, power is provided to the system 100 (e.g., the system 100 turns on). When the system 100 is on, in response to a push of the power switch 110, the provided power to the system 100 ceases (e.g., the system 100 turns off). In some examples, during treatment, the system 100 stays on and does not turn off in response to a push of the power switch.

As another example, the power switch 110 can be a capacitive switch that can be activated with a touch input (e.g., by placing a user's finger on the power switch). As yet another example, the power switch can be a button having two or more states. The power switch can be at an "off" state when the power switch is at a first position (e.g., unpressed, flipped to a first side). The power switch can be at an "on" state when the power switch is at a second position (e.g., pressed, flipped to a second side).

In some examples, the display 120 is a touchscreen. For example, the display 120 can be a capacitive touchscreen or a resistive touchscreen. In some examples, the display 120 is configured to display a graphical user interface (GUI) for operating the system 100. In some embodiments, the display 120 is configured to receive input from the scanner 130. In one more examples, the display 120 is configured to receive input on the GUI. For example, a GUI object of a plurality of GUI objects displayed on the GUI can be selected by providing a user's manual input (e.g., touch or hover input) on the touchscreen. In response to receiving the input, the system 100 can perform an operation associated with the selected GUI object. For example, a GUI object may be associated with initiation of a biological fluid treatment, and in response to receiving an input selecting the GUI object, the system 100 initiates a process to treat a biological fluid. In one more examples, the display 120 is configured to display instructions to a user operator (e.g., operator instructions) on the GUI. In some embodiments, the display 120 is configured to display input from the scanner 130 to a user operator. In some embodiments, the display 120 is configured to display input from sound that is detected by an audio input (e.g., one or more microphones) and processed (e.g., speech-to-text conversion) by one or more processors into a visual form (e.g., command text, command code) on the display 120 that the user can recognize as an input command, such as for example a user's voice command that is detected by one or more microphones (e.g., located in any arrangement internal to, external to, and/or part of the exterior housing of the system 100) and converted by one or more processors into command text on the display 120 that the user can recognize as an input command. In some embodiments, the display 120 is configured to display input from a user's visual motion (e.g., hand motion or gesture, object in a swiping motion) that is detected by a motion sensor (e.g., one or more cameras) and processed (e.g., motion-to-text conversion, motion-to-graphic conversion) by one or more processors into a visual form (command text, command code, command icon, command graphic) on the display 120 that the user can recognize as an input command, such as for example a user's hand gesture (e.g., hand in a swiping motion) that is detected by one or more cameras (e.g., located in any arrangement internal to, external to, and/or part of the exterior housing of the system 100) and converted by one or more processors into visual command text or a visual graphic on the display 120 that the user can recognize as an input command. Although one display 120 is illustrated in FIG. 1, the system 100 can include more than one display in some examples.

By using a touchscreen as an input component and/or input from the scanner 130, the user interface of system 100 can be simplified. For example, the use of a touchscreen can reduce the need for physical buttons corresponding to features that can be similarly performed using the touch screen. Biological fluid treatment using system 100 can be more efficient using the simplified user interface.

Although the power switch 110 and display 120 are described as elements of the system 100 that can be configured to receive user input, other elements or means of input can be included in the system 100 without departing from the scope of the disclosure. For example, the system 100 can include directional input keys, a mouse pad, or a scroll wheel configured for navigating a GUI displayed on the display 120. In some embodiments, the system 100 is configured to receive a user's input from sound that is detected by an audio input (e.g., one or more microphones) and processed (e.g., speech-to-text conversion) by one or more processors into a language form (e.g., command text, command code) that the system 100 can recognize as an input command, such as for example a user's voice command that is detected by one or more microphones (e.g., located in any arrangement internal to, external to, and/or part of the exterior housing of the system 100) and converted into command text by one or more processors that the system 100 can recognize as an input command. In some embodiments, the system 100 is configured to receive input from a user's visual motion (e.g., hand motion or gesture, object in a swiping motion) that is detected by a motion sensor (e.g., one or more cameras) and processed (e.g., motion-to-text conversion) by one or more processors into a language form (e.g., command text, command code), such as for example a user's hand gesture (e.g., hand in a swiping motion) that is detected by one or more cameras (e.g., located in any arrangement internal to, external to, and/or part of the exterior housing of the system 100) and converted into command text by one or more processors that the system 100 can recognize as an input command. Alternatively or in addition, system 100 can be configured to receive input other than user input, such as for example, from one or more sensors implemented for system 100. Non-limiting examples of various sensors that may be implemented (e.g., in a treatment chamber) include one or more light sensors configured to measure the light intensity at various portions of the treatment chamber and/or the light intensity incident on various portions of one or more biological fluids, one or more air flow sensors, one or more heat sensors for measuring the temperature of treatment chamber and/or the temperature of one or more biological fluids, one or more sensors for detecting the presence and/or type of one or more biological fluids (e.g., pressure sensors, optical retro-reflective sensors, optical transmissive sensors, label readers, scanners, barcode scanners, RFID sensors, etc.), one or more sensors for detecting a property (e.g., transmissivity) of the biological fluid (e.g., optical sensors, spectroscopic sensors), one or more sensors for detecting a photochemical compound in the biological fluid (e.g., fluorescence spectrometry), and one or more sensors (e.g., ultrasonic sensors) positioned to detect the fluid depth of a portion (e.g., various portions) of one or more biological fluids.

In some embodiments, system 100 can be configured to receive input from one or more scanners implemented for system 100. In some examples, the scanner 130 is configured to obtain information relating to biological fluids. In some examples, the scanner 130 can be configured to obtain identifying information related to the biological fluids to be treated. For example, the biological fluid may be stored in a container (e.g., hemocompatible bag, treatment bag) (not shown), and the container or other containers in a multi-container assembly (e.g., disposable fluid processing set) can include a tag or label or designated area containing the identifying information in some form, such as a visible form (e.g., a barcode, a QR code, etc.) and/or transmittable form (e.g., electronic identifier, radio frequency identification (RFID)). In some examples, the identifying information can represent information about the biological fluid product, such as biological or other parameters (e.g., donation ID, product code, set code, lot number, type of biological fluid, volume of biological fluid, content of biological fluid, for example platelet number) and treatment parameters. In some examples, the biological or other parameters, optionally in combination with input from one or more sensors and/or user inputs may determine a treatment parameter. In some, multiple sets of identifying information can be obtained. For example, multiple sets of identifying information may be located on one or more respective containers associated with (e.g., containing or part of a multi-container assembly containing) the biological fluid, and the sets of identifying information can be obtained from the respective containers by scanner 130. In some examples, the scanner may be a multi-scan scanner (e.g., camera with multi-scan functionality, camera in cooperation with circuitry (e.g., hardware and/or software) having multi-scan processing functionality, handheld scanner with multi-scan functionality, handheld scanner in cooperation with circuitry (e.g., hardware and/or software) having multi-scan processing functionality, label reader with multi-scan functionality, label reader in cooperation with circuitry (e.g., hardware and/or software) having multi-scan processing functionality) configured to sequentially or substantially simultaneously capture (e.g., acquire) multiple sets of identifying information (e.g., multiple barcodes, multiple QR codes, multiple labels, optical character recognition (OCR) of different strings or arrangements of alphanumeric text and/or symbols, image recognition, etc.) located on one or more containers, such as for example capturing multiple sets of identifying information in "batch" mode (e.g., in response to a single user input or a single device input that commands, triggers, or otherwise initiates a multi-scan operation that acquires multiple sets of identifying information). A single multi-scan operation may capture, sequentially or substantially simultaneously (e.g., simultaneously), multiple sets of identifying information (e.g., in a single operation, a camera can capture one or more images of one or more labels that show the multiple parameters of a biological product, such as for example donation ID, product code, set code, lot number, type of biological fluid, volume of biological fluid, content of biological fluid; in a single operation, a multi-scanner can perform one or more scans of one or more labels that show the multiple parameters above). In some embodiments, the multi-scanner or the system 100 is configured to recognize (and/or convert into another form recognized by the multi-scanner or system 100) the captured multiple sets of identifying information (e.g., recognizing (and/or deciphering) barcodes, QR codes, alphanumeric text and/or symbols, images) captured in a multi-scan operation. After capturing multiple sets of identifying information (e.g., in captured image(s), performed scan(s)), a multi-scanner can convey or communicate them (e.g., via a wired or wireless connection) to the system 100 in recognized (and/or converted) form (e.g., in a language form that the system 100 can already recognize, for example as parameter data) or in unrecognized form (e.g., captured image(s), performed scan(s)). If in unrecognized form, the system 100 can process the captured multiple sets of identifying information into a recognized form. The system 100 can assign the multiple sets of identifying information to corresponding fields (e.g., auto-populating information fields) of the GUI of the display 120 when displaying the GUI for the treatment chamber associated with the biological fluid to be treated. Thus, a multi-scan operation may provide data entry of all or most parameter data for a biological fluid into multiple specific data fields via an auto-population technique that may be convenient, efficient, and time-saving. For example, with a multi-scan operation, a user need not perform multiple scans in any particular order to capture multiple sets of identifying information that may be presented in a certain order (e.g., no need to perform a scan for each label on a container in the visual order of specific data fields presented on the GUI to the user.

In some example, the identifying information can enter a field of view of the scanner 130, and the scanner 130 can obtain the identifying information when the information is in the field of view. For example, a user can hold a biological fluid treatment container (e.g., bag) with a barcode facing the scanner 130, and the scanner 130 can image-capture, scan, or read the barcode; based on the obtained barcode, the system 100 can determine information about the biological fluid product. In some examples, the identifying information can enter a detection range of the scanner 130, and the scanner 130 can obtain the identifying information when the information is in the detection range. For example, a user can hold a biological fluid treatment bag with an RFID tag near the scanner 130, and the scanner 130 can detect the RFID tag; based on information obtained from the detected RFID tag, the system 100 can determine information about the biological fluid product.

Although the scanner 130 is illustrated as being located on an exterior of the system 100 in FIG. 1, the scanner 130 can be located at different locations of the system 100. In one more examples, the scanner 130 is located inside the system 100. For example, the scanner 130 can be located at a top of a treatment chamber of system 100. The scanner 130 can obtain information related to the biological fluid after the biological fluid is placed on a platform and/or in the chamber.

In some examples, the scanner 130 can be included in a device coupled to system 100. For example, the scanner 130 can be included in a handheld scanner (e.g., barcode scanner, QR code scanner) coupled to system 100. In some examples, a scanner 130 couples to system 100 via a wired connection. In some examples, a scanner 130 couples to system 100 via a wireless connection.

Although one scanner 130 is illustrated in FIG. 1, system 100 can include more than one scanner 130. For example, system 100 can include a plurality of treatment chambers, and each treatment chamber may have a corresponding scanner (e.g., internal scanner). As another example, system 100 can include a plurality of platforms and each platform may have a corresponding scanner (e.g., external scanner) located near or at an opening for a respective platform. As the platform moves through the opening, a container (e.g., treatment bag) containing the biological fluid can traverse a field of view of a respective scanner, and information, associated with the biological fluid, in visible form on the container or an associated container of a multi-container assembly can be obtained by the respective scanner.

In some examples, the platform 140 (e.g., drawer, tray, well, plate, stage) is configured to carry the biological fluid (e.g., a container containing the biological fluid) during treatment. In some examples, the platform is moveable (e.g., slideably moveable, configured to translate from inside the treatment chamber to outside the treatment chamber) between the interior and exterior of the treatment chamber (e.g., partially out of the treatment chamber). In some examples, the platform further comprises a first panel 180 movable between a closed position and an open position, wherein the first panel 180 covers a first opening to the first treatment chamber in the closed position, wherein the first panel 180 uncovers the first opening to the first treatment chamber in the open position. In some embodiments, the first panel is attached to, integrated with, or formed together with the platform 140 (e.g., in a drawer configuration). In some examples, the first panel 180 is a separate structure from the platform 140 (e.g., a separate hinged door that covers and uncovers the first opening to the first treatment chamber), and the platform 140 can slide in and out of the first treatment chamber separately from the first panel 180.

In some examples, the platform and/or first panel can be locked to remain in the closed position during treatment. The system 100 can prevent a user from prematurely accessing the content of the platform 140 (e.g., accessing the treatment chamber) during treatment by locking the first panel to remain in the closed position. In one more examples, the first panel can be locked by a pin (e.g., solenoid and pin) or magnetic lock mechanism. The system 100 can permit a user to access, by unlocking the first panel, the content of the platform 140 before and after treatment (e.g., to load the biological fluid on the platform 140, to unload the biological fluid from the platform 140) or after an input (e.g., an input on the GUI, an input to open latch, an input to a button switch).

As illustrated in FIG. 1, the structure of the platform 150 symmetrically mirrors structure of the platform 140 about a vertical axis. In one more examples, the platform 150 is substantially similar to platform 140 in size, shape, or orientation. As illustrated, the platforms 140 and 150 are arranged horizontally, such that the first biological fluid and the second biological fluid, when positioned on the first platform and on the second platform, respectively, are within a same plane. As the first panel 180 may be associated with the platform 140, as discussed above, a second panel 190 may be associated with the platform 150.

Although two platforms are illustrated in FIG. 1 as being a part of system 100, the system 100 can include one platform or more than two platforms that are substantially similar to platform 140 or platform 150 without departing from the scope of the disclosure. In general, the number of illustrated platforms and treatment chambers associated with systems 100-300 are exemplary; embodiments of systems 100-300 may include different numbers and combinations of platforms, treatment chambers, and their associated elements (e.g., scanners, light arrays, compartments) without departing from the scope of the disclosure. For example, in one more examples, a system can include only one chamber with only one platform. In one more examples, a system can include only one chamber with two or more platforms. In some embodiments, a system can include two chambers, each with only one platform. In some embodiments, a system can include two chambers, each with two or more platforms.

In some examples, the platform comprises a first compartment and a second compartment separate from the first compartment. In some examples, the first compartment is configured to hold (e.g., carry) a container (e.g., container of a multi-container assembly) containing a biological fluid in a position for illumination. In some examples, the second compartment is configured to hold a container (e.g., container of a multi-container assembly) not containing a biological fluid in a position not for illumination. In some examples, the platform is configured to separately carry at least a first container with a first biological fluid and a second container with a second biological fluid. In some examples, the platform is transparent (e.g., substantially transparent, >95% transparent, >90% transparent, >80% transparent, >80% transparent) to light with a wavelength within 100 nm (e.g., 75 nm, 50 nm, 40 nm, 30 nm, 20 nm) of the peak wavelength of light used for illumination. In some example, the platform is transparent (e.g., substantially transparent, >95% transparent, >90% transparent, >80% transparent, >80% transparent) to ultraviolet light (e.g., UV-A, UV-B, and/or UV-C).

Figure 2A:
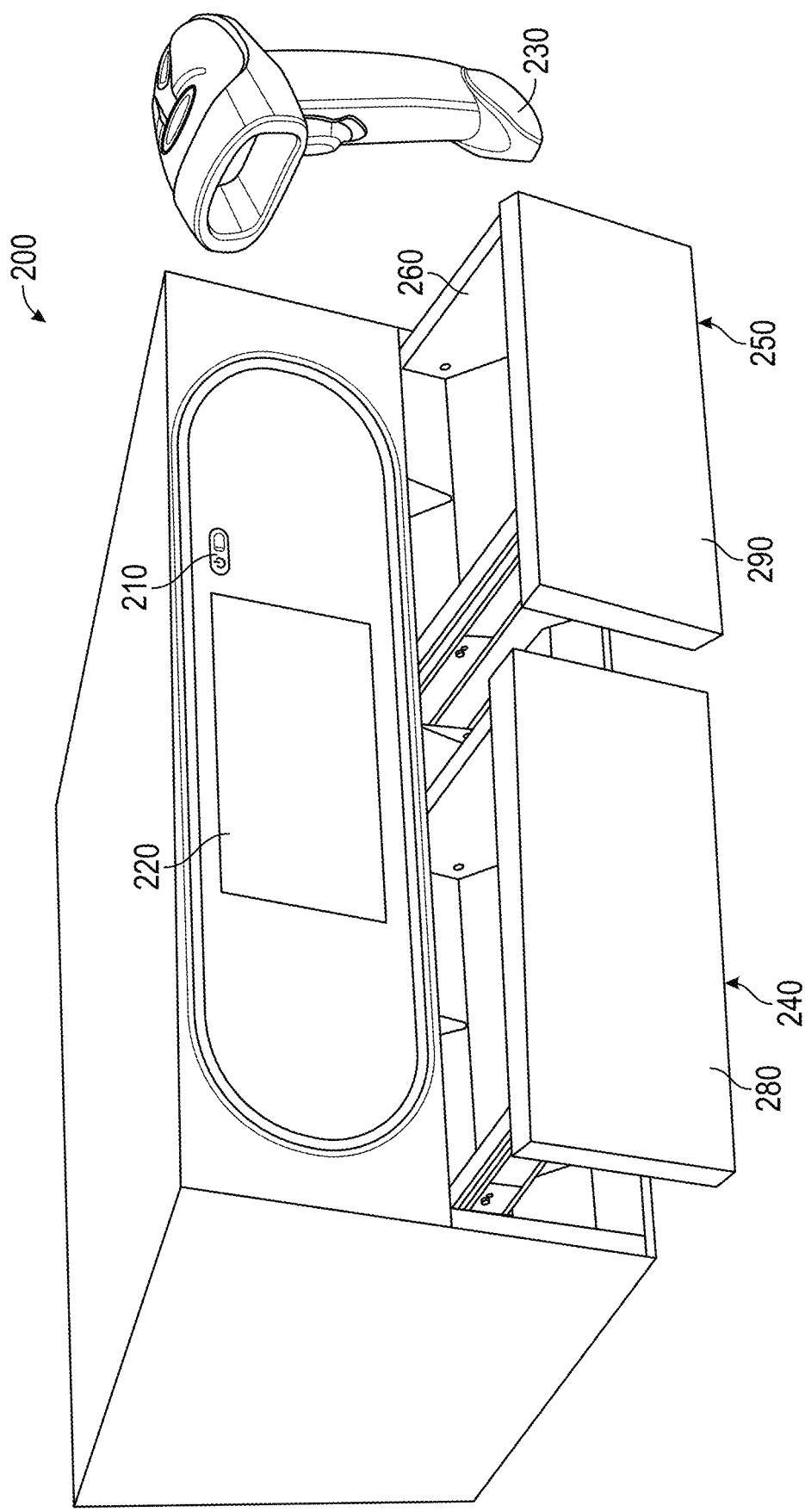
FIG. 2A-2C illustrate other exemplary views of the device described with respect to FIG. 1 for treating biological fluids according to examples of the disclosure.
Figure 2B:
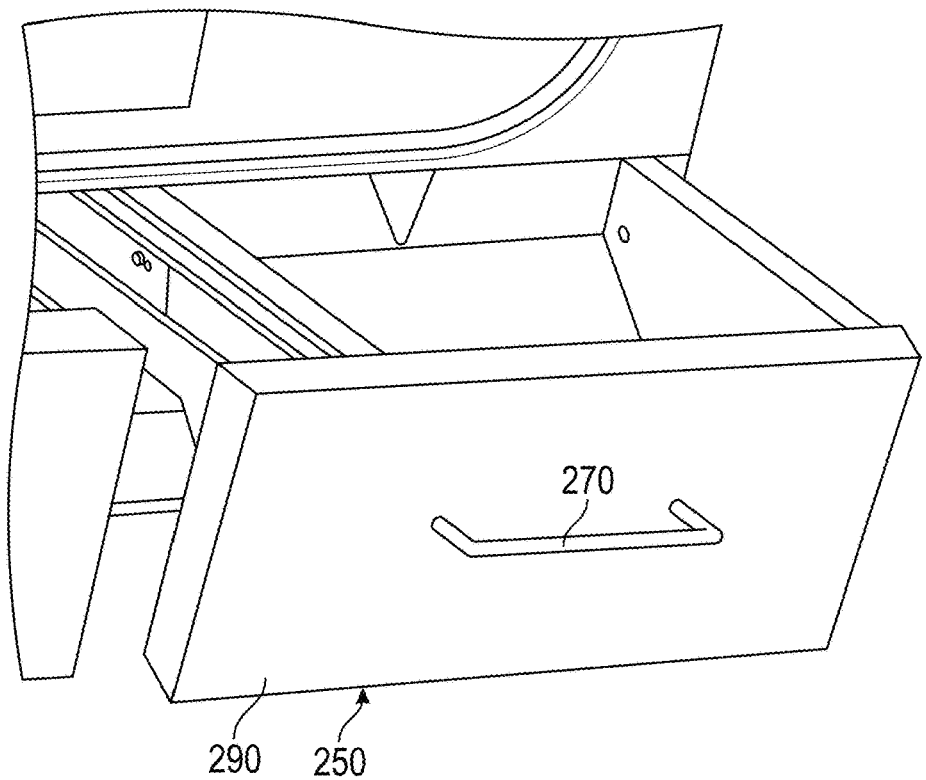
Figure 2C:
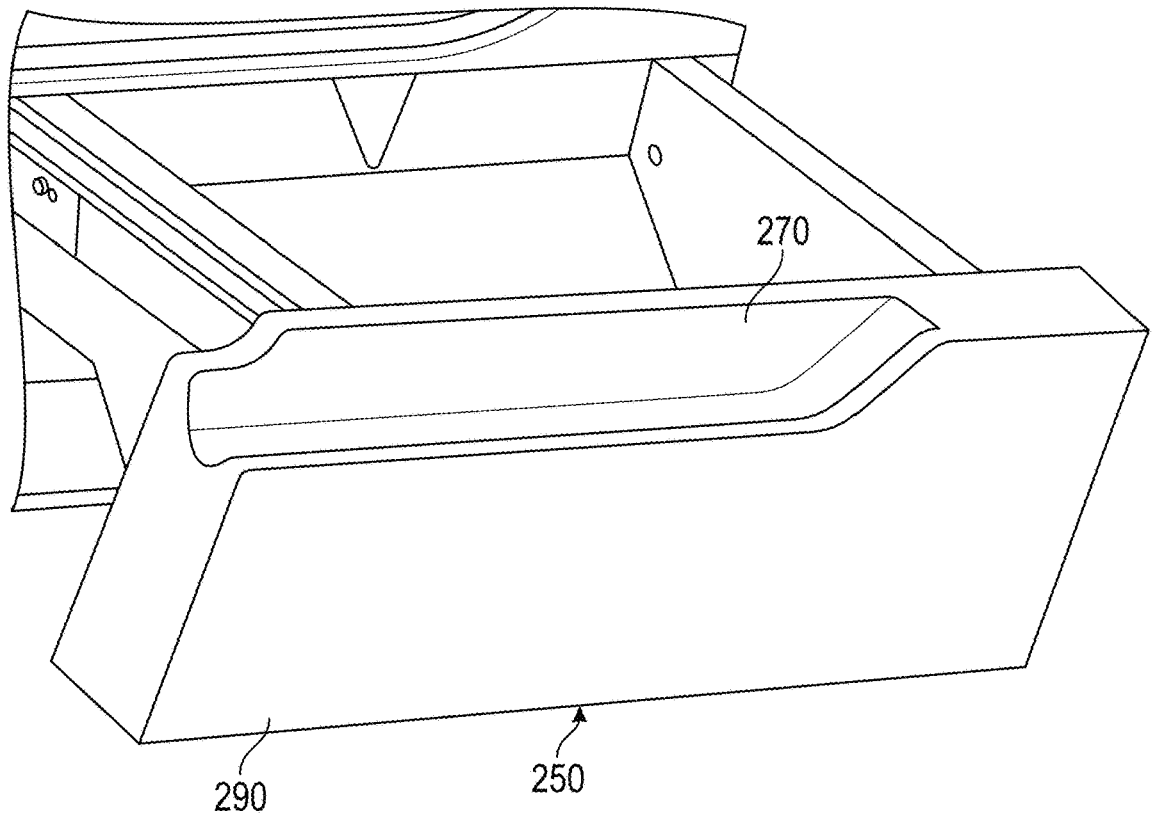

FIG. 2 illustrates an exemplary system 200 for treating biological fluids. In one more examples, the system 200 is substantially similar to system 100, as illustrated in FIG. 1. Power switch 210 can correspond to power switch 110. Display 220 can correspond to display 120. Platforms 240 and 250 can respectively correspond to platforms 140 and 150. Panels 280 and 290 can respectively correspond to panels 180 and 190.

In some examples, the system 200 includes an external scanner 230. As illustrated, the external scanner 230 is external to a housing that houses the other elements and can be operatively coupled to a processor of the system 200. In some examples, the external scanner 230 is a handheld scanner. Although the external scanner 230 is illustrated with a wireless connection in FIG. 2A, the external scanner 230 can be operatively coupled using a wired connection.

As illustrated in FIG. 2A, platforms 240 and 250 are in drawer configurations at an open position, in contrast with platforms 140 and 150 being at a closed position in FIG. 1. Although both platforms 240 and 250 are illustrated as in drawer configurations being open in FIG. 2, one platform in a drawer configuration can also open at a time (e.g., with the other remaining closed).

In some embodiments, a first panel 280 and a second panel 290, associated with the platforms 240 and 250, lack any handles. In some embodiments, at a closed position, a panel can be opened by applying a force opposite to the opening direction (e.g., pushing an exterior of a panel to engage a push latch that releases the panel to open). In some embodiments, at a closed position, a panel can be opened using mechanical components (e.g., motors, servos) to actuate the panel (e.g., as a hinged door, as part of the platform in a drawer configuration). In some embodiments, the system can permit a user to access the content of a platform by opening the panel (e.g., by a spring mechanism), to allow the user to further manually slide out the platform. For example, in accordance with a determination that a treatment procedure is starting or complete, the system can mechanically open one or more panels corresponding to the treatment for loading or unloading one or more biological fluid containers (e.g., treatment bags).

In some examples, the platforms include a compartment 260 substantially similar to the compartments described herein. Although FIG. 2A illustrates a platform as having one compartment visible (e.g., for a platform in a drawer configuration at an open position), each of the platforms in system 200 can include any number of compartments without departing from the scope of the application.

Figure 3:
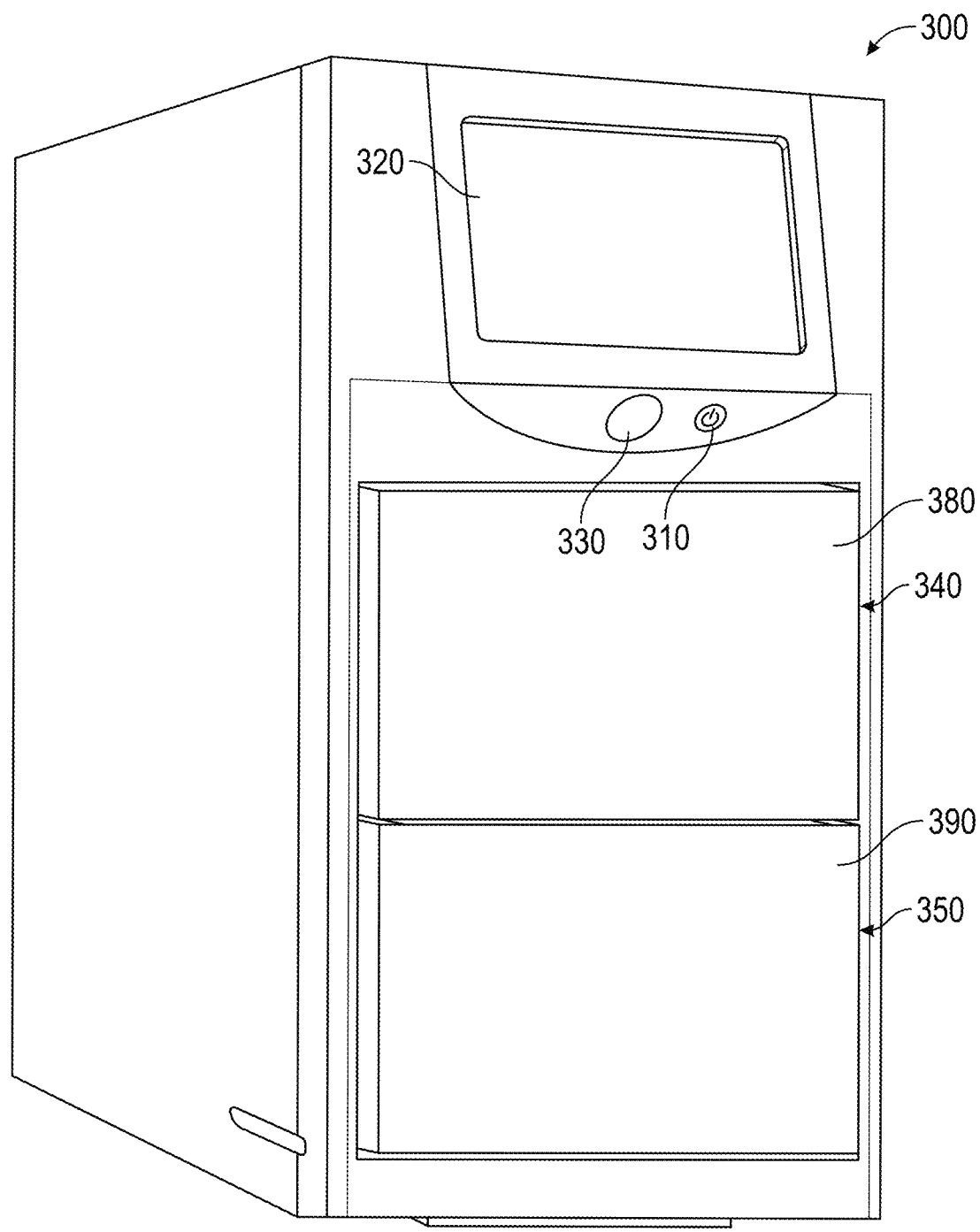
FIG. 3 illustrates another exemplary device for treating biological fluids according to examples of the disclosure.

FIG. 3 illustrates an exemplary system 300 for treating biological fluids. In some examples, the system 300 is substantially similar to system 100, with a difference that the treatment chambers and platforms are arranged vertically. Power switch 310 can correspond to power switch 110. Display 320 can correspond to display 120. Scanner 330 can correspond to scanner 130. In contrast to system 100, in which the platforms 140 and 150 are arranged horizontally, platforms 340 and 350 are arranged vertically such that the first biological fluid and the second biological fluid, when positioned on the first platform and on the second platform, respectively, are in parallel planes. Also in contrast to system 300, in which panels 180 and 190 are arranged horizontally, panels 380 and 390 are arranged vertically.

The examples of FIGS. 1-3 are meant to provide an exemplary context for the system architectures described in detail below and are not meant to be limiting to the architectures in any way. The system architectures presented herein can be utilized on a variety of biological fluid treatment devices not described above with respect to FIGS. 1-3.

Figure 4:
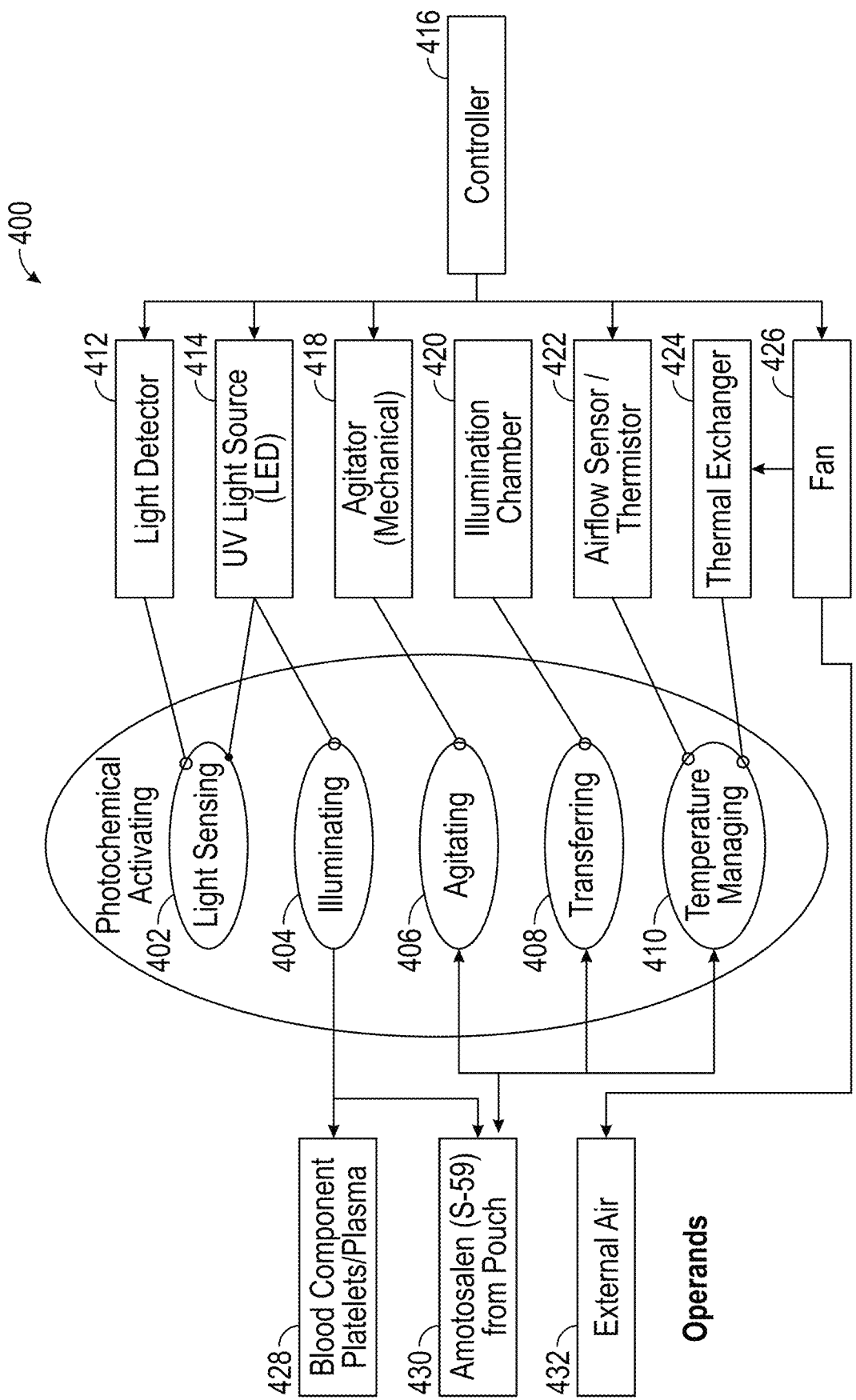
FIG. 4 illustrates an exemplary process diagram of a system for treating a biological fluid according to examples of the disclosure.

FIG. 4 illustrates an exemplary process diagram of a system for treating a biological fluid according to examples of the disclosure. The diagram 400 of FIG. 4 illustrates the various components of a system for treating a biological fluid and presents a mapping of what function each component performs with respect to the treatment process. In the example of FIG. 4, the diagram can include a plurality of processes 402, 404, 406, 408, and 410 that can collectively work with one another to treat a biological fluid. In one or more examples, the device and system for treating the biological fluid sample can include a light sensing process 402 that is configured to monitor the amount of light (e.g., UV light) being applied to a particular biological fluid. In one or more examples, the light sensing process 402 can utilize (e.g., interact with) one or more light sensors (e.g., photodiodes) 412. Light sensors 412 can be configured to convert light into electrical current. In one or more examples, the electrical current emitted from light sensor 412 can be proportional to the amount of light received by the light sensor. The light sensing process 402 can also interact with one or more light sources (e.g., UV light sources) 414. In one example, the light sensing process 402 can include using one or more light sensors 412 to sense the light being generated by the one or more light sources (e.g., UV light sources) 414. In one or more examples, the current generated by the light sensors 412 based on the light generated by the light sources (e.g., UV light sources) 414 can be transmitted to the controller 416 so as to allow the controller 416 to ensure that the biological fluid under treatment is receiving the appropriate amount of light needed to treat the biological fluid.

In one or more examples, the device and system for treating the biological fluid can include an illumination process 404 that is configured to generate the light (e.g., UV light) being applied a particular biological fluid. The illumination process 404 can include causing the one or more light sources (e.g., UV light sources) 414 to generate light (e.g., UV light) (as discussed above) so as to treat a biological fluid. As shown in diagram 400, the illumination process 404 can act upon both a biological fluid, such as for example, a blood component (e.g., platelets/plasma) 428 as well as a photoactive pathogen inactivation compound 430 such a psoralen and/or amotosalen in (e.g., in admixture with) a biological fluid.

In one or more examples, the device can include an agitation process 406. The agitation process 406 can be configured to agitate the contents of the treatment container (e.g., during treatment of the biological fluid by illumination) to distribute (e.g., evenly distribute) the biological fluid and/or a pathogen inactivation compound in (e.g., in admixture with) the biological fluid. The agitation may facilitate the treatment, for example, by providing for mixing of a compound (e.g., photochemical compound, pathogen inactivation compound) in the biological fluid, or by maintaining a component (e.g., platelets, cells) of the biological fluid in suspension. In one or more examples, the agitation process 406 can include causing a mechanical agitator 418 to agitate the biological fluid (e.g., the biological fluid with photoactive pathogen inactivation compound 430). In one or more examples, the controller 416 can control the agitator 418 so as to carry out the agitation process 406. In one or more examples, one or more motors or servos (e.g., mounted to or on the platform) may be configured as the mechanical agitator 418. The one or more motors or servos may be physically coupled to the platform or a portion thereof and may move the platform or portion thereof forward and backward (e.g., along rails or tracks) to agitate biological fluid carried on the platform (e.g., biological fluid in a container). The one or more motors or servos may be part of any suitable agitation design (e.g., a lead screw design where one or more motors or servos move a lead screw that is attached to the platform or portion thereof, a belt-driven design where one or more motors or servos move one or more belts that rotate one or more gears (e.g., gears with teeth) that engage and move one or more tracks attached to the platform or portion thereof) and may operate based on control signals from electrical wiring that is electrically connected to control circuitry. In one or more examples, the system may be configured to control (e.g., adjustably control) one or more aspects of the agitation movement, such as offset (i.e., stroke length of the reciprocating (e.g., linear, forward-and-backward, etc.) motion during agitation), speed, acceleration, and deceleration. In some embodiments, the agitation speed may be adjustable (e.g., adjusted to have different speeds between different treatments, adjusted to have different speeds during a single treatment, adjusted based on a predetermined speed plan, adjusted dynamically in real-time based on a user's input in real-time), Such control circuitry may control the agitator (e.g., one or more motors or servos) based on a control program implemented as software and/or hardware of the control circuitry.

In one or more examples, the device can include a transferring process 408. In one or more examples, the transferring process 408 can include the operations required to transfer the biological fluid into and out of the treatment chamber. For instance, the transferring process 408 can include operating one or more doors of the illumination chamber 420 to open, close, and lock or unlock depending on which part of the treatment process the device is currently engaged in. In one or more examples, the controller 416 can control the illumination chamber 420 so as to carry out the transferring process 408.

In one or more examples, the device can include a temperature managing process 410. In one or more examples, the temperature process 410 can include the operation of one or more hardware components that are collectively configured to keep the device within a particular temperature range. In one or more examples, the temperature managing process 410 can be configured to operate one or more fans 426 that can act on external air 432 to cool the device in the event that the device's internal temperature exceeds a pre-determined temperature threshold. In one or more examples, the controller 416 can control the one or more fans 426 so as to carry out the temperature managing process 410.

Figure 5:
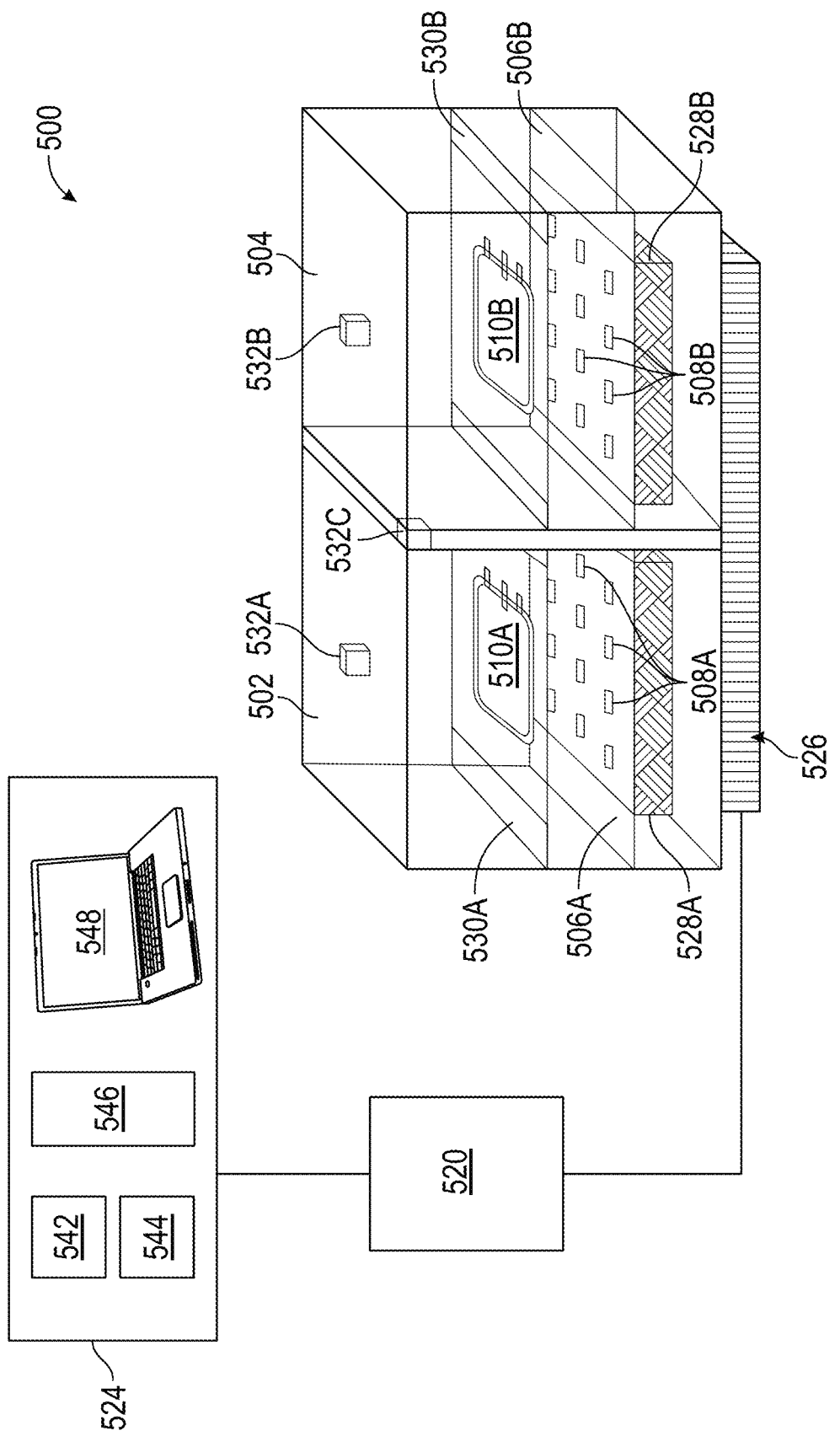
FIG. 5 is a perspective view of an exemplary system for treating a biological fluid according to examples of the disclosure.

FIG. 5 is a perspective view of an exemplary system 500 for treating a biological fluid. In some embodiments, the system 500 is substantially similar to system 100, as illustrated in FIG. 1. Exemplary system 500 for treating biological fluids includes a first treatment chamber 502 and a second treatment chamber 504 for receiving one or more biological fluids 510 and an array of light sources 506 positioned to illuminate one or more biological fluids 510. In some embodiments, the array of light sources 506 may comprise the only light sources in chamber 502 and 504 positioned to illuminate the one or more biological fluids 510. In other embodiments described below with respect to FIG. 6, multiple light source arrays may be used to illuminate one or more biological fluids positioned in various embodiments of chamber 502 and 504. As described herein, an "array of light sources" means one or more light sources disposed on any two or three dimensional surface (e.g., contiguous surface, non-contiguous surface).

One or more light source channels may be included in an array of light sources of the present disclosure. In some embodiments, one or more light source channels 508 are included in array of light sources 506. Although specific light sources are illustrated as belonging to a specific light source channel, it is understood that different combinations of the light sources can form different light source channels. Each light source channel 508 may be a set of one or more light sources having the same wavelength (e.g., peak wavelength, maximum peak wavelength). In an exemplary set, one light source may have a peak wavelength. In another exemplary set, two light sources may have the same peak wavelength to each other. In yet another exemplary set, each of a plurality of light sources may have different peak wavelengths from each other. In a further exemplary set, a first subset of one or more light sources may have one peak wavelength, and a second subset of one or more light sources may have a different peak wavelength. Within a light source channel having a plurality of light sources, all of the light sources may have respective peak wavelengths (e.g., maximum peak wavelengths) that all are within a wavelength range (e.g., range of 1-20 nm, 1-10 nm; e.g., 1 nm, 2 nm, 3 nm, 4 nm, 5 nm, or more, greater than and/or less than a particular wavelength) for the light source channel. For example, in some embodiments, within a light source channel having a plurality of light sources, all of the light sources may have peak wavelengths within a range set forth in the present disclosure, such as for example of about 315 nm to about 350 nm (e.g., about 315 nm to about 335 nm, about 330 nm to about 350 nm, about 340 nm to about 350 nm). In a light source channel, each light source may be any light source providing light of a desirable property (e.g., peak wavelength, maximum peak wavelength, spectral bandwidth) including, but not limited to, solid-state lighting (SSL), light-emitting diodes (LEDs), organic light-emitting diodes (OLEDs), polymer light-emitting diodes (PLEDs), and laser diodes. The light source channels of the array of light sources may be connected in a series circuit, in a parallel circuit, or in a combination of series and parallel circuits. In a light source channel having a plurality of light sources, those light sources may be controlled together or separately.

Each light source channel may be adjusted or set to emit light at different intensities (e.g., adjust the light dosage, adjust the energy dosage) at which light of the one or more peak wavelengths are applied to one or more portions of the biological fluid. For example, each light source channel may emit light at maximum intensity (e.g., 100%), or at less than maximum intensity (e.g., about 90%, about 80%, about 70%, about 60%, about 50%, about 40%, about 30%, about 20%, or less).

Each light source channel may emit various types of light. For example, each light source channel may emit ultraviolet light, ultraviolet A light, ultraviolet B light, ultraviolet C light, and/or visible light. Additionally, each light source channel may emit light of various peak wavelengths. For example, the emitted peak wavelength(s) may be in the ultraviolet A spectrum (e.g., 315-400 nm), the ultraviolet B spectrum (e.g., 280-315 nm), the ultraviolet C spectrum (e.g., 100-280 nm, 200-280 nm, 240-280 nm), or the visible light spectrum (e.g., 400-800 nm). In some embodiments, the emitted peak wavelength(s) may be between about 240 nm and about 250 nm, about 245 nm and about 255 nm, about 250 nm and about 260 nm, about 255 nm and about 265 nm, about 260 nm and about 270 nm, about 265 nm and about 275 nm, about 270 nm and about 280 nm, or about 275 nm and about 285 nm. In some embodiments, the emitted peak wavelength(s) may be between about 280 nm and about 290 nm, about 285 nm and about 295 nm, about 290 nm and about 300 nm, about 300 nm and about 310 nm, about 305 nm and about 315 nm, or about 310 nm and about 320 nm. In some embodiments, the emitted peak wavelength(s) may be between about 315 nm and about 325 nm, about 320 nm and about 330 nm, about 325 nm and about 335 nm, about 330 nm and about 340 nm, about 335 nm and about 345 nm, about 340 nm and about 350 nm, about 345 nm and about 355 nm, about 350 nm and about 360 nm, about 355 nm and about 365 nm, about 360 nm and about 370 nm, about 365 nm and about 375 nm, about 370 nm and about 380 nm, about 375 nm and about 385 nm, about 380 nm and about 390 nm, about 385 nm and about 395 nm, about 390 nm and about 400 nm. In some embodiments, the emitted peak wavelength may be about 240 nm, about 245 nm, about 250 nm, about 255 nm, about 260 nm, about 265 nm, about 270 nm, about 275 nm, about 280 nm, about 285 nm, about 290 nm, about 295 nm, about 300 nm, about 305 nm, about 310 nm, about 315 nm, about 320 nm, about 325 nm, about 330 nm, about 335 nm, about 340 nm, about 345 nm, about 350 nm, about 355 nm, about 360 nm, about 365 nm, about 370 nm, about 375 nm, about 380 nm, about 385 nm, about 390 nm, about 395 nm, or about 400 nm. In some embodiments, the emitted peak wavelength may be between about 255 nm and about 275 nm (e.g., between about 260 nm and about 270 nm, about 265 nm). In some embodiments, the emitted peak wavelength may be between about 275 nm and about 295 nm (e.g., between about 280 nm and about 290 nm, about 285 nm). In some embodiments, the emitted peak wavelength may be between about 300 nm and about 320 nm (e.g., between about 305 nm and about 315 nm, about 310 nm). In some embodiments, the emitted peak wavelength may be between about 315 nm and about 335 nm (e.g., between about 320 nm and about 330 nm, about 325 nm). In some embodiments, the emitted peak wavelength may be between about 330 nm and about 350 nm (e.g., between about 335 nm and about 345 nm, between about 340 nm and about 350 nm, about 340 nm, about 345 nm). In some embodiments, the emitted peak wavelength may be between about 355 nm and about 375 nm (e.g., between about 360 nm and about 370 nm, about 365 nm). In some embodiments, the emitted peak wavelength may be between about 375 nm and about 395 nm (e.g., between about 380 nm and about 390 nm, about 385 nm). In some embodiments, the emitted peak wavelengths may be in the (1) ultraviolet A spectrum (e.g., 315-400 nm); and (2) the ultraviolet B spectrum (e.g., 280-315 nm) or the ultraviolet C spectrum (e.g., 100-280 nm, 200-280 nm, 240-280 nm). In some embodiments, the emitted peak wavelength is in the ultraviolet A spectrum, between about 315 nm and about 350 nm (e.g., between about 320 nm and about 345 nm, between about 315 nm and about 335 nm, between about 330 nm and about 350 nm, between about 340 nm and about 350 nm).

In some embodiments, all light source channels of array of light sources may emit light of about the same (e.g., within variance ±1 nm, ±2 nm, ±3 nm, ±4 nm, ±5 nm, ±6 nm, ±7 nm, ±8 nm, ±9 nm, ±10 nm) peak wavelength (e.g., maximum peak wavelength). For example, in some embodiments, all light source channels of an array of light sources may emit light of a peak wavelength of 325±10 nm, 330±10 nm, 335±10 nm, 340±10 nm, 325±5 nm, 330±5 nm, 335±5 nm, 340±5 nm, 345±5 nm, 345±4 nm, 345±3 nm, or 345±2 nm. Light source channels may include a plurality of light sources with different peak wavelengths (e.g., measured peak wavelengths) within a range of variability. In some embodiments, the average peak wavelength across a plurality of light sources for a single light source channel may be the same as a particular peak wavelength for a particular light source in the single light source channel. In other embodiments, the average peak wavelength across a plurality of light sources of a single light source channel may be different (e.g., about 1 nm, 2 nm, 3 nm, 4 nm, 5 nm or more, greater than or less than) than all particular peak wavelengths of each light source in the single light source channel. In some embodiments, some light source channels may emit light of a first peak wavelength and other light source channels may emit light of a second peak wavelength. The first peak wavelength may differ from the second peak wavelength by at least (e.g., greater than) 5 nm, 10 nm, 15 nm, or 20 nm, or more. For example, in a non-limiting embodiment, a first light source channel may emit light with a peak wavelength in the ultraviolet A spectrum, such as described above (e.g., between about 315 nm and about 335 nm, between about 330 nm and about 350 nm, between about 340 nm and about 350 nm) and a second light source channel may emit light with a peak wavelength in the ultraviolet C spectrum, such as described above (e.g., between about 250 nm and about 260 nm, between about 260 nm and about 270 nm) or the ultraviolet B spectrum, such as described above (e.g., between about 305 nm and about 315 nm). In another non-limiting embodiment, a first light source channel may emit light with a peak wavelength in the ultraviolet A spectrum, such as described above (e.g., between about 330 nm and about 350 nm, between about 340 nm and about 350 nm) and a second light source channel may emit light with a peak wavelength also in the ultraviolet A spectrum, such as described above (e.g., between about 315 nm and about 335 nm, between about 355 nm and about 375 nm). In some embodiments, a first peak wavelength is the average peak wavelength of the one or more light sources of a first light source channel. In some embodiments, the array of light sources may comprise first, second, and third light source channels that each respectively emits light of a first, second, and third peak wavelength. In some embodiments, a first peak wavelength may differ from a second peak wavelength by at least (e.g., greater than) 5 nm, 10 nm, 15 nm, or 20 nm or more, and/or the second peak wavelength may differ from a third peak wavelength by at least (e.g., greater than) 5 nm, 10 nm, 15 nm, or 20 nm or more. Alternatively, each of a first, second, and third peak wavelengths may differ from each another by at least (e.g., greater than) 5 nm, 10 nm, 15 nm, or 20 nm, or more. In some embodiments, an array of light sources may comprise first, second, third, and fourth light source channels that each respectively emits light of a first, second, third, and fourth peak wavelength. In some embodiments, at least two, at least three, or at least four of the first, second, third, and fourth peak wavelengths may differ from each other by at least (e.g., greater than) 5 nm, 10 nm, 15 nm, or 20 nm or more. Alternatively, each of the first second, third, and fourth peak wavelengths may differ from each other by at least (e.g., greater than) 5 nm, 10 nm, 15 nm, or 20 nm, or more. Alternatively, the first peak wavelength may be the about same as (e.g., equal to, within variance+1 nm, 2 nm, 3 nm, 4 nm, ±5 nm) the third peak wavelength, the second peak wavelength may be the about same as (e.g., equal to) the fourth peak wavelength, and the first peak wavelength may differ from the second peak wavelength by at least (e.g., greater than) 5 nm, 10 nm, 15 nm, or 20 nm.

In some embodiments, each light source channel may emit light with a narrow spectral bandwidth. For example, the full-width half-maximum (FWHM) spectral bandwidth of light (e.g., spectral bandwidth at the maximum peak intensity) emitted by each light source channel may be less than 20 nm, less than 18 nm, less than 16 nm, less than 14 nm, less than 12 nm, less than 10 nm, less than 9 nm, less than 8 nm, less than 7 nm, less than 6 nm, or less than 5 nm. In some embodiments, the full-width half-maximum (FWHM) spectral bandwidth of light emitted by each light source channel is within 10 nm less than and/or within 10 nm greater than the peak wavelength (e.g., no more than 10 nm greater than, no more than 10 nm less than the peak wavelength). In some embodiments, the full-width half-maximum (FWHM) spectral bandwidth of light emitted by each light source channel may be greater than 1 nm, greater than 2 nm, greater than 3 nm, or greater than 4 nm, or more. In other examples, 50% of the maximum peak intensity of light emitted by each light source channel is within 10 nm, within 9 nm, within 8 nm, within 7 nm, within 6 nm, within 5 nm, within 4 nm, or within 3 nm of the peak wavelength (e.g., no more than 10 nm greater than, no more than 10 nm less than the peak wavelength; within 10 nm less than, within 10 nm more than the peak wavelength). In other examples, the light intensity at 50% of the maximum peak intensity of light emitted by each light source channel is within a spectral width less than 20 nm, less than 18 nm, less than 16 nm, less than 14 nm, less than 12 nm, less than 10 nm, less than 9 nm, less than 8 nm, less than 7 nm, less than 6 nm, or less than 5 nm (e.g., no more than 10 nm greater than, no more than 10 nm less than the peak wavelength; within 10 nm less than, within 10 nm greater than the peak wavelength). Commercially available LEDs and laser diodes are non-limiting examples of light sources that may provide such narrow spectral bandwidth illumination at the peak wavelengths discussed above.

In some embodiments, one or more of the peak wavelength of emission, the spectral bandwidth of emission, the duration of emission, and the intensity of emission of each light source channel 508 may be adjusted or set.

Adjustment of these various light source channel parameters may be performed by a control circuitry 520 operatively coupled (e.g., communicatively coupled) to treatment chambers 502 and 504, light source arrays 506, and/or to computer system 524. As used herein, "operatively coupled" refers to any wired or wireless connection between two or more components that enables the two or more components to exchange information, control instructions, and/or control signals. As will be discussed in more detail below, control circuitry 520 may receive control instructions and/or control signals from computer system 524 and send control instructions and/or control signals to various components of treatment chambers 502 and 504 to adjust or set various parameters associated with various components of chambers 502 and 504. Adjustment of various parameters of chambers 502 and 504 may be desirable to ensure that the chamber's treatment parameters are in accordance with the treatment profiles of the one or more biological fluids 510. It should be recognized that, in some examples, control circuitry 520 and/or the function of control circuitry 520 may be included within computer system 524. In some examples, control circuitry 520 may include computer system 524 and/or the function of computer system 524. In some examples, control circuitry 520 may be structurally attached to treatment chambers 502 and 504 (e.g., attached to external side, top, and/or bottom surface of treatment chambers 502 and 504). In some examples, control circuitry 520 may be integrated with treatment chambers 502 and 504 (e.g., located inside treatment chambers 502 and 504 or forming a part of the structure of treatment chambers 502 and 504).

Computer system 524 may be operatively coupled (wired or wirelessly) to control circuitry 520 and/or to any of the various sensors discussed herein. Computer system may include one or more processors 544 (544 in FIG. 5, 644 in FIG. 6), memory 542 (542 in FIG. 5, 642 in FIG. 6), an input/output (I/O) interface 546 (546 in FIG. 5, 646 in FIG. 6), and a user interface (UI) 548 (548 in FIG. 5, 648 in FIG. 6). One or more processors 544 may be one or more of any type of general purpose computer processor. Memory, or computer readable medium 542 may include one or more of readily available memory such as random access memory (RAM), read-only memory (ROM), floppy disk, hard disk, optical storage media (e.g., compact disc or digital video disc), flash drive, or any other form of digital storage, local or remote. In some examples, a non-transitory computer-readable storage medium of memory 542 may be used to store instructions for illuminating one or more biological fluids in accordance with their one or more treatment profiles, as will be discussed herein. Computer system 524 may encompass any variety of computers, such as a personal computer (PC), a desktop computer, a laptop, a computer terminal, a server computer, a tablet computer, a smartphone, a personal digital assistant (PDA), etc. In some examples, control circuitry 520 and/or the function of control circuitry 520 may be included within computer system 524.

At UI 548, a user may input one or more characteristics of a set of characteristics of one or more biological fluids (e.g., biological fluid 510). Alternatively, or additionally, the one or more characteristics of a set of characteristics of one or more biological fluids may be determined based on feedback input to computer system 524 and/or control circuitry 520 from one or more sensors for a treatment chamber (e.g., treatment chamber 502, treatment chamber 504). The characteristics of the set of characteristics of a biological fluid may include, for example, the type of the biological fluid (e.g., blood product, such as plasma, platelets, red blood cells; cells, such as eukaryotic cells; proteins, such as antibodies; vaccines), the photochemical agent in the biological fluid (e.g., type, volume, concentration), the volume of the biological fluid, the transmissivity of the biological fluid, the type and/or shape of the container carrying the biological fluid, and the temperature of the biological fluid.

At UI 548, a user may input one or more parameters that comprise the treatment profiles of one or more biological fluids (e.g., biological fluid 510). Alternatively or additionally, computer system 524 may automatically determine one or more parameters of the one or more treatment profiles of one or more biological fluids (e.g., biological fluids 510) based on the respective set of characteristics of the one or more biological fluids. In particular, memory 542 may store a computer program comprising instructions that map one or more characteristics of a biological fluid to one or more parameters of a treatment profile of the biological fluid for each biological fluid. The instructions that that map one or more characteristics of a biological fluid to one or more parameters of a treatment profile of the biological fluid for each biological fluid may be implemented as a set of user-programmable rules.

In some embodiments, array of light sources 506 may be thermally coupled to a heat exchanger 528 (e.g., heat sink, fin heat sink, heat exchanger that may be operatively coupled to and controlled by control circuitry 520). Heat exchanger 528 may draw thermal energy away from array 506 facing one or more biological fluids 510, thus minimizing the exposure of biological fluids 510 to thermal energy (e.g., thermal energy that may damage biological function). Further control of the temperature of chambers 502 and 504 and/or the temperature of the one or more biological fluids 510 may be provided by a heating/cooling unit 526 that may be operatively coupled to and controlled by control circuitry 520 and configured to adjust or set the temperature of chambers 502 and 504. Heating/cooling unit 526 may be any suitable technology known in the art, such as for example, a fan, heat pump, Peltier cooler and/or heat pipe. Heating/cooling unit 526 may be external to, inside, and/or integrated with chambers 502 and 504. For example, one or more fans may be positioned in the rear of the treatment chamber(s) to draw in air through an inlet on the exterior housing of system 500 and to expel the air through an outlet exhaust on the back of the exterior housing.

In some embodiments, heating/cooling unit 526 may be a heating unit or a cooling unit or a heating-and-cooling unit. Through the use of heating/cooling unit 526, system 500 can control the heating/cooling unit 526 to maintain the temperature of a biological fluid within a certain temperature range (e.g., a range of 1° C., a range of 2° C., a range of 3° C., etc.) during treatment of the biological fluid by illumination. For example, heat or temperature sensors can provide temperature indications or measurements to control circuitry 520 or to computer system 524 via control circuitry 520. If control circuitry 520 and/or computer system 524 processes or interpret the temperature indications or measurements as indicating the crossing of a certain threshold or condition related to a target temperature value or profile, control circuitry 520 and/or computer system 524 may instruct or command or enable or engage or actuate heating/cooling unit 526 to take action to adjust the temperature of chamber 502 or 504 and/or the temperature of the one or more biological fluids 510. For example, control circuitry 520 and/or computer system 524 may instruct or command or enable or engage or actuate one or more fans to start blowing to initiate cooling, to blow faster to provide an increased cooling rate, to blow slower to provide a decreased cooling rate, or to stop blowing to cease cooling. During treatment of the biological fluid by illumination, the one or more fans may run in operational cycles under the control of control circuitry 520 and/or computer system 524 in order to maintain the temperature of the biological fluid within a certain temperature range (e.g., a range of 1° C., a range of 2° C., a range of 3° C., etc.). Control circuitry 520 and/or computer system 524 may instruct or command or enable or engage or actuate any other suitable technology known in the art, such as for example, a fan, heat pump, Peltier cooler and/or heat pipe, or any combination of such technology to take action to adjust the temperature of chamber 502 or 504 and/or the temperature of the one or more biological fluids 510.

In some embodiments, the one or more fans may be located at the rear of the treatment chamber(s). The one or more fans may blow air in a front-to-back direction or in a back-to-front direction or both. In some embodiments, the one or more fans may draw in air to pass through the treatment chamber and expel the air through an exhaust at the rear of the system. Inlet air to the one or more fans may enter through vents located at or near the front or side(s) of the treatment chamber(s), and outlet air from the one or more fans may exit through vents located at the rear of the treatment chamber(s).

Treatment chambers 502 and 504 may further include a plurality of interior surfaces configured to absorb light (e.g., each configured to absorb light), such as for example, one or more walls made of or coated by a material (e.g., black plastic, black silicate, black paint) that substantially absorbs light of certain wavelengths. Alternatively or in addition, in some embodiments, treatment chambers 502 and 504 may further include one or more interior surfaces configured to reflect light (e.g., each configured to reflect light), such as for example, one or more walls made of or coated by a material that substantially reflects light of certain wavelengths.

Treatment chambers 502 and 504 may further comprise a platform 530 configured to hold one or more biological fluids 510 (e.g., containers of biological fluids). Platform 530 may be any support suitable for carrying biological fluids or containers of biological fluids. Platform 530 may be positioned in a "drawer configuration" so that it is slidably movable manually into and out of chambers 502 and 504. Platform 530 may be slidably movable automatically by any suitable actuator, such as an electric motor or servo. Platform 530 carrying biological fluids 510 may be positioned above the light source array 506 with light source array 506 facing platform 530. However, in other embodiments, platform 530 carrying one or more biological fluids may be positioned below light source array 506 with light source array 506 facing the platform 530.

In some embodiments, the system 500 includes one or more scanners 532 in the treatment chambers 502 and 504. The one or more scanners 532 can be located above the biological fluids 510 when the fluids are positioned for treatment (e.g., scanner 532A in the first treatment chamber, scanner 532B in the second treatment chamber). As illustrated, one or more scanners 532 (e.g., scanner 532C) can also be located between the first and second treatment chambers at the exterior (e.g., exterior housing, exterior surface) of the system 500. The one or more scanners 532 can be substantially similar to the scanners described herein. When the biological fluids are loaded into a respective treatment chamber, a respective scanner within a respective chamber can obtain identifying information about the biological fluids, as described herein. In some embodiments, the one or more scanners can be positioned at a first opening of the first treatment chamber 502, at a second opening of the second treatment chamber 504, or at openings of both chambers.

Figure 6:
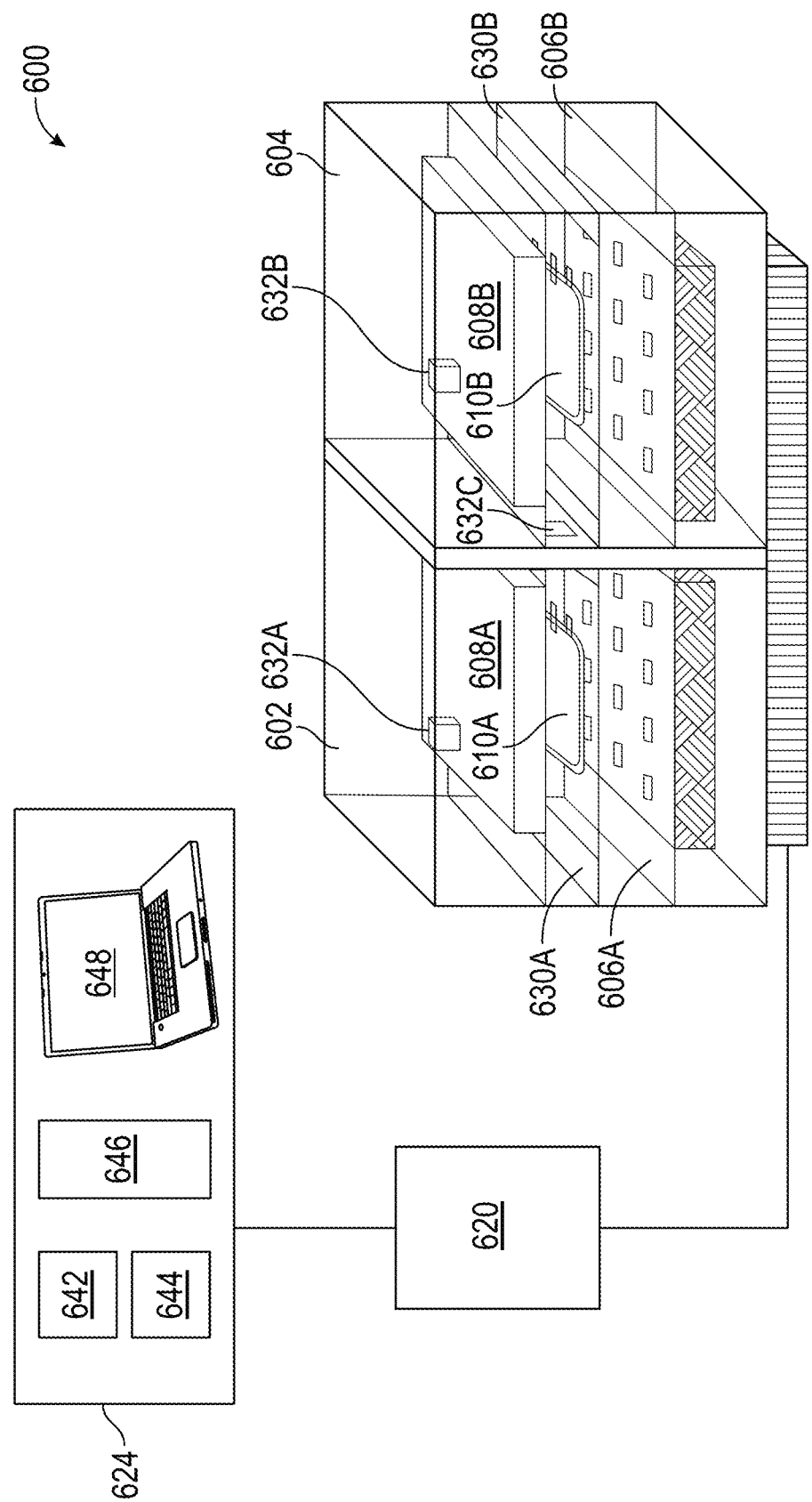
FIG. 6 is a perspective view of an exemplary system for treating a biological fluid according to examples of the disclosure.

FIG. 6 is a perspective view of an exemplary system 600 for treating a biological fluid. In some embodiments, the system 600 is substantially similar to system 500, as illustrated in FIG. 5. Exemplary system 600 for treating biological fluids includes a first treatment chamber 602 and a second treatment chamber 604 for receiving one or more biological fluids 610, a first array of light sources 606 in each chamber positioned to illuminate from below one or more biological fluids 610, a second array of light sources 608 in each chamber positioned to illuminate from above one or more biological fluids 610, a platform 630 in each chamber configured to hold one or more biological fluids 610 (e.g., containers of biological fluids), and a sensor (e.g., scanner) 632 configured to obtain identifying information of a biological fluid loaded into the treatment chamber. The first array of light sources 606 and second array of light sources 608 positioned above and below the one or more biological fluids 610 in each of treatment chambers 602 and 604 provides for illuminating the biological fluid from either one (i.e., above or below) or two (i.e., both) directions.

The system 600 can include scanner 632A positioned at the exterior (e.g., exterior housing, exterior surface) of the system 600 at a location associated with the first treatment chamber 602 (e.g., at or near an opening of first treatment chamber 602) and scanner 632B positioned at the exterior (e.g., exterior housing, exterior surface) of the system 600 at a location associated with the second treatment chamber 604 (e.g., at or near an opening of second treatment chamber 604). The system 600 can also include scanner 632C positioned inside system 600 (e.g., on an inner wall, in a ceiling, in a floor) between the first and second treatment chambers 602 and 604. In some embodiments, the scanner 632C can be configured to obtain information from containers positioned in either treatment chamber or both treatment chambers.

Figure 7:
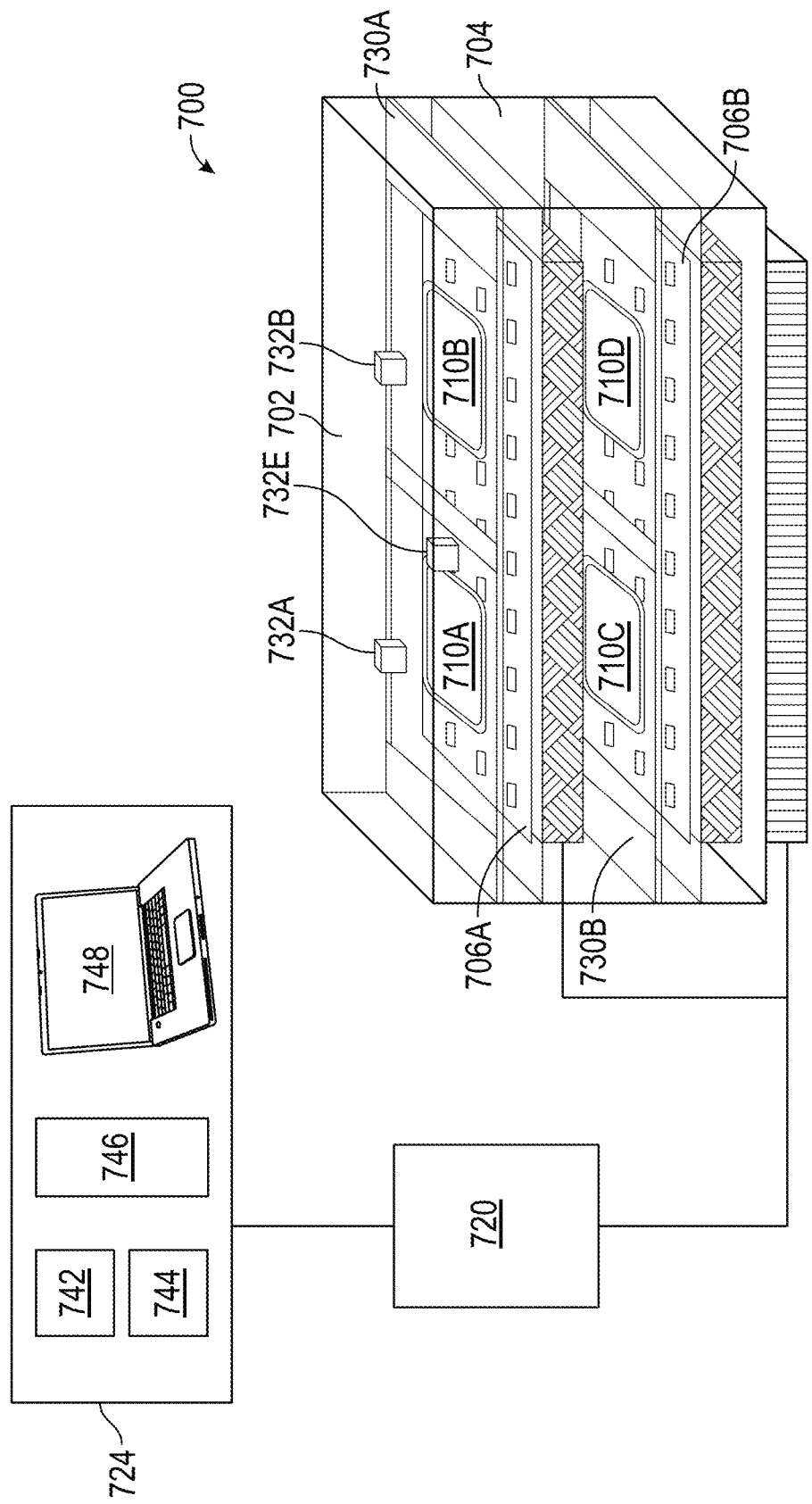
FIG. 7 illustrates a perspective view of an exemplary system for treating a biological fluid according to examples of the disclosure.

FIG. 7 is a perspective view of an exemplary system 700 for treating a biological fluid. In some embodiments, the system 700 is substantially similar to system 300, as illustrated in FIG. 3, and system 600, as illustrated in FIG. 6, differing in that the first treatment chamber 702 and the second treatment chamber 704 are positioned vertically (above and below each other) in system 700. Exemplary system 700 for treating biological fluids includes a first treatment chamber 702 and a second treatment chamber 704 for receiving one or more biological fluids 710, a first array of light sources 706 in each chamber positioned to illuminate from below one or more biological fluids 710, a platform 730 in each chamber configured to hold one or more biological fluids 710 (e.g., containers of biological fluids), and a sensor (e.g., scanner) 732 configured to obtain identifying information of a biological fluid loaded into the treatment chamber. Platform 730 carrying biological fluids 710 may be positioned above the light source array 706 with light source array 706 facing platform 730. However, in other embodiments, platform 730 carrying one or more biological fluids may be positioned below light source array 706 with light source array 706 facing the platform 730. Each of light source chambers 702 and 704 may further comprise a second array of light sources (not shown), positioned above and below the one or more biological fluids 710, such as for example similar to system 600, as illustrated in FIG. 6.

The system 700 can include scanners 732A and 732B positioned inside the first treatment chamber 702 (e.g., in the ceiling above compartments for biological fluids 710A and 710B) and two scanners similarly positioned inside the second treatment chamber 704 (e.g., in the ceiling above compartments for biological fluids 710C and 710D). The system 700 can also include scanner 732E positioned at the exterior (e.g., exterior housing, exterior surface) of the system 700 between the first and second treatment chambers 702 and 704. In some embodiments, the scanner 732E can be configured to obtain information from containers positioned in either treatment chamber or both treatment chambers (e.g., when a platform in a drawing configuration is in an open position in the field of view of scanner 732E, when RFID tags are within the detection range of scanner 732E).

Figure 8A:
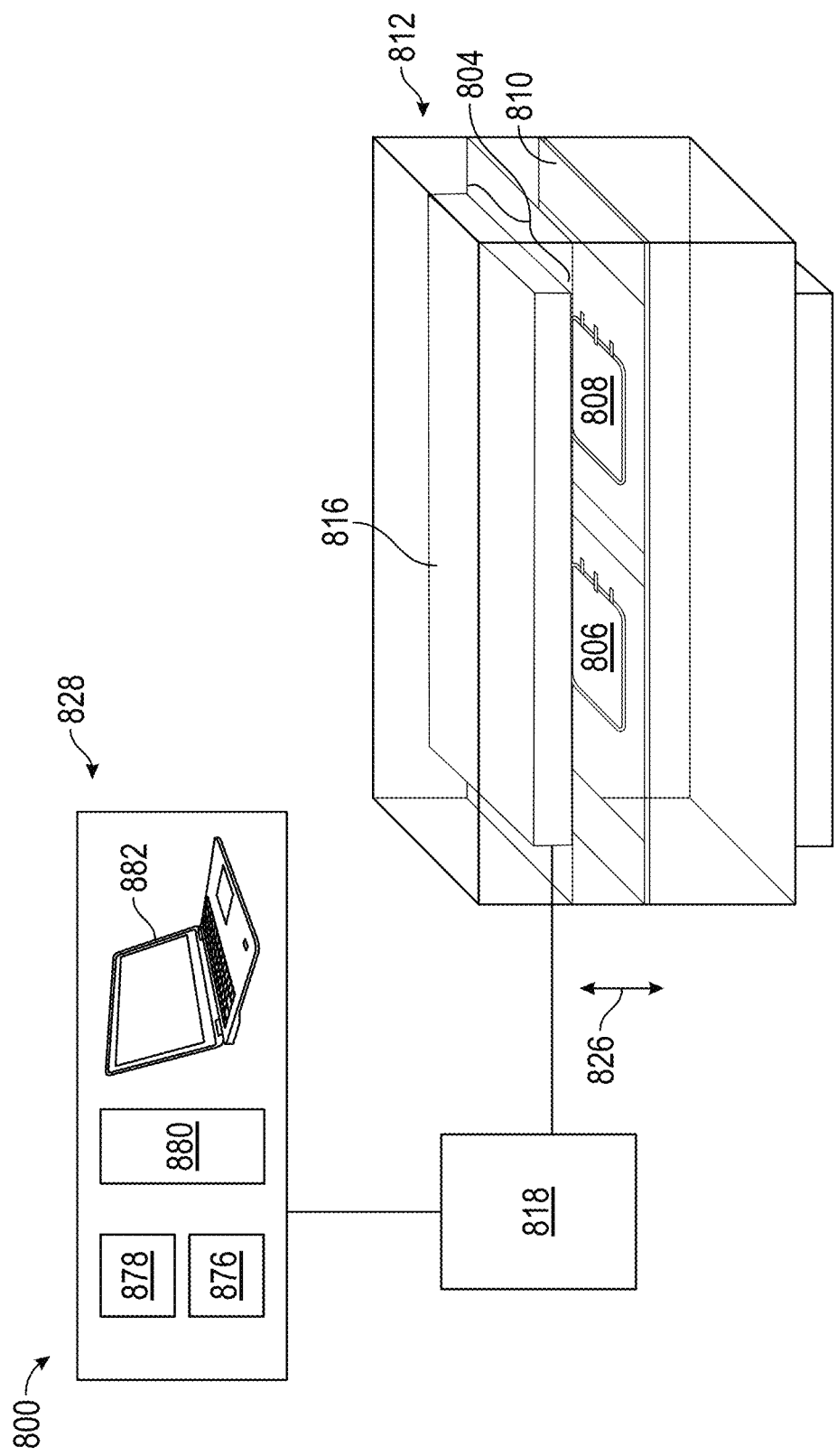
FIG. 8A-8B illustrate a perspective view of an exemplary system for treating a biological fluid according to examples of the disclosure.
Figure 8B:
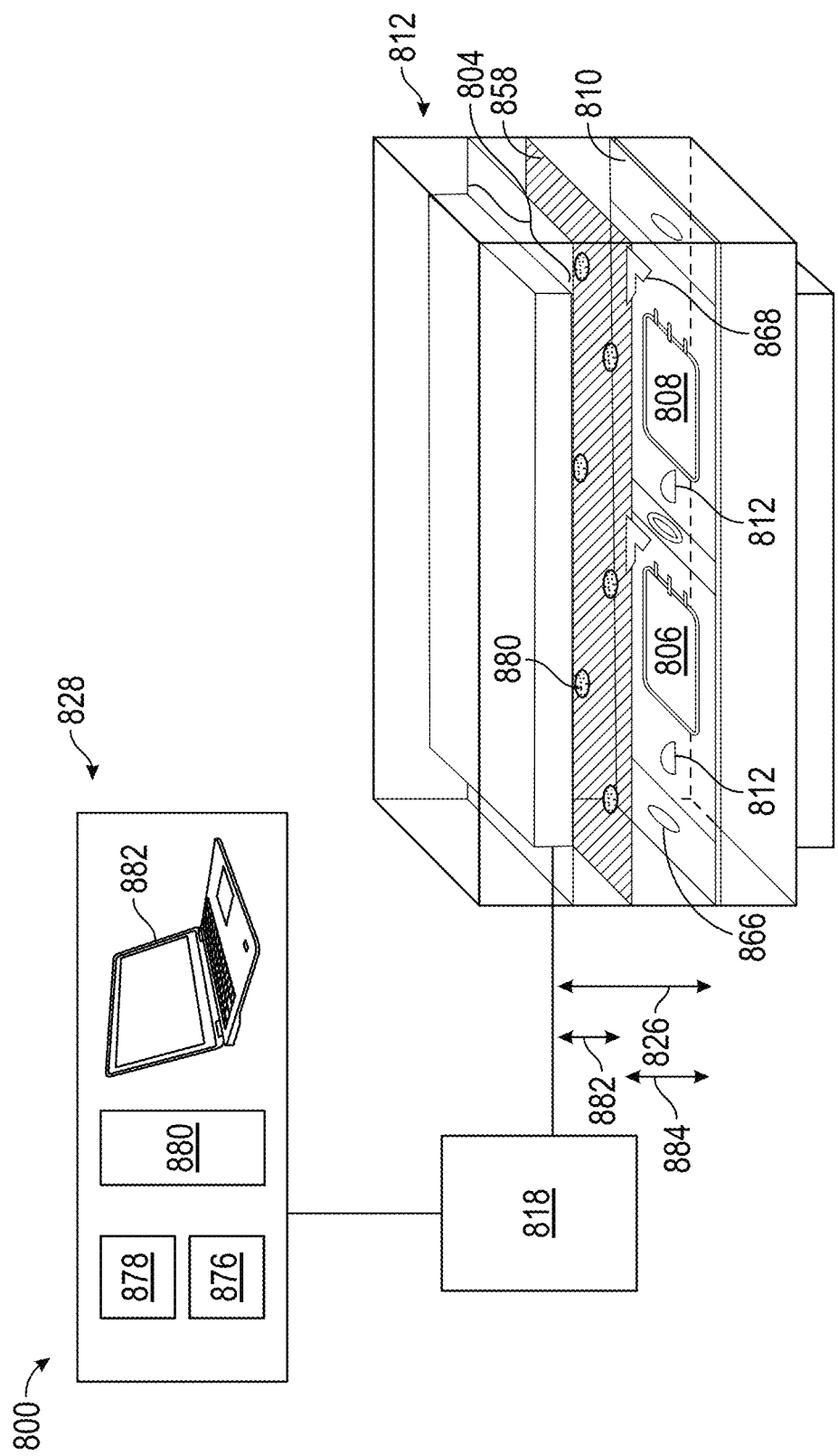

FIG. 8A shows a perspective view of an exemplary system 800 for treatment of one or more biological fluids 806 and 808 comprising a light source array 804 positioned in treatment chamber 812. Light source array 804 faces a platform 810 for biological fluids. Light source array 804 may be thermally coupled to heat exchanger 816. Treatment chamber 812 may include platform 810 positioned under light source array 804, the platform configured to hold one or more biological fluids 806 and 808. Treatment chamber 812, light source array 804, heat exchanger 816, and platform 810 may each be operatively coupled to control circuitry 818 that may adjust or set their respective parameters. FIG. 8B shows that exemplary system 800 may also include barrier (e.g., light barrier, protective barrier) 858 and various sensors 812, 866, 868, 880 in treatment chamber 812. In some embodiments, the barrier is transparent (e.g., substantially transparent, >95% transparent, >90% transparent, >80% transparent, >80% transparent) to light with a wavelength within 30 nm of the first peak wavelength (e.g., within 15 nanometers less than, within 15 nanometers greater than the first peak wavelength; no more than 15 nanometers greater than, no more than 15 nanometers less than the first peak wavelength). In some embodiments, the barrier is transparent (e.g., substantially transparent, >95% transparent, >90% transparent, >80% transparent, >80% transparent) to ultraviolet light, such as for example, light with a wavelength in the ultraviolet A spectrum. In some embodiments, the barrier is a light barrier (e.g., light filter) configured to reduce (e.g., minimize, attenuate, block) transmittance of light, such as for example light having a wavelength of less than the wavelength of light in the UVA spectrum. In some embodiments, the barrier is a light barrier configured to reduce transmittance of light having a wavelength of less than the wavelength of light in the UVB spectrum. In some embodiments, the barrier is a light barrier (e.g., light filter) configured to reduce (e.g., minimize, attenuate, block) transmittance of light having a wavelength at least 20 nm less than (e.g., at least 25 nm less than, at least 30 nm less than) the first peak wavelength and/or another peak wavelength (e.g., at least 20 nm less than the second, third, or fourth peak wavelength). In some embodiments, the barrier is a light barrier (e.g., light filter) configured to reduce transmittance of light having a wavelength at least 20 nm greater than (e.g., at least 25 nm greater than, at least 30 nm greater than) the first peak wavelength and/or another peak wavelength (e.g., at least 20 nm greater than the second, third, or fourth peak wavelength). Barrier 858 is positioned between array of light sources 804 and platform 810 (e.g., one or more biological fluids 806 and 808). Sensors 812, 866, 868 may be affixed to or positioned in platform 810. Sensors 880 may be affixed to (e.g., above or below) or positioned in barrier 858.

Light source array 804 may comprise an array of light source channels. Each light source channel of the light source array 804 may be configured to emit light of the various peak wavelengths discussed above and in the various arrangements of light sources and light source channels discussed above.

Light source array 804 and platform 810 may both be configured to translate relative to each other to increase or decrease distance 826 between them as in the translation discussed above. Platform 810 may be lowered to the bottom of treatment chamber 812, which may be raised from (e.g., by any structural base, including any components like sensors or circuitry), or flush with, an exterior bottom surface (e.g., floor, ground, desk, etc.). Lights source array 804 may be raised to the top of treatment chamber 812. In FIG. 8B, light source array 804, barrier 858, and platform 810 may all be configured to translate relative to each other to increase or decrease distances 826, 882, and 884 between any pair of: light source array 804, barrier 858, and platform 810. This translation may be effected by any number of actuators (e.g., electric motor, servo, etc.) controlled by control circuitry 818, which may separately control translation of light source array 804, barrier 858, and platform 810. In some embodiments, one or two of light source array 804, barrier 858, and platform 810 may be fixed in position in treatment chamber 812. For example, barrier 858 may be fixed in position in treatment chamber 812. As another example, barrier 858 and light source array 804 may be fixed in position relative to each other at a fixed distance 882 in treatment chamber 812 where platform 810 may be configured to translate to increase or decrease distances 826 and 884. As another example, barrier 858 and platform 810 may be fixed in position relative to each other at a fixed distance 884 in treatment chamber 812 where light source array 804 may be configured to translate to increase or decrease distances 826 and 882.

Figure 9:
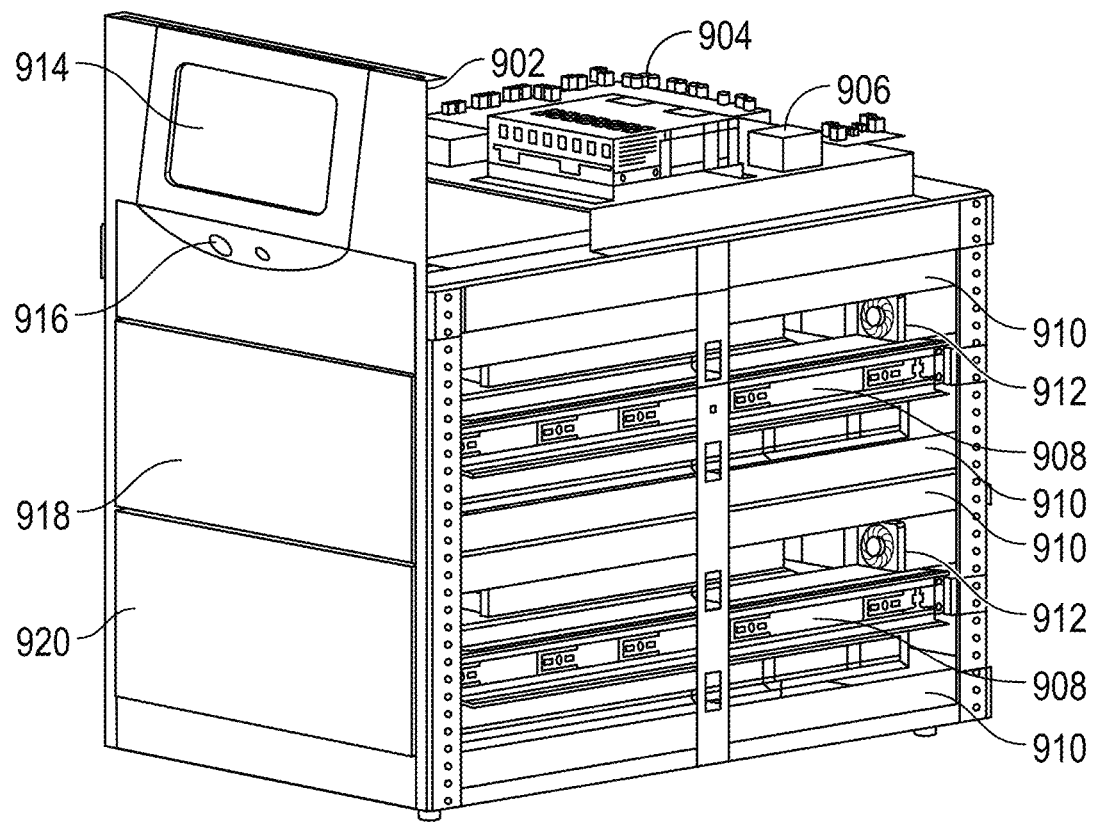
FIG. 9 illustrates an exemplary internal hardware layout for a system for treating a biological fluid according to examples of the disclosure.

As described above with respect to FIGS. 1-8(a and b), a biological fluid treatment device can include numerous components and systems that are required to work with another in a coordinated manner so as to safely and effectively treat biological fluids. While the examples above may illustrate an exemplary layout of the components used to treat one or more biological fluids in a device in which the two treatment chamber are oriented horizontally with respect to one another, as described above, the treatment chambers can also be oriented vertically with respect to one another. FIG. 9 illustrates another exemplary internal hardware layout for a system for treating a biological fluid according to examples of the disclosure. In the example of device 900, the treatment chambers can be oriented vertically with respect to one another such that when the device is treating two biological fluids simultaneously, the biological fluids can be disposed in the device one above the other.

The device 900 can include two separate treatment chambers 918 and 920, however in the example of device 900, the treatment chambers 918 and 920 can be oriented vertically with respect to one another. In one or more examples, each treatment chamber 918 and 920 can include one or more platforms (e.g., drawers) and associated trays 908 that are configured to carry a biological fluid (e.g., in a container) and allow for the biological fluid to be accessible by a user who can remove and/or place the biological fluid within the device. In one or more examples, each platform (e.g., drawer) 908 can be configured with an agitator (e.g., motor, servo), such as for example, an integrated agitator so that any biological fluid carried on the platform (e.g., drawer, and associated tray) 908 can be agitated during treatment so as to distribute (e.g., evenly distribute) the biological fluid and/or a pathogen inactivation compound in (e.g., in admixture with) the biological fluid.

In one or more examples, each treatment chamber 918 and 920 can also include one or more light engine components 910. In one or more examples, the light engine components 910 of each treatment chamber 918 and 920 can include one or more arrays of light sources (e.g., UV light sources) that are configured to deliver a desired amount of light (e.g., UV light) to a biological fluid positioned on or in each of the treatment chambers.

In one or more examples, and as discussed in further detail below, the device can include a control system board (CSB) 904 that is configured to coordinate the operation of one or more safety-critical components of the device. In one or more examples, a safety-critical component can refer to one or more components of the device that interact with the biological fluid being treated, and whose operation if done incorrectly can jeopardize the safety and efficacy (e.g., meeting required specifications) of the treatment process on the biological fluid. In one or more examples, the CSB 904 can be configured to communicate with and issue commands to each of the safety-critical components (described in further detail below) using a domain-specific customized communications protocol configured to protect the safety-critical components from being accessed by a malicious user, and configured to allow the device to be both modular and scalable with minimal disruption to the operation and/or maintaining regulatory compliance of the device. In one or more examples, the CSB 904 can be configured to communicate with and control the operation of the platform/tray/drawer 908 and the light engine components 910, inter alia, as these components directly interact with the biological sample and incorrect operation of these components could jeopardize the safety and efficacy of the treatment process. In one or more examples, the CSB 904 can also be configured to operate one or more fans 912 so as to pull air from the front of the device to the rear of the device in order to cool the device and biological fluid being treated, and prevent any overheating. In addition to controlling each of the components, the system CSB 904 can be configured to assess results from each of the components, which in one or more examples can be continuously communicated to it. The CSB 904 can be configured to use the results to determine subsequent operating steps of the device, for instance to stop agitation or complete the treatment process.

In addition to the treatment chamber specific components described above, in one or more examples, the device 900 can include one or more components that are not dedicated to a particular treatment chamber but instead are configured to operate the entire device and thus are common for both treatment chambers. In one or more examples, the device 900 can include a User Interface Controller (UIC) 902 that can be configured to manage the operation of one or more components of the device 900. In one or more examples, UIC 902 can be configured to coordinate the operations of one or more non-safety critical hardware and software components (described in further detail below). For instance, and in one or more examples, UIC 902 can be configured to operate one or more graphical user interfaces that are displayed on display 914. The one or more graphical user interfaces can be configured to guide a user through the treatment process and receive input from a user to determine information about the biological fluid to be treated and well as any other information the device may need to perform the treatment process. In one or more examples, the display 914 can be implemented as a "touch display" in which the user can touch the surface of the display to enter any inputs or otherwise interact with the device during the treatment process.

In one or more examples, the UIC 902 can also communicate with and control a scanner (e.g., barcode scanner) 916. The scanner 916 can be configured to scan one or more sources of identifying information (e.g., barcodes) found on a container that holds the biological fluid and includes information pertinent to the identifying the biological fluid as well as other information needed to ensure proper treatment of the material.

Figure 10:
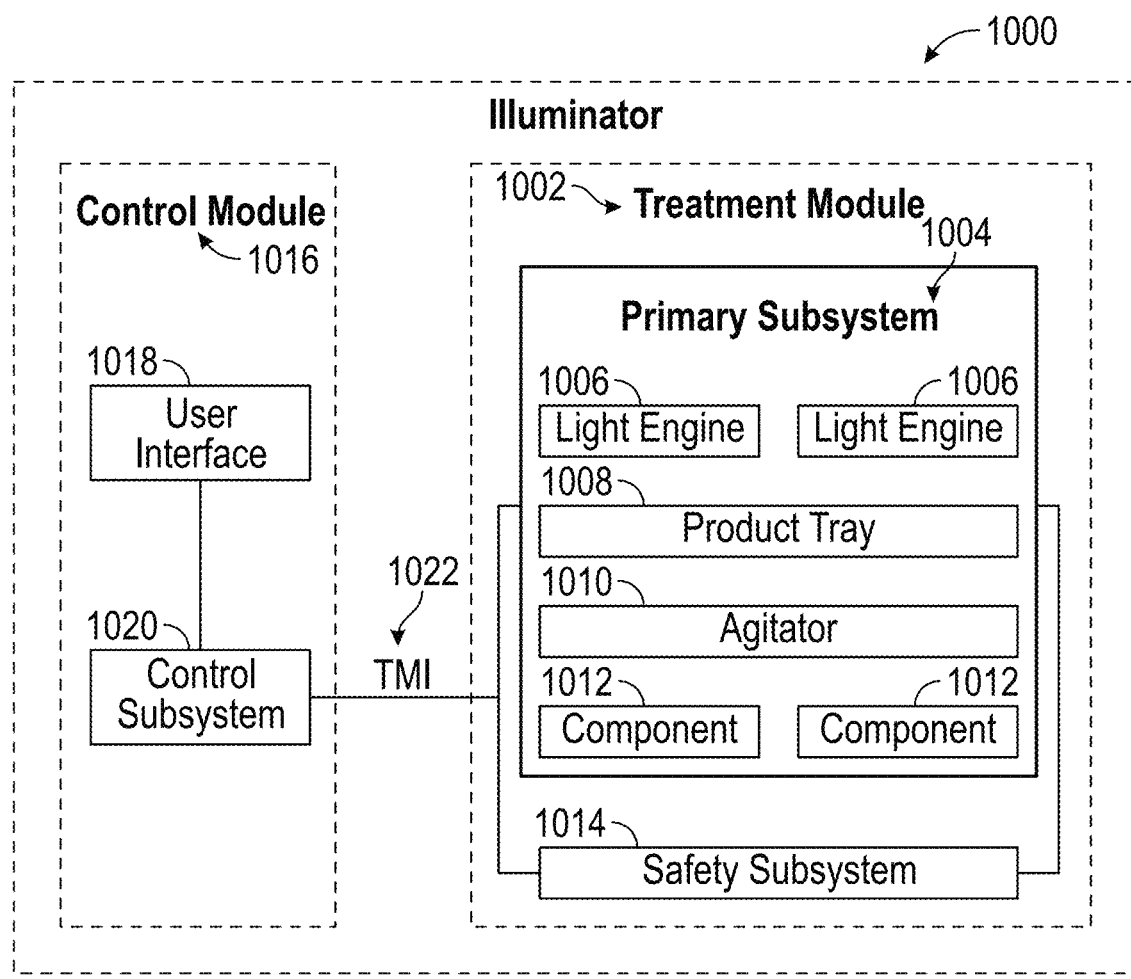
FIG. 10 illustrates an exemplary system diagram of an illuminator system for treating biological fluids according to examples of the disclosure.

FIG. 10 illustrates an exemplary system diagram of an illuminator system for treating biological fluids according to examples of the disclosure. In or more examples, the biological fluids treated by the system 1000 can include one or more of platelets, plasma, blood, and a blood product. As described above with respect to FIGS. 1-3 the device can treat a biological fluid by exposing the fluid to illumination with light (e.g., ultraviolet light, one or more light waves), such as in or more examples having wavelengths in the ultraviolet-A (UVA) spectrum. In order to treat the fluids using light, the device can be configured to deliver light (e.g., ultraviolet light, UVA light) to the biological fluid at specified intensities for a determined time period for the purpose of pathogen inactivation.

In one more examples of the disclosure, the system 1000 can include a control module 1016 and a treatment module 1002. In one more examples of the disclosure, the treatment module 1002 can include two subsystems: (1) a primary subsystem 1004 and a safety subsystem 1014. In one more examples of the disclosure, the primary subsystem 1004 can include the components and systems that carry out the light treatments (e.g., UVA light treatments), while the safety subsystem (described in detail below) can include components and systems that are configured to monitor the activities performed by the primary subsystem 1004.

In one more examples, the primary subsystem 1004 may contain one or more light engines 1006 that include the light source(s) (e.g., light source array(s)) for treating the biological fluid. Each light engine 1006 may include one or more light sources that can be configured to emit variable intensity of light (e.g., UVA light) and are positioned within the device so that when the light source is emitting, the biological fluid within the device is exposed to the light (e.g., light waves) emanating from the light source. In some examples of the disclosure, the biological fluid may be contained within a container (e.g., bag), and can be positioned within the device, such as for example on a platform, so that it can be exposed to the light (e.g., light waves) emanating from the light source.

The primary subsystem 1004 may also include one or more chambers (not shown) to receive treatment containers (e.g., bags) containing the biological fluid to be treated. The treatment container may be placed on a platform (e.g., product tray) 1008 within a treatment chamber. Each treatment chamber may have one or more light engines associated with it. For example, each chamber may receive light (e.g., UVA light) from one or multiple light engines 1006 to treat the biological fluid in the treatment container within the treatment chamber. In one more examples, treatment may be simultaneously performed on multiple treatment containers (e.g., bags) in multiple light chambers.

In some examples, the primary subsystem may include an agitator 1010. The agitator 1010 may be used to agitate the contents of the treatment container to distribute (e.g., evenly distribute) the biological fluid and/or a pathogen inactivation compound in (e.g., in admixture with) the biological fluid. The primary system may further contain miscellaneous components 1012 to perform various other functions that aid the treatment process. These functions may include, but are not limited to, one or more sensors (e.g., to detect light, light intensity, light dosage), detection of placement of the treatment container and marking mechanisms to demonstrate treatment has occurred on a particular treatment container.

In some examples of the disclosure, the safety subsystem 1014 within the treatment module 1002 may be used to monitor the treatment activities occurring in the primary subsystem 1004. The safety subsystem 1014 functionalities may include, but are not limited to interlocks, lockouts, hardware and software watchdogs and the like.

In some examples, illuminator system 1000 may contain a control module 1016 which may enable a user to make a treatment request and interact with the illuminator system 1000. In some examples, the control module 1016 may be physically separate from the illuminator system 1000. When physically separate, the control module 1016 may be connected to illuminator system 1000 through wires or wirelessly using a pre-determined wireless communication standard such as, for example, Bluetooth or WiFi. In some examples, one control module 1016 may be associated with multiple systems like illuminator system 1000.

In one or more examples of the disclosure, the control module 1016 may include a user interface 1018. The user interface 1018 may be a display that enables the user to interact with the illuminator system 1000. In one or more examples, the user interface 1018 can be implemented as an LED display with a touch screen interface that utilizes user selectable buttons, icons, and text so as to facilitate user interaction with the device. The user interface may include input-output devices like a touch pad, a keyboard, a mouse, a camera to read bar codes etc.

In one more examples of the disclosure, the system 1000 can include a common interface 1022. In some examples, the system 1000 is an electronic device for treating a biological fluid and the common interface 1022 is a treatment interface of the electronic device.

In some embodiments, the common interface 1022 is communicatively coupled to the control module 1016 (e.g., control subsystem 1020 of the control module 1016), the primary subsystem 1004, and the safety subsystem 1014.

The common interface 1022 can be configured to provide a communication pathway between the control module 1016 and the primary subsystem 1004 or the safety subsystem 1014. In some embodiments, communications between the control module and a subsystem is caused by an input to the user interface 1018. In some embodiments, communication between the control module and a subsystem is caused by an introduction of a subsystem or a component into the illuminator system (e.g., a light engine is installed into the system).

The modules and components and systems above can each include various components associated with their functionality. These components can be arranged in a system architecture that can allow for those components to be coordinated with one another so as to facilitate effective and efficient treatment of the one or more biological fluids.

Figure 11:
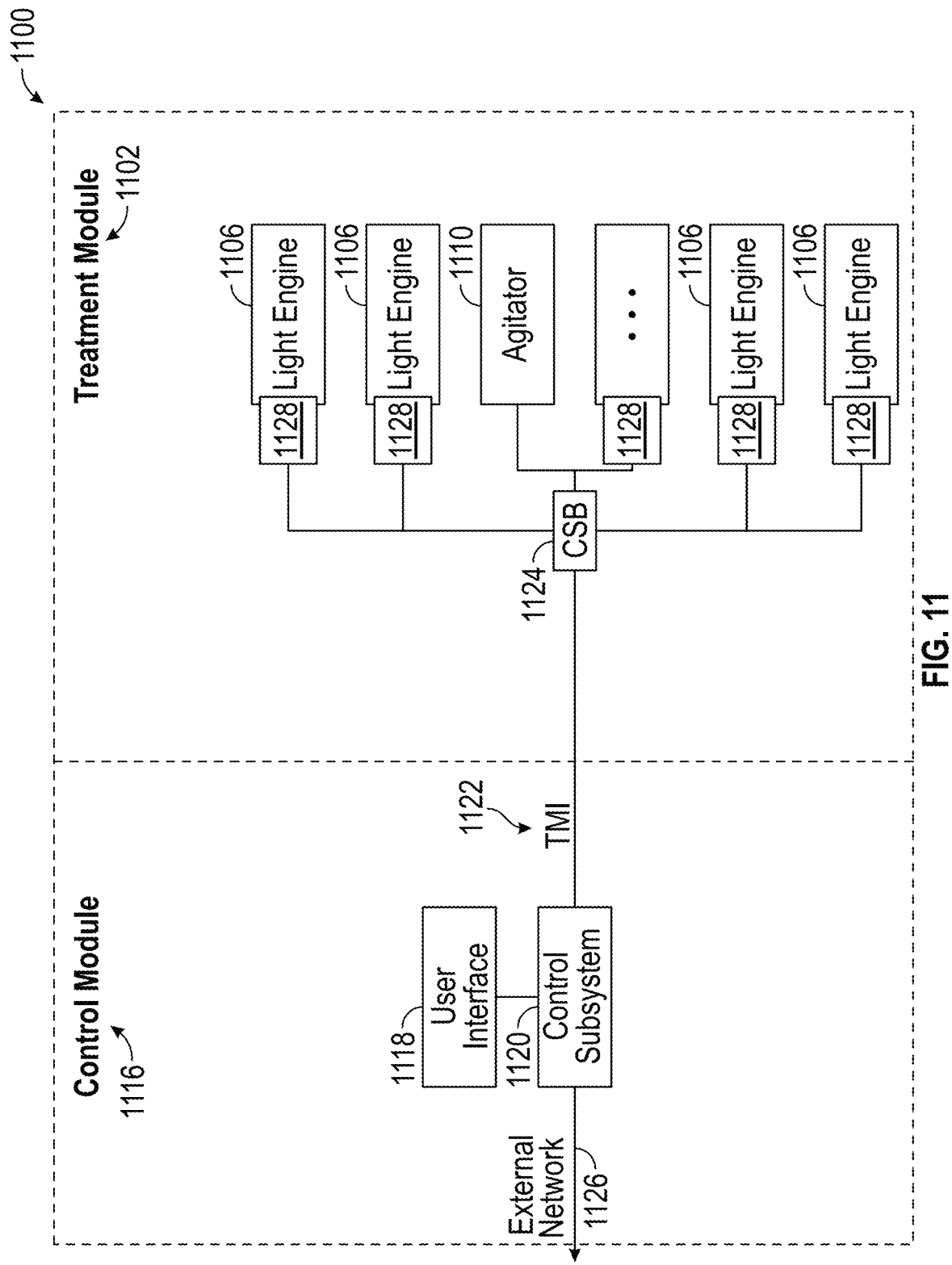
FIG. 11 illustrates an exemplary component architecture of an illuminator system for treating biological fluids according to examples of the disclosure.

FIG. 11 illustrates an exemplary component architecture of an illuminator system for treating biological fluids according to examples of the disclosure. In some examples of the disclosure the system architecture 1100 can include a control module 1116 and a treatment module 1102. The control module 1116 may include a control subsystem 1120, which may perform various functions. For example, the control subsystem 1120 may manage the graphic icons, screen transitions, button presses and other user interactions at the user interface 1118. It may print records of treatments that have occurred. It may act as a communications manager by interacting with a network external to the illuminator system 1100, such as for example, through Ethernet. In one or more examples, the control subsystem 1120 may also act as a data manager by maintaining a database of treatments that have occurred. In one or more examples, the control subsystem 1120 can also act as an event log manager by recording different events that occur (e.g., inside and/or outside) the illuminator system 1100. These events may include, but are not limited to, normal and abnormal environmental conditions, alarms, malfunctions and the like. In one or more examples, the controller may be a CPU or a microprocessor, and may include volatile and non-volatile memories.

In one or more examples, the control subsystem 1120 may enable communication between the control module 1116 and the outside network through a port (e.g., Ethernet port) 1126. For example, any devices external to the illuminator system 1100 can be connected to the control subsystem 1120 through port 1126. These devices may include, but are not limited to, an external personal computer, an external blood management system to transmit data in and out of illuminator system 1100 and the like. For example, a blood management system may gather reports from the illuminator system 1100. It may also transmit software and data into illuminator system 200 to perform different control functions. These functions may include, but are not limited to, programming illuminator system 1100 with different treatment profiles and user information, performing maintenance and health checks (e.g., diagnostics) of illuminator system 1100, and the like.

In one or more examples, the control module 1116 can be isolated from the treatment module 1102 with the help of a common interface 1122 (described in further detail below). For example, such isolation may help physically separate the critical functionality in the treatment module 1102 from the non-critical functionality in the control module 1116. In one or more examples of the disclosure the isolation between critical and not critical components may enable putting safety critical software and hardware that requires more stringent testing in treatment module 1102, and non-safety critical software and hardware that requires less stringent testing in control module 1116. In this way, the impact engendered by a replacement or modification to non-critical components to critical components of the device can be minimized.

In some embodiments, the common interface enables communication between the control module 1116 and the treatment module 1102 through the use of a predefined domain specific communication protocol. For example, the control subsystem 1120 (which can, in one or more examples be implemented as a controller) in the control module 1116 may communicate with a separate controller 1124 in the treatment module 1102.

In one or more examples, the control subsystem 1120 can be communicatively coupled to one or more non-safety critical components located in the control module 1116 and can also be communicatively coupled to the treatment module 1102 via controller 1124. Controller 1124 in the treatment module 1102 can be communicatively coupled to one or more safety critical components such as the light engine 1128 and agitator 1110 and can also be communicatively coupled to the control subsystem 1120 of the control module 1116.

In one or more examples, the control subsystem's 1120 only interface with the components of the treatment module 1102 can be through the controller 1124, while the controller 1124's only interface with the components in the control module 1116 can be through the control subsystem 1120. In this way, isolation between the non-safety critical component in the control module 1116 and the safety-critical components in the treatment module 1102 can be maintained. By maintaining this isolation through the use of two separate controllers, the impact caused by future changes to the components (i.e., change to or expansion of components) within the control module 1116 to the treatment module 502 can be minimized. Thus, changes in the control module 1116 may not require having to engage in burdensome retesting of components in the treatment module 1102 that have to pass regulatory scrutiny. Furthermore, by using a predefined domain-specific communications protocol 1122 to facilitate communications between the control subsystem 1120 and the controller 1124, further isolation between the non-safety critical components in control module 1116 and treatment module 1102 can be further maintained. The domain-specific interface protocol 522 used to communicate between control subsystem 1120 and controller 1124 can mean the way that the two modules 1116 and 1120 will remain consistent despite any changes in the components that make up control module 1116 and treatment module 1102.

In one or more examples, the controller 1124 may perform the safety related functions in the treatment module 1102. For example, the controller 1124 may monitor that the illuminator system 1100 is handled in a safe and proper manner and may implement an interlock or lock out mechanism when unsafe or improper conditions are detected. The controller 1124 may also implement alarms programmed to indicate errors that occur during the treatment process and indicate alarm information to the user through the user interface 1118. In some embodiments, the controller 1124 may also perform treatment tasks by managing the different components in the illuminator system 1100 according to a particular treatment profile. For example, the controller 1124 may control how much light energy (e.g., UVA energy) the biological fluid (e.g., treatment bag containing the biological fluid) is exposed to by controlling the on-off times of the light engines 1106 and the intensity of the light. In some examples, the controller 1124 may also control the wavelength of light emitted by the light engines and/or the speed of the agitator 1110. In some embodiments, the controller 1124 may be a single board computer or a custom Printed Circuit Board with a processor. The controller 1124 may include volatile and non-volatile memories.

In one or more examples of the disclosure, the illuminator system 1100 may include one or more smart components 1128. These smart components 1128 can include components like the light engines 1106, controller 1124, user interface 1118, control subsystem 1120, but with inbuilt computing hardware that is independent to each component. Each smart component's computing hardware may be programmed to perform functions that are unique to that component. For example, the computing hardware in controller 1124 may execute algorithms to manage interactions between all the components to carry out the treatment process. In some embodiments, the light engine 1106 smart component may have an algorithm for monitoring the light (e.g., UV) energy delivered and adjusting treatment times and dose rates. Additionally, the light engine 1106 may be able to take directions and commands from the controller 1124. In some embodiments, the computing hardware in smart components 1128 may be implemented using a custom Printed Circuit board, an FPGA, an ASIC and may include volatile and non-volatile memories.

In one or more examples of the disclosure, the illuminator system 1100 may include one or more sensors (not shown). For example, the light engine 1106 may include a light sensor (e.g., photodiode) to detect the amount (e.g., total dose) of light (e.g., light energy) emitted by the light source(s) (e.g., exiting the LEDs) in the light engine 1106 and/or the amount of light (e.g., light energy) delivered to a biological fluid, e.g., in a treatment container. Other examples of sensors may include, but are not limited to proximity sensors, weight sensors, air sensors, temperature sensors and the like.

In some examples, the system 1100 is an electronic device for treating a biological fluid and the common interface 1122 is a treatment interface of the electronic device. In some examples, a control module (e.g., control module 1016, control module 1116) of the system includes a first controller and a second controller. The first controller can be communicatively coupled to a plurality of non-safety critical components, such as the ones described herein, and the second controller can be communicatively coupled to a plurality of safety critical components, such as the ones described herein, through the treatment interface.

In some embodiments, in response to communicatively coupling the plurality of non-safety critical components to the treatment interface and communicatively coupling the plurality of safety-critical component to the treatment interface, the system detects, with the control module, presences of the plurality of non-safety critical component and the plurality of safety-critical component in the electronic device.

In some examples, the system can transmit first messages associated with the non-safety critical components between the first controller and the non-safety critical component through the treatment interface, and the system can transmit second messages between the second controller and the safety-critical component through the treatment interface. In some embodiments, the first and second messages are based on a domain-specific interface language. For example, the domain-specific interface language is TCP/IP. In some embodiments, in response to receiving a message, the controller module or the component may send a response (e.g., message accepted, message rejected, message missing information, receiver is busy) to the sender to acknowledge receipt of the respective message.

In some examples, the system determines states of the non-safety critical components based on the first messages and states of the safety critical components based on the second messages. For example, the states can be one or more of "uninitialized," "initializing," "ready," "running," "calibrating," "shutting down," "servicing," and "fault." It is understood that the states are not limited to the ones described herein.

In some examples, the message may include a message header and message data. The message header can include information associated with: one or more commands, a transaction number, message type, and message size. The message data can include information associated with one or more of states described herein.

In some embodiments, the message can include information about the system. For example, the information about the system can include a treatment dosage associate with a biological fluid being treated, a maximum treatment time of the biological fluid, a maximum hold time after the treatment completes, a data update interface (e.g., how often the system is being informed about treatment progress), speed of a component (e.g., agitator current speed in Hz). It is understood that the listed information are exemplary and are not limiting. In some embodiments, the information in the message are parameters defined by a user (e.g., information derived from user defined treatment parameters).

In some examples, the message can include information about a treatment. For examples, the information about a treatment can include treatment elapsed time, dosage applied, chamber temperature, biological fluid temperature, and speed of a component (e.g., agitator current speed in Hz). It is understood that the listed information are exemplary and are not limiting.

In some examples, the message can include information to cause the system to cancel a run (e.g., stop treatment). In some examples, the message can include information to notify the system that a run has completed (e.g., treatment has finished) and data (e.g., statistics) associated with the completed treatment.

In some embodiments, the message can be associated with servicing of the system. In some examples, the message can be a request to begin a service on the system. In some examples, the message includes information about a current service (e.g., maintenance) being performed on the system. In some examples, the message includes information about a completed service (e.g., a notification, service log).

In some embodiments, the message can be associated with system shutdown (e.g., a request to shut down the system, a request to shut down the system at a specific time). In some embodiments, the message can be associated with a system fault (e.g., identification of a faulty component, instruction for fault recovery, log associated with the fault). In some embodiments, the message can be associated with system calibration (e.g., transfer of a calibration file, transfer of a configuration file). In some embodiments, the message can be associated with a version of a subsystem or a component (e.g., interface version, firmware version, OS version, BIOS version, hardware version, component version, subsystem serial number). For example, messages associated with subsystem or component versions can ensure the system's safety, reliability, or compatibility requirements are up-to-date.

In some examples, the non-safety critical components or the safety critical components can change states. For example, a non-safety critical component or a safety critical component is in a first state. The system can change the state (e.g., in response to user input) of the non-safety critical component or the safety-critical component from the first state to a second state. In some examples, in response to the changing the state, the system sends, from of the non-safety critical component or the safety-critical component to the control module through the common interface, a second message (e.g., different from the first message). In some embodiments, the system receives, at the first controller or the second controller, the second message, and in response to receiving the second message, the system determines a second state of the treatment component.

In some examples, power is provided to the system and the presences of the plurality of non-safety critical component and the plurality of safety-critical component are detected in response to the providing of power to the system. For example, during power on and system initialization, the presences of these components are detected.

In some examples, in response to power being provided to the system, the system assigns local network addresses (e.g., IP addresses, MAC addresses) and ports (e.g., TCP ports) to the plurality of non-safety critical components and the plurality of safety-critical components. In some embodiments, the local network addresses and the ports are based on a domain-specific interface language. For example, the local addresses can be IP addresses or MAC addresses, and the local ports can be TCP ports.

Figure 12:
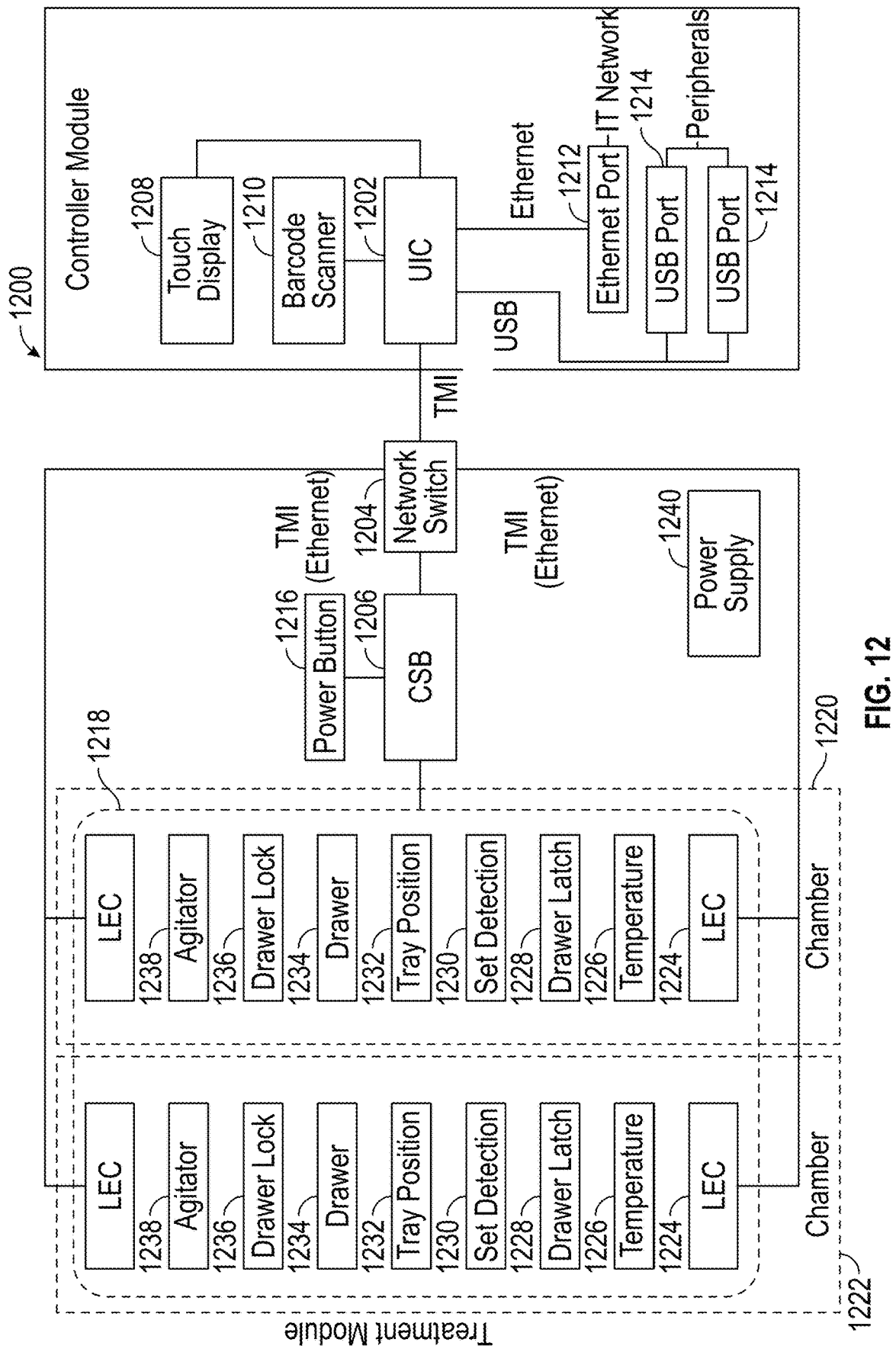
FIG. 12 illustrates an exemplary block diagram of a system for treating biological fluids according to examples of the disclosure.

FIG. 12 illustrates an exemplary block diagram of a system for treating biological fluids according to examples of the disclosure. The example system 1200 of FIG. 12 can serve as an additional example system diagram with respect the example provided above with respect to FIG. 11. In one or more examples, the system 1200 can include a user interface controller 1202 that can interface with one or more non-safety critical components of the device. In one or more examples the non-safety critical components can include a display (e.g., touch display) 1208, a scanner (e.g., barcode scanner) 1210, an Ethernet port 1212 and one or more USB ports 1214. The non-safety critical components can refer to components within the system 1200 that do not directly interact with the one or more biological fluids being treated by the device, and whose operation does not have a substantial effect on the safety and efficacy of the treatment process.

In one or more examples, the UIC 1202 can control and interact with one or more components of the system that are accessible by an external user of the device. For instance, in one or more examples, the UIC 1202 can interact with a touch display 1208 that can be configured to display one or more graphical user interfaces and is configured to receive one or more touch inputs from a user. In one or more examples, the UIC 1202 can control and interact with one or more barcode scanners 1210 that can be configured to scan one or more barcodes associated with a biological fluid (e.g., on a container associated with the biological fluid) and that can contain identifying information about the biological fluid. In one or more examples, the UIC 1202 can interact with an Ethernet port 1212 that can be configured to allow for the device to be connected to an external computing network (such as the internet or an enterprise computing system) so that the device can be controlled or accessed externally by a computer connected to the device via the Ethernet port 1212. In one or more examples the UIC 1202 can be configured to control and interact with one or more Universal Serial Bus (USB) ports 1214. The USB ports 1214 can allow for external devices such as a mouse or keyboard to be connected to the system 1200.

In one or more examples, the UIC 1202 can interact with one or more externally facing components (i.e., components that can be controlled by a user or device that is not part of the system) while not allowing the user or device to directly control one or more safety-critical components 1218 of the device. As will be described in detail below, the UIC 1202 can communicate with a control system board (CSB) 1206 that can be configured to receive commands from the UIC 1202 and convert those commands into one or more operations that are performed by one or more safety-critical components 1218.

In one or more examples of the disclosure, the system 1200 can include a network switch 1204 that can route transmissions between components of the system by using packet switching to receive and forward data to a particular component in the system. In one or more examples, the network switch 1204 can be configured to receive one or more packets (containing commands or information) from the UIC 1202 to the CSB 1206. For instance, the UIC 1202 can receive one or more inputs from an external user via the touch display 1208 and then can send those commands to the CSB 1206 via the network switch 1204 so that the CSB 1204 can control the safety-critical components of the device based on the user's inputs. In one or more examples, the network switch 1204 can also receive one or more packets from the CSB 1204 and can route the one or more packets to one or more safety-critical components 1218 (associated with a treatment module which can include both treatment chambers 1220 and 1222 so as to operate the safety-critical components for treatment of the biological fluids within the treatment chambers 1220 and 1222.

As briefly described above, each of the treatment chambers 1220 and 1222 can include one or more safety-critical components 1218. The safety-critical components 1218 can refer to the sensors and hardware used by the device to treat the one or more biological fluids. In one or more examples, the safety-critical components contained within each treatment chamber can include a Light Engine Components (LEC) module 1224, a temperature sensor 1226, a platform (e.g., drawer) latch sensor 1228, a set detection sensor 1230, a tray position sensor 1232, a platform (e.g., drawer)1234, a platform (e.g., drawer) lock 1236, and an agitator 1238.

In one or more examples, the LEC module 1224 can include one or more light sources (e.g., UV light sources) and light sensors and is configured to deliver light (e.g., UV light) to a biological fluid as well as monitor the amount of the light being delivered to and/or received by the biological fluid. In one or more examples of the disclosure, the safety-critical components 1218 can include an agitator that can be configured to agitate the contents of the treatment container to distribute (e.g., evenly distribute) the biological fluid and/or a pathogen inactivation compound in (e.g., in admixture with) the biological fluid. In one or more examples, agitator 1238 can include a mechanical agitator (e.g., motor, servo) configured to agitate a biological fluid or photoactive pathogen inactivation compound in (e.g., in admixture with) a biological fluid. In one or more examples, the safety critical components can include a platform (e.g., drawer) lock 1236 that is configured to lock or unlock the platform (e.g., drawer) of the treatment chamber (i.e., prevent the platform (e.g., drawer) from being opened) based on a command from the CSB 1206.

The safety-critical components 1218 can further include a plurality of sensors that are configured to provide the CSB 1206 with information regarding the operation of the device. In one or more examples, the temperature sensor 1226 can be configured to monitor the temperature of the system and/or the biological fluid and can be configured to transmit updates to the CSB 1206 indicating the temperature of the biological fluid and/or device. In one or more examples of the disclosure, the platform (e.g., drawer) latch sensor 1228 can be configured to detect whether a latch (e.g., lock) on the platform (e.g., drawer) of the device (described in detail above) is in an open or closed position, and can be configured to transmit a signal to the CSB 1206 indicating the position of the latch. In one or more examples, the set (e.g., processing set, fluid processing set) detector sensor 1230 can be configured to detect the presence of a container (e.g., bag) containing a biological fluid on or in a platform (e.g., drawer, associated tray) and/or within the treatment chamber and can be configured to transmit a signal to the CSB 1206 indicating the presence or lack thereof of the container (e.g., bag). In one or more examples of the disclosure, the tray position sensor 1232 can be configured to determine the presence of a tray and/or a position of a tray of the device (described in detail above), such as for example the presence of a tray and/or position (e.g., movement) of a tray within a platform (e.g., drawer), and can be configured to transmit a signal to CSB 1206 indicating the position of the platform/tray/drawer. In one or more examples, the platform (e.g., drawer) and/or associated sensor 1234 can be configured to determine a position of the platform (e.g., drawer) of the treatment chamber (e.g., determine if the platform (e.g., drawer) is in a closed position inside the treatment chamber) and can be configured to transmit a signal to CSB 120 indicating the position of the drawer. In one or more examples, a "tray" can refer to a removable portion or component of a platform that houses the biological fluid during treatment, and which may be transparent (e.g., fully or partially transparent, so as to allow light to pass through it) on one or more surfaces, such as for example the floor (e.g., bottom) of the tray. In one or more examples, the term "drawer" can refer to the platform and associated frame that holds the tray, and that can secure an agitator motor. In one or more examples, the drawer can be configured to present the tray to the operator. In one or more examples, the tray can be agitated during treatment, such as for example by movement back and forth in a linear path within the platform (e.g., drawer).

In one or more examples of the disclosure, the CSB 1206 can be configured to communicate directly with a power button of the device so as to turn the device on or off, and subsequently issue commands to each of the safety-critical components 1218 to cease operation or begin operation. The system 1200 can also include a power supply 1240 that can be used to provide an electrical signal to each of the components in the system 1200 to power their operation.

As illustrated in FIG. 12, the system 1200 can include two separate controllers, UIC 1202 and CSB 1206, to control non-safety critical components and the safety critical components 1218 respectively. By including two separate controllers, the system 1200 can ensure that fraudulent or faulty operation of the device from external users or devices can minimally impact the operation of the safety-critical components 1218. To further isolate the safety-critical components, for the non-safety critical components, the UIC 1202 can be configured to communicated with the non-safety critical components in a first communications protocol, and the CSB 1206 can communicate with the safety critical components in a second communications protocol that is distinct from the first. In one or more examples, the system 1200 can further utilize a domain-specific communications protocol that is specific to the system to communicate with and command the safety-critical components 1218. In the example of FIG. 12, the domain-specific communications protocol can be referred to as a Treatment Module Interface (TMI) protocol.

In one or more examples, the TMI protocol can be configured such that the safety-critical components will only respond to commands sent from the CSB 1206. In this way, the UIC 1202 which is configured to control all of the externally facing components (i.e., components that can be accessed by an external user or device) cannot be used to directly control the safety-critical components 1218, thereby providing an added layer of security for the treatment process. Thus, in one or more examples, when a user enters an input into one of the non-safety critical components such as touch display 1208, and if the command requires action from one of the safety-critical components 1218, the command can be transmitted from the UIC 1202 to the CSB 1206 via the network switch 1204. In one or more examples, the network switch 1204 may be optional and not required. Once the CSB 1206 receives the desired action from the UIC 1202, it can generate one or more commands for the safety-critical component 1218 using the TMI protocol to operate those components according to the desired action registered by the UIC 1202.

In order to facilitate the above described interactions the TMI protocol, in one or more examples, can be configured to identify the sender/originator of any packets such that the receiver of a packet can determine whether the command issued from the CSB 1206. In one or more examples of the disclosure, the TMI protocol can be configured to only allow for commands originating from the CSB 1206 to act upon any the safety-critical components 1218. Thus, any component deemed safety-critical can be configured to only accept TMI packets from the CSB 1206 only.

In one or more examples, the TMI protocol can be configured as a custom communications interface that can serves as a message and command transport between the CSB 1206 and the components of the treatment module. The TMI can be configured to support safety and cyber-security (as described above) by separating non-safety and safety-critical functionality. In addition to supporting safety, the TMI protocol can further be configured to enable modularity of and scalability of the device, and also improve the reliability and testability of the device. In one or more examples, the TMI protocol can utilize a Ethernet, UDP/IP transport medium to relay communications that are written in the protocol.

Figure 13:
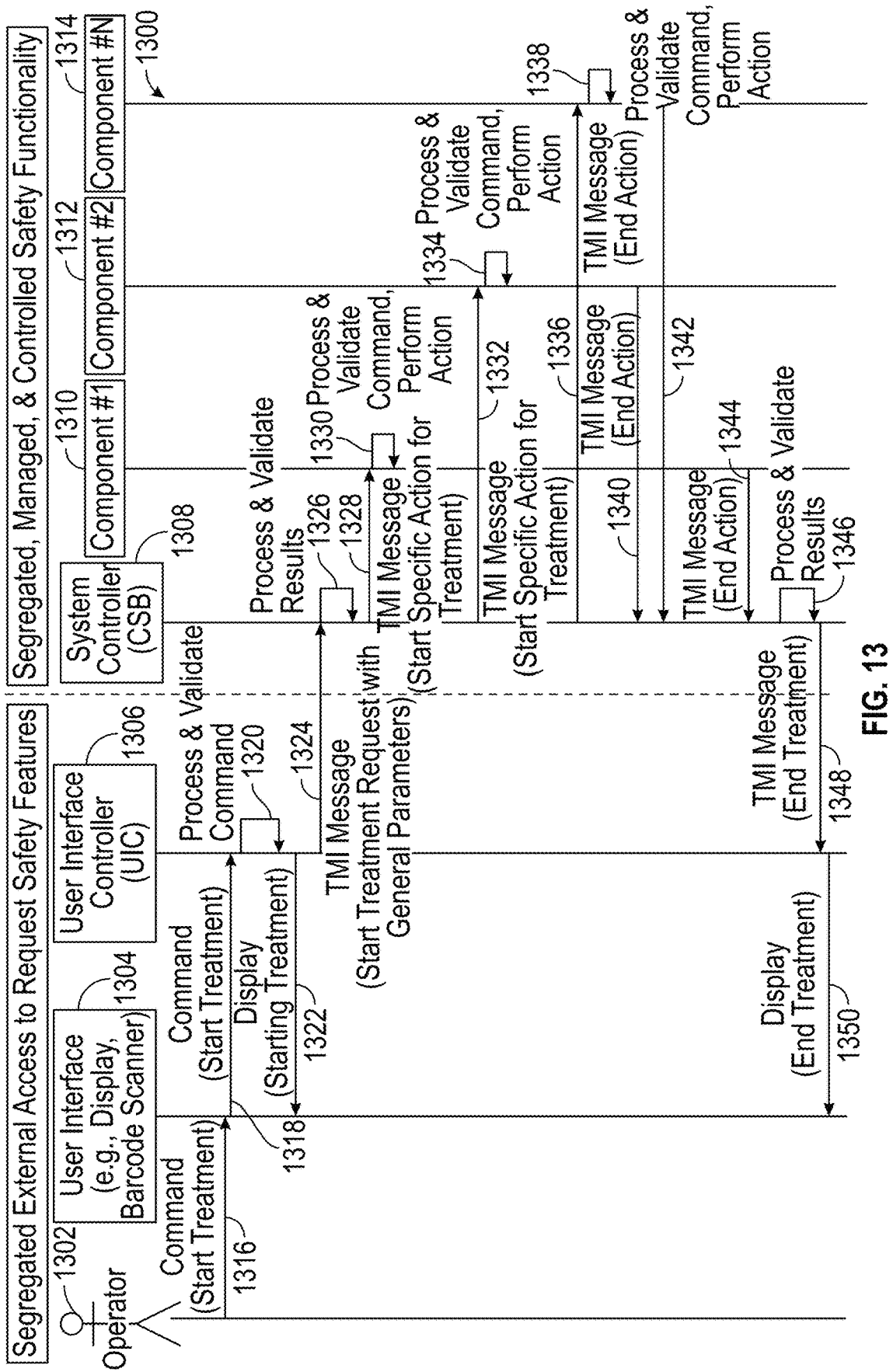
FIG. 13 illustrates an exemplary implementation of a domain-specific communications protocol according to examples of the disclosure.

FIG. 13 illustrates an exemplary implementation of a domain-specific communications protocol according to examples of the disclosure. The example diagram 1300 of FIG. 13 illustrates the process by which a command issued by an external user is translated to one or more commands that are used to operate the individual components of an electronic device for treating a biological fluid.

In one or more examples, the process shown in diagram 1300 can begin with a user 1302 who issues a command to the device to start treatment of a biological fluid. In one or more examples, the user 1302 can issue the command 1316 via a user interface 1304. The user interface 1304 can include a display (e.g., touch screen display), a voice recognition component, a motion detection component, keyboard, or any other device that can be configured to allow for the user to input its desired actions to the electronic device so that the device may act on those commands.

In one or more examples, once the user interface 1304 receives the command 1316 from the user 1302, the user interface 1304 can convert the user's command into a command 1318 that is specifically formatted to be compatible with a user interface controller (UIC) 1306 (described in detail above). The UIC 1306, upon receiving the command 1318, can process and validate the command as shown at 1320. If the command 1318 received by the UIC is successfully validated (i.e., the command is proper and in one or more examples is authenticated), then the UIC 1306 can transmit a signal 1322 to the user interface 1304, so that the user interface 1304 can provide a display to the user 1302 via the interface 1304 that the treatment was successfully initiated.

In one or more examples, after processing and validating the received command 1318, the UIC 1306 can generate and transmit a command 1324 formatted using the domain-specific TMI communications protocol that is configured to alert the system controller 1308 (described above with respect to FIG. 12) to the user's desired operation of the electronic device. In one or more examples, the command 1324 formatted in the TMI protocol can include information regarding the sender of the command 1324 (in this case the UIC 1306), and the system controller can be configured to accept only commands to initiate treatment sent by UIC 1306. When the system controller 1308 receives the TMI formatted message 1324 from the UIC 1306, the system controller 1308 can process and validate the command as indicated at 1326.

In one or more examples, once the system controller 1308 process and validates the TMI formatted message 1324 from the UIC 1306 at 1326, the system controller can generate and transmit one or more commands to each of the components 1310, 1312, and 1314 to initiate the treatment process on a biological fluid. In one or more examples, components 1310, 1312, and 1314 can represent the safety-critical components located in the treatment chambers of a device, which in one or more examples can include the light engine components, agitators, platform/tray/drawer locks, and sensors discussed in detail above with respect to FIG. 12. In one or more examples, the system controller can generate separate commands 1328, 1332, and 1336 to each of the components 1310, 1312, and 1314 that may be involved in the treatment of the biological fluid. In one or more examples, the commands 1328, 1332, and 1336 can be formatted using the domain-specific TMI communications protocol that is only known to the components within the electronic device. Furthermore, the commands 1328, 1332, and 1336 generated using the TMI communications protocol can include information regarding the origination of the command (in this case the system controller 1308), and each of the components 1310, 1312, and 1314 can be configured to only respond to the commands that are determined to originate from the system controller 1308.

In one or more examples, the system controller 1308 can generate a TMI message 1328 to a first component of the treatment chamber 1310 indicating the action that the component is to take and identifying the origination of the message. Once the first component 1310 receives the command 1328, it can process and validate the command at 1330 to ensure that not only is the command proper, but also that it originated from the system controller 1308. In the event that the component 1310 determines that the command 1328 is improper or that it is unable to determine that the command 1328 originated from the system controller 1308, the component can transmit a message to the system controller 1308 alerting it to the error (not shown). However, if the command is properly validated and authenticated, then in one or more examples, the component 1310 can perform the action indicated by the message 1328. Once the component 1310 performs the action, it can then generate a message 1344 that is also formatted using the TMI protocol that lets the system controller 1308 that the requested action has been performed.

In one or more examples, the system controller 1308 can generate a TMI message 1332 to a second component of the treatment chamber 1312 indicating the action that the component is to take and identifying the origination of the message. Once the second component 1312 receives the command 1332, it can process and validate the command at 1334 to ensure that not only is the command proper, but also that it originated from the system controller 1308. In the event that the component 1312 determines that the command 1332 is improper or that it unable to determine that the command 1332 originated from the system controller 1308, the component 1312 can transmit a message to the system controller 1308 alerting it to the error (not shown). However, if the command is properly validated and authenticated, then in one or more examples the component 1312 can perform the action indicated by the message 1332. Once the component 1312 performs the action, it can then generate a message 1340 that is also formatted using the TMI protocol that lets the system controller 1308 that the requested action has been performed.

In one or more examples, the system controller 1308 can generate a TMI message 1336 to a third component 1314 of the treatment chamber indicating the action that the component is to take and identifying the origination of the message. Once the third component 1314 receives the command 1336, it can process and validate the command at 1338 to ensure that not only is the command proper, but also that it originated from the system controller 1308. In the event that the component 1314 determines that the command 1336 is improper or that it unable to determine that the command 1336 originated from the system controller 1308, the component 1314 can transmit a message to the system controller 1308 alerting it to the error (not shown). However, if the command is properly validated and authenticated, then in one or more examples the component 1314 can perform the action indicated by the message 1336. Once the component 1314 performs the action, it can then generate a message 1342 that is also formatted using the TMI protocol that lets the system controller 1308 that the requested action has been performed.

While the examples of FIG. 13 illustrates a communications process for a device that includes three components 1310, 1312, 1314, the example can be readily applied to a device with any number of components without deviating from the methods and process described above with respect to FIG. 13. Thus, the components 1310, 1312, and 1314 are meant for illustrative purposes and should not be seen as limiting.

In one or more examples, once the system controller 1308 has received messages 1340, 1342, and 1344, from components 1310, 1312, and 1314, the system controller 1308 can process and validate the received messages at 1346, and can then generate and transmit a TMI formatted message 1348 to the UIC 1306 indicating that the treatment has ended (e.g., treatment has been completed). In one or more examples, upon receiving the message 1348 from the system controller 1308 indicating that the treatment has ended, the UIC can transmit a message 1350 (either in the TMI format or in another format understood by the display) to the user interface 1304, instructing the user interface to display one or more graphical user interface that indicate to the user that the treatment process has finished.

As demonstrated above with respect to the example of FIG. 13, the device can be configured to provide isolation between the components controlled by UIC 1306 and the components controlled system controller 1308 using the domain-specific TMI communications protocol. By configuring the TMI protocol such that the safety-critical components used to treat a biological fluid can only accept commands generated in the TMI protocol (which is only known internally by the device) and only accept commands generated by the system controller 1308, the chance that a malicious user or other external actor commanding the device without authorization is minimized. In one or more examples, the TMI communications protocol can further be configured to facilitate the introduction of new or replacement components in the treatment chambers, with minimal disruption to the device, as the system controller can be configured to detect new components and ensure that only it can issue commands to operate them.

In one or more examples, the TMI communications protocol can serve as a message and command transport between the controller 1308 and the components located within each treatment chamber. The TMI communications protocol can support safety and cyber security needs of the device by separating and isolating the safety-critical components from the non-safety critical components, enable modularity and scalability, and improve reliability and testability. In one or more examples, the TMI communications protocol can be configured using a state-based design that can reduce design complexity, reduce change for misuse, isolate errors amongst components, and report events in an efficient manner to the device. In one or more examples, the TMI communications protocol can utilize a commercial off the shelf transport protocol such and Ethernet or UDP/IP to transport the messages back and forth between the various components of the device.

Figure 14:
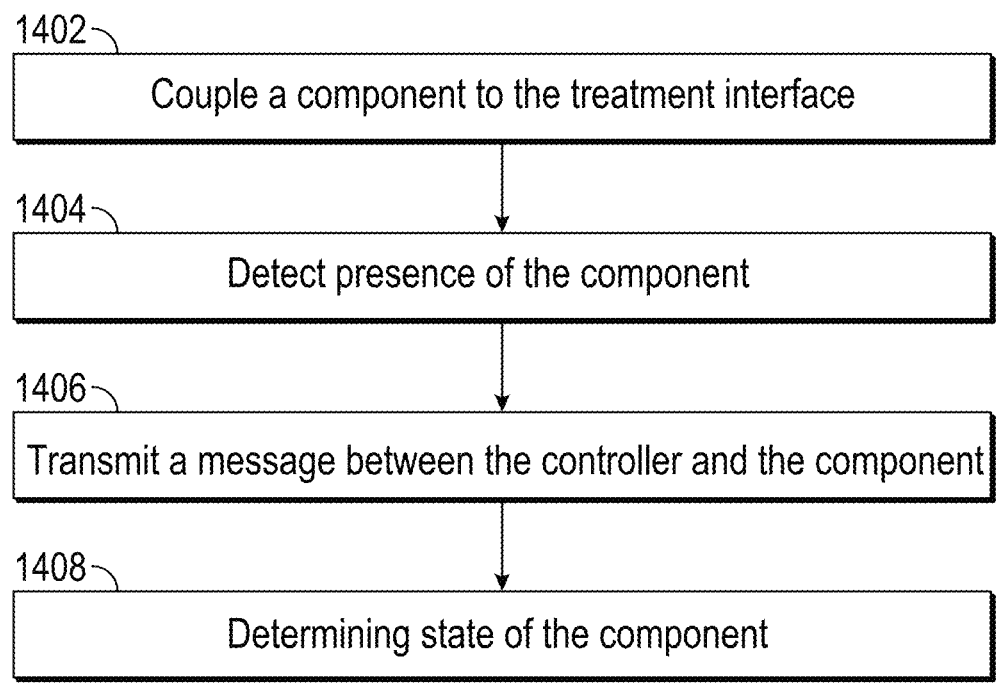
FIG. 14 illustrates an exemplary method of operating an exemplary system for treating biological fluids according to examples of the disclosure.

FIG. 14 illustrates an exemplary method 1400 of operating an exemplary system for treating biological fluids according to examples of the disclosure. In some examples, the method 1400 can be performed with the devices or systems disclosed herein.

The method 1400 includes coupling (step 1402) a non-safety critical component or a safety-critical component to the treatment interface. For example, with references to FIGS. 10 and 11, one of a non-safety critical component or a safety critical component is communicatively coupled to the common interface 1022 or 1122.

The method includes: in response to the coupling of the non-safety critical component or the safety-critical component to the treatment interface, detecting (step 1404), with the controller, a presence of the non-safety critical component or the safety-critical component in the electronic device. For example, with references to FIGS. 10 and 11, the presence of the non-safety critical component or safety critical component is a detected in response to the coupling performed in step 1402.

The method includes transmitting (step 1406) a message between the controller and the non-safety critical component or the safety-critical component through the treatment interface, the message based on a domain-specific interface language. For example, with references to FIGS. 10 and 11, a message, as disclosed herein, between the coupled component and the controller module is being transmitted.

The method includes determining (step 1408) a state of the non-safety critical component or the safety-critical component based on the message. For example, with references to FIGS. 10 and 11, a state, as disclosed herein, of the coupled component is determined based on the transmitted message in step 1406.

Although the common interface is described with respect to a system that includes a plurality of non-safety critical components and safety critical components, it is understood that the above description is also applicable to individual non-safety critical component or an individual safety critical component. For example, the system includes a control module, a non-safety critical component, a safety critical component, and a common interface (e.g., a treatment interface of an electronic device for treating a biological fluid). The interaction between the control module and the non-safety critical component or the safety critical component using the common interface can be substantially similar to the common interface interactions between the control module, the non-safety critical components, and the safety critical components described herein. For the sake of brevity, the interactions between the control module and the non-safety critical component or the safety critical component are not described. It is understood that these interactions are also include within the scope of the disclosure.

Figure 15:
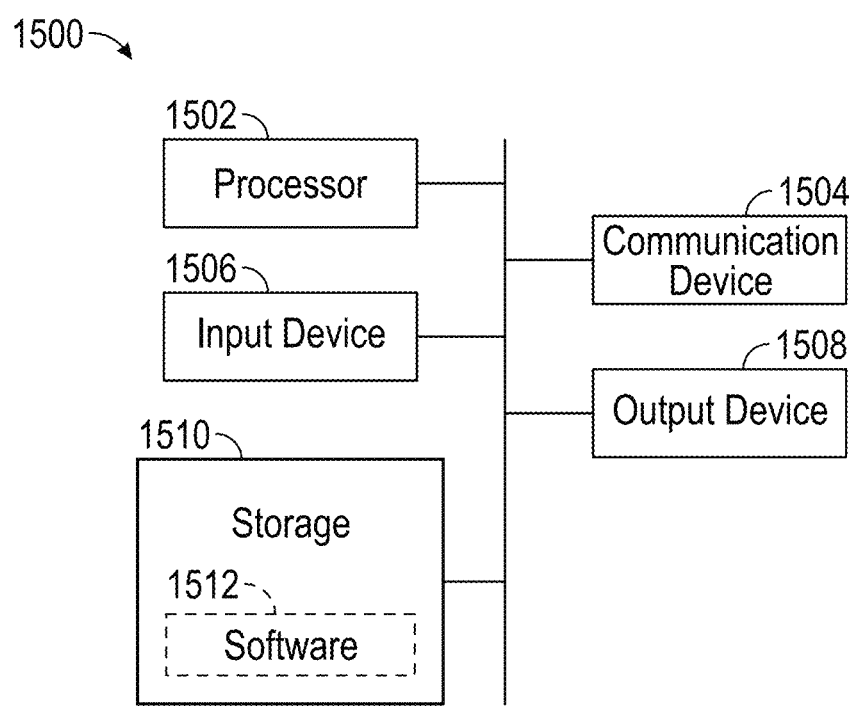
FIG. 15 illustrates an example of a computing device according to examples of the disclosure.

FIG. 15 illustrates an example of a computing device in accordance with one embodiment. Device 1500 can be a host computer connected to a network. Device 1500 can be a client computer or a server. As shown in FIG. 15, device 1500 can be any suitable type of microprocessor-based device, such as a personal computer, work station, server, or handheld computing device (portable electronic device) such as a phone or tablet. The device can include, for example, one or more of processors 1502, input device 1506, output device 1508, storage 1510, and communication device 1504. Input device 1506 and output device 1508 can generally correspond to those described above and can either be connectable or integrated with the computer.

Input device 1506 can be any suitable device that provides input, such as a touchscreen, keyboard or keypad, mouse, or voice-recognition device. Output device 1508 can be any suitable device that provides output, such as a touchscreen, haptics device, or speaker.

Storage 1510 can be any suitable device that provides storage, such as an electrical, magnetic, or optical memory including a RAM, cache, hard drive, or removable storage disk. Communication device 1504 can include any suitable device capable of transmitting and receiving signals over a network, such as a network interface chip or device. The components of the computer can be connected in any suitable manner, such as via a physical bus, or wirelessly.

Software 1512, which can be stored in storage 1510 and executed by processor 1510, can include, for example, the programming that embodies the functionality of the present disclosure (e.g., as embodied in the devices described above).

Software 1512 can also be stored and/or transported within any non-transitory, computer-readable storage medium for use by or in connection with an instruction execution system, apparatus, or device, such as those described above, that can fetch instructions associated with the software from the instruction execution system, apparatus, or device and execute the instructions. In the context of this disclosure, a computer-readable storage medium can be any medium, such as storage 1510, that can contain or store programming for use by or in connection with an instruction-execution system, apparatus, or device.

Software 1512 can also be propagated within any transport medium for use by or in connection with an instruction-execution system, apparatus, or device, such as those described above, that can fetch instructions associated with the software from the instruction-execution system, apparatus, or device and execute the instructions. In the context of this disclosure, a transport medium can be any medium that can communicate, propagate, or transport programming for use by or in connection with an instruction-execution system, apparatus, or device. The transport readable medium can include, but is not limited to, an electronic, magnetic, optical, electromagnetic, or infrared wired or wireless propagation medium.

Device 1500 may be connected to a network, which can be any suitable type of interconnected communication system. The network can implement any suitable communications protocol and can be secured by any suitable security protocol. The network can comprise network links of any suitable arrangement that can implement the transmission and reception of network signals, such as wireless network connections, T1 or T3 lines, cable networks, DSL, or telephone lines.

Device 1500 can implement any operating system suitable for operating on the network. Software 1512 can be written in any suitable programming language, such as C, C++, Java, or Python. In various embodiments, application software embodying the functionality of the present disclosure can be deployed in different configurations, such as in a client/server arrangement or through a Web browser as a Web-based application or Web service, for example.

In one aspect, an electronic device for treating a biological fluid, includes: a plurality of non-safety critical components; a first controller communicatively coupled to the plurality of non-safety critical components and configured to operate the plurality of non-safety critical components; a plurality of safety critical components, wherein the safety critical components comprise: one or more platforms, wherein each platform of the one or more platforms is configured to carry one or more biological fluids; one or more light engines, wherein each light engine is configured to illuminate the biological fluid; and one or more safety components; wherein the one or more safety components are configured to monitor the operation of the safety critical components; and a second controller communicatively coupled to the plurality of safety critical components and communicatively coupled to the first controller, wherein the second controller is configured to coordinate one or more operations involving the plurality of safety critical components; wherein the first controller and the second controller communicate with one another using a domain-specific interface language configured to isolate the plurality of non-safety critical components from the plurality of safety-critical components.

While specific components, configurations, features, and functions are provided above, it will be appreciated by one of ordinary skill in the art that other variations may be used. Additionally, although a feature may appear to be described in connection with a particular embodiment, one skilled in the art would recognize that various features of the described embodiments may be combined. Moreover, aspects described in connection with an embodiment may stand alone.

In some embodiments, any of the above described treatment systems and devices may be used to inactivate pathogen(s) in one or more biological fluids, including for example, biological fluids admixed with one or more pathogen inactivation compounds (e.g., photoactive pathogen inactivation compound, psoralen). In particular, any of the above described treatment systems and devices may illuminate a mixture of one or more pathogen inactivation compounds and a biological fluid, such as for example blood or a blood product (e.g., platelet compositions, plasma compositions and their derivatives), with light of certain wavelengths (e.g., ultraviolet light) to cause a photochemical reaction and inactivate pathogen(s), such as viruses, bacteria, parasites and other contaminants, such as for example, cell contaminants (e.g., leukocytes) that may be present in the biological fluid. In some embodiments, the pathogen inactivation compound targets nucleic acids to photochemically form adducts and/or cross-links. For example, a device of the present disclosure may be used in a method of treating a biological fluid comprising: providing a biological fluid in admixture with a photoactive pathogen inactivation compound (e.g., psoralen, amotosalen), and illuminating the biological fluid with ultraviolet light, such as for example, ultraviolet light with a first peak wavelength of from about 315 nm to about 350 nm (e.g., about 315 nm to about 335 nm, about 330 nm to about 350 nm, about 340 nm to about 350 nm, about 340 nm, about 345 nm) emitted by a set of one or more first light sources, wherein illuminating the biological fluid occurs for a duration and at an intensity sufficient to inactivate a pathogen in the biological fluid. In some examples, a device of the present disclosure may be used in a method of treating a biological fluid comprising: illuminating the biological fluid with ultraviolet light (e.g., UV-A, UV-B, UV-C) emitted by a set of one or more first light sources, wherein illuminating the biological fluid occurs for a duration and at an intensity sufficient to inactivate a pathogen in the biological fluid. In some embodiments, each of the one or more first light sources emits light having a full-width half-maximum (FWHM) spectral bandwidth of less than 20 nanometers. In some embodiments, each of the one or more first light sources is a light-emitting diode (LED).

The term "pathogen inactivation compound" means any suitable compound, such as a small organic compound, that can be used to inactivate a pathogen that may be present in a biological fluid, such as for example, blood or a blood product. A pathogen inactivation compound that is a "photoactive" or "photoactivated" or "photochemical" or "photosensitizer" compound is a suitable compound that requires some level of light in order to sufficiently inactivate a pathogen. Such compounds are preferred in the inactivation of pathogens in biological products as they provide control over the inactivation process. In some embodiments, the pathogen inactivating compound is a photoactive pathogen inactivating compound selected from the group consisting of a psoralen, an isoalloxazine, an alloxazine, a phthalocyanine, a phenothiazine, a porphyrin, and merocyanine 540. In some embodiments, the pathogen inactivating compound is a psoralen. In some embodiments, the pathogen inactivating compound is amotosalen (e.g., S-59). Such photoactivated or photochemical pathogen inactivation compounds as described herein may include, but are not limited to, psoralens, isoalloxazines, alloxazines, phthalocyanines, phenothiazines, and porphyrins, where these terms are understood to encompass a general class of compounds, i.e. the core compound and suitable derivatives thereof. For example psoralens or a psoralen generally describes the psoralen core compound and any derivative thereof (e.g., amotosalen), isoalloxazines or an isoalloxazine generally describes the isoalloxazine core and any derivative thereof (e.g., riboflavin), and so forth. Such derivatives comprise the core compound structure as well as additional substituents on the core. Descriptions of such compounds include any salts thereof.

The term "amotosalen" means the compound 3-(2-aminoethoxymethyl)-2,5,9-trimethylfuro[3,2-g]chromen-7-one and any salts thereof. The compound may also be referred to as 4'-(4-amino-2-oxa)butyl-4,5',8-trimethyl psoralen. Where the methods of the present disclosure include adding amotosalen HCl (the HCl salt of amotosalen), the removal of this compound from the biological fluid, such as for example a blood product (e.g., platelet composition, unit of platelets, plasma composition, whole blood composition, plasma composition) is not limited to the removal of amotosalen HCl, as the amotosalen can be present in solution as other salts or as the free base. As used in the methods described herein, removal of amotosalen means removal of the compound in any form, e.g., as the free base or as any salt, as measured by the assays described herein.

In some embodiments, the pathogen inactivation compound is a 4-primaryamino-substituted psoralen, which is a psoralen compound having an $NH_2$ group linked to the 4'-position of the psoralen by a hydrocarbon chain having a total length of 2 to 20 carbons, where 0 to 6 of those carbons are independently replaced by NH or O, and each point of replacement is separated from each other point of replacement by at least two carbons, and is separated from the psoralen by at least one carbon. 4'-primaryamino-substituted psoralens may have additional substitutions on the 4, 5', and 8 positions of the psoralen, said substitutions include, but are not limited to, the following groups: H and $(CH_2)\cdot CH_3$, where n=0-6. In some embodiments, the 4'-primaryamino-substituted psoralen comprises: a) a substituent $R_1$ on the 4' carbon atom, selected from the group comprising: $—(CH_2)_u—NH_2$, $—(CH_2)_w—R_2—(CH_2)_z—NH_2$, $—(CH_2)_w—R_2—(CH_2)_x—R_3—(CH_2)_z—NH_2$, and $—(CH_2)_w—R_2—(CH_2)_x—R_3—(CH_2)_y—R_4—(CH_2)_z—NH_2$; wherein $R_2$, $R_3$, and $R_4$ are independently selected from the group comprising O and NH, in which u is a whole number from 1 to 10, w is a whole number from 1 to 5, x is a whole number from 2 to 5, y is a whole number from 2 to 5, and z is a whole number from 2 to 6; and b) substituents $R_5$, $R_6$, and $R_7$ on the 4, 5', and 8 carbon atoms respectively, independently selected from the group comprising H and $(CH_2)_v CH_3$, where v is a whole number from 0 to 5; or a salt thereof.

In some embodiments, the pathogen inactivation compound is a 5-primaryamino-substituted psoralen, which is a psoralen compound having an $NH_2$ group linked to the 5'-position of the psoralen by a hydrocarbon chain having a total length of 1 to 20 carbons, where 0 to 6 of those carbons are independently replaced by NH or O, and each point of replacement is separated from each other point of replacement by at least two carbons, and is separated from the psoralen by at least one carbon. 5'-primaryamino-substituted psoralens may have additional substitutions on the 4, 4', and 8 positions of the psoralen, said substitutions include, but are not limited to, the following groups: H and $(CH_2)\cdot CH_3$, where n=0-6. In some embodiments, the 5'-primaryamino-substituted psoralen comprises: a) a substituent $R_1$ on the 5' carbon atom, selected from the group comprising: $—(CH_2)_u—NH_2$, $—(CH_2)_w—R_2—(CH_2)_z—NH_2$, $—(CH_2)_w—R_2—(CH_2)_x—R_3—(CH_2)_z—NH_2$, and $—(CH_2)_w—R_2—(CH_2)_x—R_3—(CH_2)_y—R_4—(CH_2)_z—NH_2$; wherein $R_2$, $R_3$, and $R_4$ are independently selected from the group comprising O and NH, and in which u is a whole number from 1 to 10, w is a whole number from 1 to 5, x is a whole number from 2 to 5, y is a whole number from 2 to 5, and z is a whole number from 2 to 6; and, b) substituents $R_5$, $R_6$, and $R_7$ on the 4, 4', and 8 carbon atoms respectively, independently selected from the group comprising H and $(CH_2)_v CH_3$, where v is a whole number from 0 to 5, where when $R_1$ is selected from the group comprising $—(CH_2)_u—NH_2$, $R_7$ is $(CH_2)_v CH_3$, and where when $R_5$, $R_6$, and $R_7$ are $(CH^2)_v CH_3$, u is a whole number from 3 to 10; or a salt thereof. Exemplary psoralen compounds are described, e.g., in U.S. Pat. No. 5,593,823.

In some embodiments, the biological fluid is in admixture with a pathogen inactivation compound (PIC) in a platelet additive solution (PAS). In some embodiments, the PIC is admixed with the PAS prior to admixing with the biological fluid. Platelet additive solutions are known in the art, for example, as described by Alhumaidan et al. and Ringwald et al. (Alhumaidan, H. and Sweeney, J., J Clin Apheresis, 27: 93-98 (2012); Ringwald et al., Transfusion Medicine Reviews, 20: 158-64 (2006)), which are hereby incorporated by reference in their entirety. In some embodiments, the platelet additive solution (PAS) comprises one or more of chloride, acetate, citrate, potassium, magnesium, phosphate, gluconate, glucose, and bicarbonate. In some embodiments, the platelet additive solution (PAS) is a PAS approved by a regulatory agency or accrediting organization generally accepted in the field.

In some embodiments, the methods further comprise agitating the biological fluid. In some embodiments of any of the methods of the disclosure, a total dose of ultraviolet light illuminating the biological fluid (e.g., emitted by the one or more light sources, emitted by a set of one or more light sources, emitted by an array of light sources) is about 0.5 J/cm$^2$ to about 50 J/cm$^2$, such as any of about 0.5 J/cm$^2$ to about 10 J/cm$^2$, about 0.5 J/cm$^2$ to about 15 J/cm$^2$, about 0.5 J/cm$^2$ to about 25 J/cm$^2$, about 1 J/cm$^2$ to about 10 J/cm$^2$, about 1 J/cm$^2$ to about 15 J/cm$^2$, about 1 J/cm$^2$ to about 25 J/cm$^2$, about 3 J/cm$^2$ to about 10 J/cm$^2$, about 3 J/cm$^2$ to about 15 J/cm$^2$, about 3 J/cm$^2$ to about 25 J/cm$^2$, about 5 J/cm$^2$ to about 10 J/cm$^2$, about 5 J/cm$^2$ to about 15 J/cm$^2$, about 5 J/cm$^2$ to about 25 J/cm$^2$, about 10 J/cm$^2$ to about 30 J/cm$^2$, about 10 J/cm$^2$ to about 20 J/cm$^2$, about 15 J/cm$^2$ to about 50 J/cm$^2$, about 15 J/cm$^2$ to about 35 J/cm$^2$, about 20 J/cm$^2$ to about 30 J/cm$^2$, about 25 J/cm$^2$ to about 50 J/cm$^2$, about 30 J/cm$^2$ to about 40 J/cm$^2$, or about 40 J/cm$^2$ to about 50 J/cm$^2$. In some embodiments, the total dose of ultraviolet light illuminating the biological fluid is about 0.5 J/cm$^2$ or more, such as about any of 1 J/cm$^2$ or more, 2 J/cm$^2$ or more, 3 J/cm$^2$ or more, 4 J/cm$^2$ or more, 5 J/cm$^2$ or more, 6 J/cm$^2$ or more, 7 J/cm$^2$ or more, 8 J/cm$^2$ or more, 9 J/ccm$^2$ or more, 15 J/cm$^2$ or more, 20 J/cm$^2$ or more, 25 J/cm$^2$ or more, 30 J/cm$^2$ or more, 35 J/cm$^2$ or more, 40 J/cm$^2$ or more, 45 J/cm$^2$ or more, or 50 J/cm$^2$ or more. In some embodiments, the total dose of ultraviolet light illuminating the biological fluid is less than about 50 J/cm$^2$, less than about 40 J/cm$^2$, less than about 30 J/cm$^2$, less than about 25 J/cm$^2$, less than about 20 J/cm$^2$, less than about 15 J/cm$^2$, or less than about 10 J/cm$^2$. In some embodiments, illuminating the biological fluid occurs for a duration and at an intensity sufficient to inactivate a pathogen in the biological fluid (e.g., if present in the biological fluid). For example, in some embodiments, illuminating the biological fluid occurs for a duration and at an intensity sufficient to provide a total dose (e.g., desired total dose, pre-determined total dose, aforementioned total dose) of ultraviolet light illuminating the biological fluid (e.g., any suitable combination of duration and intensity sufficient to provide the total dose of ultraviolet light). In some embodiments, the intensity is between 1 and 1000 mW/cm$^2$ (e.g., between 1 and 100 mW/cm$^2$). In some embodiments, the duration is between 1 second and 2 hours (e.g., between 1 minute and 60 minutes).

It should be understood that treatment of a biological fluid to inactivate pathogen(s) that may be present does not necessarily inactivate completely all pathogens that may be present, but substantially reduces the amount of pathogens to significantly reduce the risk arising from the presence of a pathogen (e.g., infection associated with administration of a biological fluid contaminated with a pathogen, transfusion associated disease from a blood product, transfusion transmitted infection from a blood product). The inactivation of a pathogen may be assayed by measuring the number of infective pathogens (e.g., viral particles, bacteria) in a certain volume, and the level of inactivation is typically represented in the log reduction in the infectivity of the pathogen, or log reduction in titer. Methods of assaying log reduction in titer, and measurements thereof to assess levels of pathogen inactivation are well known in the art. In some embodiments, the systems, devices and/or methods for treating are sufficient to inactivate at least 1 log (e.g., at least 2 logs, at least 3 logs, at least 4 logs, or more) of a pathogen in the biological fluid when present. In some embodiments, the biological fluid after illuminating is suitable for infusion into a subject without further processing to remove residual pathogen inactivation compound or photoproduct(s) thereof. In some embodiments, the systems, devices and/or methods for treating are sufficient to inactivate at least 1 log (e.g., at least 2 logs, at least 3 logs, at least 4 logs, or more) of a pathogen in the biological fluid when present, and the biological fluid comprises 10 μM or less of a pathogen inactivation compound after illuminating the biological fluid. In some embodiments, the systems, devices and/or methods for treating are sufficient to inactivate at least 1 log (e.g., at least 2 logs, at least 3 logs, at least 4 logs, or more) of a pathogen in the biological fluid when present, and the biological fluid comprises 7.5 μM or less of the pathogen inactivation compound after illuminating. In some embodiments, the systems, devices and/or methods for treating are sufficient to inactivate at least 1 log (e.g., at least 2 logs, at least 3 logs, at least 4 logs, or more) of a pathogen in the biological fluid when present, and the biological fluid comprises 5 μM or less (e.g., 4 μM or less, 3 μM or less, 2 μM or less, 1 μM or less, 0.5 μM or less) of the pathogen inactivation compound after illuminating. In some embodiments, a concentration of the pathogen inactivation compound in admixture with the biological fluid prior to illuminating is at least about 10 μM (e.g., at least about 30 μM, at least about 60 μM, at least at least about 90 μM, at least about 110 μM). In some embodiments, a concentration of the pathogen inactivation compound in admixture with the biological fluid prior to illuminating is about 15 μM to about 150 μM (e.g., about 30 μM to about 110 μM, about 60 μM to about 90 μM, about 75 μM). In some embodiments, a concentration of the pathogen inactivation compound in admixture with the biological fluid after illuminating is at least 3-fold less than the concentration of pathogen inactivation compound in admixture with the biological fluid prior to illuminating. In some embodiments, the biological fluid after illuminating maintains sufficient biological activity so that the biological fluid is suitable for infusion into a subject. In any of the aforementioned embodiments, the biological fluid may be a blood product (e.g., platelets, plasma).

In some aspects of the above device, the first controller includes an output port, and wherein the first controller is configured to communicate with an external computing device using the output port.

In some aspects of the above devices, isolating the plurality of non-safety critical components from the plurality of safety-critical components includes configuring the domain-specific interface language so as to minimize an impact to the plurality of safety critical components from one or more modifications to the non-safety critical components.

In some aspects of the above devices, the device further includes one or more treatment chambers configured to receive the biological fluid, and wherein each platform of the one or more platforms are configured to be positioned in a treatment chamber of the one of the one or more treatment chambers.

In some aspects of the above devices, the safety critical components further comprise one or more agitators, wherein each agitator is configured to agitate at least one of the one or more platforms.

In some aspects of the above devices, the safety critical components further comprise one or more sensors configured to detect light energy from the one or more light engines.

In some aspects of the above devices, the one or more light engines includes one or more arrays of light sources positioned to illuminate the biological fluid and wherein the one or more arrays of light sources are configured to emit light in an ultraviolet light spectrum.

In some aspects of the above devices, the one or more arrays of light sources each comprise a first light source channel configured to emit ultraviolet light with a first peak wavelength from about 315 nm to about 350 nm.

In some aspects of the above devices, the first light source channel comprises one or more light sources each of which emits light having a full-width half-maximum (FWHM) spectral bandwidth of less than 20 nanometers.

In some aspects of the above devices, the first light source channel comprises one or more light sources, and wherein the one or more light sources are light emitting diodes (LEDs).

In some aspects of the above devices, the one or more light engines further comprise one or more sensors configured to detect light energy from the one or more arrays of light sources.

In some aspects of the above devices, the one or more safety critical components includes computing hardware configured to perform one or more algorithms and configured to store information regarding the operation of the electronic device.

In some aspects of the above devices, the second controller is configured to turn one or more of the safety critical components on or off based on one or more operating conditions of the device.

In some aspects of the above devices, the one or more safety components are collectively configured to implement a hardware watchdog.

In some aspects of the above devices, the one or more safety components are collectively configured to implement a software watchdog.

In some aspects of the above devices, the one or more non-safety critical components includes a display configured to provide information to a user of the device and/or receive an input from the user of the device.

In some aspects of the above devices, for use in a method of treating a biological fluid including: providing a biological fluid in admixture with a photoactive pathogen inactivation compound, and illuminating the biological fluid with ultraviolet light with a first peak wavelength of from about 315 nm to about 350 nm emitted by a set of one or more first light sources, wherein: 1) each of the one or more first light sources emits light having a full-width half-maximum (FWHM) spectral bandwidth of less than 20 nanometers, or 2) each of the one or more first light sources is a light-emitting diode (LED), and wherein illuminating the biological fluid occurs for a duration and at an intensity sufficient to inactivate a pathogen in the biological fluid.

In some aspects of the above devices, the device further includes: a treatment interface, wherein the first controller is communicatively coupled to the plurality of non-safety critical components and the second controller is communicatively coupled to the plurality of safety critical components through the treatment interface; one or more processors; memory; and one or more programs, wherein the one or more programs are stored in the memory and configured to be executed by the one or more processors, the one or more programs including instructions for: in response to communicatively coupling the plurality of non-safety critical components to the treatment interface and communicatively coupling the plurality of safety-critical component to the treatment interface, detecting, with the controller, presences of the plurality of non-safety critical component and the plurality of safety-critical component in the electronic device; transmitting first messages between the first controller and the non-safety critical component through the treatment interface; transmitting second messages between the second controller and the safety-critical component through the treatment interface, wherein the first and second messages are based on the domain-specific interface language; determining states of the non-safety critical components based on the first messages; and determining states of the safety critical components based on the second messages.

In some aspects of the above devices, a non-safety critical component or a safety-critical component is in a first state, and the one or more programs further includes instructions for: changing the state of the non-safety critical component or the safety-critical component from the first state to a second state; in response to the changing the state, sending, from of the non-safety critical component or the safety-critical component to the first controller or the second controller through the treatment interface, a second message; receiving, at the first controller or the second controller, the second message; and in response to receiving the second message, determining a second state of the treatment component.

In some aspects of the above devices, the one or more programs further includes instructions for providing power to the electronic device; and the presences of the plurality of non-safety critical component and the plurality of safety-critical component are detected further in response to the providing of power to the electronic device.

In some aspects of the above devices, the one or more programs further includes instructions for: in response to the providing of power to the electronic device, assigning local network addresses and ports to the plurality of non-safety critical components and the plurality of safety-critical components, wherein the local network addresses or ports are based on the domain-specific device interface language.

In some aspects of the above devices, the one or more messages written in the domain-specific interface language can be transmitted using TCP/IP.

In another aspect, a method of treating a biological fluid includes: providing a biological fluid in admixture with a photoactive pathogen inactivation compound, and illuminating the biological fluid with any of the above devices, for a duration and at an intensity sufficient to inactivate a pathogen in the biological fluid.

In another aspect, a method of operating an electronic device for treating a biological fluid, the electronic device including a controller, a non-safety critical component, a safety-critical component, and a treatment interface, the method includes: coupling the non-safety critical component or the safety-critical component to the treatment interface; in response to the coupling of the non-safety critical component or the safety-critical component to the treatment interface, detecting, with the controller, a presence of the non-safety critical component or the safety-critical component in the electronic device; transmitting a message between the controller and the non-safety critical component or the safety-critical component through the treatment interface, the message based on a domain-specific interface language; and determining a state of the non-safety critical component or the safety-critical component based on the message.

In some aspects of the above method, the electronic device further comprises a second controller coupled to the treatment interface and the safety-critical component is coupled to the treatment interface, the method further includes: coupling the non-safety critical component to the treatment interface; and isolating the non-safety critical component from the safety-critical component, wherein the isolation comprises configuring the domain-specific interface language so as to minimize an impact to the safety-critical component from one or more modifications to the non-safety critical component.

In some aspects of the above methods, the non-safety critical component or the safety-critical component is in a first state, the method further includes: changing the state of the non-safety critical component or the safety-critical component from the first state to a second state; in response to the changing the state, sending, from of the non-safety critical component or the safety-critical component to the controller through the treatment interface, a second message; receiving, at the controller, the second message; and in response to receiving the second message, determining a second state of the treatment component.

In some aspects of the above methods, the safety-critical component is one of a platform, light engine, agitator, and a safety component, wherein the one or more safety components are configured to monitor the operation of the safety-critical components.

In some aspects of the above methods, the method further includes isolating the treatment interface from an external network using the domain-specific interface language.

In some aspects of the above methods, the method further includes providing power to the electronic device; the presence of the treatment component is detected further in response to the providing of power to the electronic device.

In some aspects of the above methods, the method further includes in response to the providing of power to the electronic device, assigning a local network address or a port to the non-safety critical component or the safety-critical component, wherein the local network address or port is based on the domain-specific interface language.

In some aspects of the above methods, one or more messages written in the domain-specific interface language can be transmitted using TCP/IP.

In another aspect, an electronic device for treating a biological fluid includes: a controller, a non-safety critical component, a safety-critical component, a treatment interface, one or more processors; memory; and one or more programs, wherein the one or more programs are stored in the memory and configured to be executed by the one or more processors, the one or more programs including instructions for: in response to a coupling of the non-safety critical component or the safety-critical component to the treatment interface, detecting, with the controller, a presence of the non-safety critical component or the safety-critical component in the electronic device; transmitting a message between the controller and the non-safety critical component or the safety-critical component to the treatment interface through the treatment interface, the message based on a domain-specific interface language; and determining a state of the non-safety critical component or the safety-critical component based on the message.

In another aspect, a non-transitory computer readable storage medium storing one or more programs, the one or more programs comprising instructions, which when executed by an electronic device with one or more processors and memory, cause the device to: couple the non-safety critical component or the safety-critical component to the treatment interface; in response to the coupling of the non-safety critical component or the safety-critical component to the treatment interface, detect, with the controller, a presence of the non-safety critical component or the safety-critical component in the electronic device; transmit a message between the controller and the non-safety critical component or the safety-critical component to the treatment interface through the treatment interface, the message based on a domain-specific interface language; and determine a state of the non-safety critical component or the safety-critical component based on the message.

In some embodiments, the electronic device includes a plurality of non-safety critical components, a first controller communicatively coupled to the plurality of non-safety critical components, a plurality of safety critical components, and a second controller communicatively coupled to the plurality of safety critical components. In some embodiments, the electronic device includes a treatment interface.

In some embodiments, an electronic device for treating a biological fluid, includes: a plurality of non-safety critical components; a first controller communicatively coupled to the plurality of non-safety critical components and configured to operate the plurality of non-safety critical components; a plurality of safety critical components, wherein the safety critical components comprise: one or more platforms, wherein each platform of the one or more platforms is configured to carry one or more biological fluids; one or more light engines, wherein each light engine is configured to illuminate the biological fluid; and one or more safety components; wherein the one or more safety components are configured to monitor the operation of the safety critical components; and a second controller communicatively coupled to the plurality of safety critical components and communicatively coupled to the first controller, wherein the second controller is configured to coordinate one or more operations involving the plurality of safety critical components; wherein the first controller and the second controller communicate with one another using a domain-specific interface language configured to isolate the plurality of non-safety critical components from the plurality of safety-critical components.

In some embodiments, the first controller includes an output port, and wherein the first controller is configured to communicate with an external computing device using the output port.

In some embodiments, isolating the plurality of non-safety critical components from the plurality of safety-critical components includes configuring the domain-specific interface language so as to minimize an impact to the plurality of safety critical components from one or more modifications to the non-safety critical components.

In some embodiments, the device further includes one or more treatment chambers configured to receive the biological fluid, and wherein each platform of the one or more platforms are configured to be positioned in a treatment chamber of the one of the one or more treatment chambers.

In some embodiments, the safety critical components further comprise one or more agitators, wherein each agitator is configured to agitate at least one of the one or more platforms.

In some embodiments, the safety critical components further comprise one or more sensors configured to detect light energy from the one or more light engines.

In some embodiments, the one or more light engines includes one or more arrays of light sources positioned to illuminate the biological fluid and wherein the one or more arrays of light sources are configured to emit light in an ultraviolet light spectrum.

In some embodiments, the one or more arrays of light sources each comprise a first light source channel configured to emit ultraviolet light with a first peak wavelength from about 315 nm to about 350 nm.

In some embodiments, the first light source channel comprises one or more light sources each of which emits light having a full-width half-maximum (FWHM) spectral bandwidth of less than 20 nanometers.

In some embodiments, the first light source channel comprises one or more light sources, and wherein the one or more light sources are light emitting diodes (LEDs).

In some embodiments, the one or more light engines further comprise one or more sensors configured to detect light energy from the one or more arrays of light sources.

In some embodiments, the one or more safety critical components includes computing hardware configured to perform one or more algorithms and configured to store information regarding the operation of the electronic device.

In some embodiments, the second controller is configured to turn one or more of the safety critical components on or off based on one or more operating conditions of the device.

In some embodiments, the one or more safety components are collectively configured to implement a hardware watchdog.

In some embodiments, the one or more safety components are collectively configured to implement a software watchdog.

In some embodiments, the one or more non-safety critical components includes a display configured to provide information to a user of the device and/or receive an input from the user of the device.

In some embodiments, for use in a method of treating a biological fluid including: providing a biological fluid in admixture with a photoactive pathogen inactivation compound, and illuminating the biological fluid with ultraviolet light with a first peak wavelength of from about 315 nm to about 350 nm emitted by a set of one or more first light sources, wherein: 1) each of the one or more first light sources emits light having a full-width half-maximum (FWHM) spectral bandwidth of less than 20 nanometers, or 2) each of the one or more first light sources is a light-emitting diode (LED), and wherein illuminating the biological fluid occurs for a duration and at an intensity sufficient to inactivate a pathogen in the biological fluid.

In some embodiments, the device further includes: a treatment interface, wherein the first controller is communicatively coupled to the plurality of non-safety critical components and the second controller is communicatively coupled to the plurality of safety critical components through the treatment interface; one or more processors; memory; and one or more programs, wherein the one or more programs are stored in the memory and configured to be executed by the one or more processors, the one or more programs including instructions for: in response to communicatively coupling the plurality of non-safety critical components to the treatment interface and communicatively coupling the plurality of safety-critical component to the treatment interface, detecting, with the controller, presences of the plurality of non-safety critical component and the plurality of safety-critical component in the electronic device; transmitting first messages between the first controller and the non-safety critical component through the treatment interface; transmitting second messages between the second controller and the safety-critical component through the treatment interface, wherein the first and second messages are based on the domain-specific interface language; determining states of the non-safety critical components based on the first messages; and determining states of the safety critical components based on the second messages.

In some embodiments, a non-safety critical component or a safety-critical component is in a first state, and the one or more programs further includes instructions for: changing the state of the non-safety critical component or the safety-critical component from the first state to a second state; in response to the changing the state, sending, from of the non-safety critical component or the safety-critical component to the first controller or the second controller through the treatment interface, a second message; receiving, at the first controller or the second controller, the second message; and in response to receiving the second message, determining a second state of the treatment component.

In some embodiments, the one or more programs further includes instructions for providing power to the electronic device; and the presences of the plurality of non-safety critical component and the plurality of safety-critical component are detected further in response to the providing of power to the electronic device.

In some embodiments, the one or more programs further includes instructions for: in response to the providing of power to the electronic device, assigning local network addresses and ports to the plurality of non-safety critical components and the plurality of safety-critical components, wherein the local network addresses or ports are based on the domain-specific interface language.

In some embodiments, the one or more messages written in the domain-specific interface language can be transmitted using TCP/IP.

In some embodiments, a method of treating a biological fluid includes: providing a biological fluid in admixture with a photoactive pathogen inactivation compound, and illuminating the biological fluid with any of the above devices, for a duration and at an intensity sufficient to inactivate a pathogen in the biological fluid.

In some embodiments, a method of operating an electronic device for treating a biological fluid, the electronic device including a controller, a non-safety critical component, a safety-critical component, and a treatment interface, the method includes: coupling the non-safety critical component or the safety-critical component to the treatment interface; in response to the coupling of the non-safety critical component or the safety-critical component to the treatment interface, detecting, with the controller, a presence of the non-safety critical component or the safety-critical component in the electronic device; transmitting a message between the controller and the non-safety critical component or the safety-critical component through the treatment interface, the message based on a domain-specific interface language; and determining a state of the non-safety critical component or the safety-critical component based on the message.

In some embodiments, the electronic device further comprises a second controller coupled to the treatment interface and the safety-critical component is coupled to the treatment interface, the method further includes: coupling the non-safety critical component to the treatment interface; and isolating the non-safety critical component from the safety-critical component, wherein the isolation comprises configuring the domain-specific interface language so as to minimize an impact to the safety-critical component from one or more modifications to the non-safety critical component.

In some embodiments, the non-safety critical component or the safety-critical component is in a first state, the method further includes: changing the state of the non-safety critical component or the safety-critical component from the first state to a second state; in response to the changing the state, sending, from of the non-safety critical component or the safety-critical component to the controller through the treatment interface, a second message; receiving, at the controller, the second message; and in response to receiving the second message, determining a second state of the treatment component.

In some embodiments, the safety-critical component is one of a platform, light engine, agitator, and a safety component, wherein the one or more safety components are configured to monitor the operation of the safety-critical components.

In some embodiments, the method further includes isolating the treatment interface from an external network using the domain-specific interface language.

In some embodiments, the method further includes providing power to the electronic device; the presence of the treatment component is detected further in response to the providing of power to the electronic device.

In some embodiments, the method further includes in response to the providing of power to the electronic device, assigning a local network address or a port to the non-safety critical component or the safety-critical component, wherein the local network address or port is based on the domain-specific interface language.

In some embodiments, one or more messages written in the domain-specific interface language can be transmitted using TCP/IP.

In some embodiments, an electronic device for treating a biological fluid includes: a controller, a non-safety critical component, a safety-critical component, a treatment interface, one or more processors; memory; and one or more programs, wherein the one or more programs are stored in the memory and configured to be executed by the one or more processors, the one or more programs including instructions for: in response to a coupling of the non-safety critical component or the safety-critical component to the treatment interface, detecting, with the controller, a presence of the non-safety critical component or the safety-critical component in the electronic device; transmitting a message between the controller and the non-safety critical component or the safety-critical component to the treatment interface through the treatment interface, the message based on a domain-specific interface language; and determining a state of the non-safety critical component or the safety-critical component based on the message.

In some embodiments, a non-transitory computer readable storage medium storing one or more programs, the one or more programs comprising instructions, which when executed by an electronic device with one or more processors and memory, cause the device to: couple the non-safety critical component or the safety-critical component to the treatment interface; in response to the coupling of the non-safety critical component or the safety-critical component to the treatment interface, detect, with the controller, a presence of the non-safety critical component or the safety-critical component in the electronic device; transmit a message between the controller and the non-safety critical component or the safety-critical component to the treatment interface through the treatment interface, the message based on a domain-specific interface language; and determine a state of the non-safety critical component or the safety-critical component based on the message.

Variations of the embodiments provided herein may become apparent to those working in the art upon reading the foregoing description. It is expected that skilled artisans will be able to employ such variations as appropriate, and the practice of the compositions, methods, and kits described herein otherwise than as specifically described herein. Accordingly, the systems and methods described herein include all modifications and equivalents of the subject matter recited in the claims appended hereto as permitted by applicable law. Moreover, any combination of the above-described elements in all possible variations thereof is encompassed by the description unless otherwise indicated herein or otherwise clearly contradicted by context. The following is a list of particular embodiments of the present disclosure. The list is exemplary is it not intended to be limiting of the disclosure provided herein.

Embodiment 1: An electronic device, wherein the electronic device includes a plurality of components collectively configured to treat one or more biological fluids, the device comprising:
  a first group of components, wherein the first group of components includes one or more components configured to receive one or more inputs from a user of the device;
  a first controller communicatively coupled to the first group of components and configured to operate the first group of components using one or more commands formatted using a first communications protocol;
  a second group of components, wherein the second group of components comprise:
    one or more platforms, wherein each platform of the one or more platforms is configured to carry a biological fluid of the one or more biological fluids;
    one or more light engines, wherein each light engine is configured to illuminate a biological fluid of the one or more biological fluids; and
  a second controller communicatively coupled to the second group of components and communicatively coupled to the first controller, wherein the second controller is configured to coordinate one or more operations involving the second group of components;
    wherein the second controller communicates with the first controller and the second group of components using a second communications protocol, wherein the second communications protocol is configured such that the second group of components operate in response to one or commands from the second controller using the second communications protocol.

Embodiment 2: The device of embodiment 1, wherein the second group of components are configured to operate only in response to one or more commands transmitted from the second controller using the second communications protocol.

Embodiment 3: The device of embodiment 1 or embodiment 2, wherein a message transmitted in the second communications protocol includes information about the component that generated the message.

Embodiment 4: The device of any one of embodiments 1-3, wherein the first group of components include one or more components configured to allow an external user to interface with the device.

Embodiment 5: The device of any one of embodiments 1-4, wherein the first group of components includes a display configured to provide visual cues to the user of the device and configured to accept one or more inputs.

Embodiment 6: The device of embodiment 5, wherein the display is a touchscreen display configured to accept one or more touch inputs from the user of the device.

Embodiment 7: The device of any one of embodiments 1-6, wherein the first group of components includes a scanner configured to collect identifying information associated with a biological fluid being treated.

Embodiment 8: The device of any one of embodiments 1-7, wherein the second group of components further includes one or more agitators, wherein each agitator is configured to agitate a biological fluid of the one or more biological fluids so as to distribute the biological fluid within a container that is disposed on a platform of the one or more platforms of the device.

Embodiment 9: The device of any one of embodiments 1-8, comprising one or more treatment chambers configured to receive a biological fluid of the one or more biological fluids, and wherein each platform of the one or more platforms are configured to be positioned in a treatment chamber of the one or more treatment chambers.

Embodiment 10: The device of any one of embodiments 1-9, wherein the second group of components further comprise one or more sensors configured to detect an operating condition of the device or a property of the biological fluid.

Embodiment 11: The device of any of embodiments 1-10, wherein the one or more light engines includes one or more arrays of light sources positioned to illuminate the biological fluid and wherein the one or more arrays of light sources are configured to emit light in an ultraviolet light spectrum.

Embodiment 12: The device of embodiment 11, wherein the one or more arrays of light sources each comprise a first light source channel configured to emit ultraviolet light with a first peak wavelength from about 315 nm to about 350 nm.

Embodiment 13: The device of embodiment 11 or embodiment 12, wherein the one or more arrays of light sources comprise one or more light sources each of which emits light having a full-width half-maximum (FWHM) spectral bandwidth of less than 20 nanometers.

Embodiment 14: The device of any one of embodiments 11-13, wherein the one or more arrays of light sources comprise one or more light sources, and wherein the one or more light sources are light emitting diodes (LEDs).

Embodiment 15: The device of any one of embodiments 1-14, wherein the one or more light engines further comprise one or more sensors configured to detect light energy from the one or more arrays of light sources.

Embodiment 16: The device of any one of embodiments 10-15, wherein the second controller is configured to turn one or more of the second group of components on or off based on one or more signals transmitted by the one or more sensors.

Embodiment 17: The device of any one of embodiments 9-16, comprising:
a first treatment chamber configured to receive a first biological fluid;
a second treatment chamber configured to receive a second biological fluid:
a first platform configured to carry the first biological fluid and to be positioned in the first treatment chamber;
a second platform configured to carry the second biological fluid and to be positioned in the second treatment chamber; and
a first array of light sources positioned to illuminate the first biological fluid in the first treatment chamber and a second array of light sources positioned to illuminate the second biological fluid in the second treatment chamber.

Embodiment 18: The device of any one of embodiments 1-17, wherein the device is configured to receive one or more inputs from a user of the device, and the device is configured to:
transmit one or more commands using the first communications protocol to the first controller, wherein the one or more commands are configured to initiate a treatment process on a biological fluid of the one or more biological fluids;
at the first controller, convert the one or more commands in the first communications protocol into one or more commands in the second communications protocol and transmit the one or more commands in the second communications protocol to the second controller; and
at the second controller, convert the received one or more commands in the second communications protocol into one or more commands to control one or more components of the second group of components and transmit the one or more commands to the one or more components of the second group of components, wherein the one or more commands to control the one or more components of the second group of components are configured to cause the device to treat a biological fluid of the one or more biological fluids.

Embodiment 19: The device of any one of embodiments 1-18, wherein treating the one or more biological fluids comprises illuminating the biological fluids for a duration and at an intensity sufficient to inactivate a pathogen in the biological fluids.

Embodiment 20: A method for treating one or more biological fluids at an electronic device, the method comprising:
receiving one or more inputs from a user of the device;
transmitting one or more commands using a first communications protocol to a first controller of the device, wherein the one or more commands are configured to initiate a treatment process on biological fluid of the one or more biological fluids, and wherein the first controller is communicatively coupled to a first group of components device and configured to operate the first group of components using one or more commands formatted using the first communications protocol;
at the first controller, converting the one or more commands in the first communications protocol into one or more commands in a second communications protocol and transmitting the one or more commands in the second communications protocol to a second controller of the device; and
at the second controller, converting the received one or more commands in the second communications protocol into one or more commands to control one or more components of a second group of components of the device and transmitting the one or more commands to one or more components of the second group of components, wherein the one or more commands to control the one or more components of the second group of components are configured to cause the device to treat a biological fluid of the one or more biological fluids.

Embodiment 21: The method of embodiment 20, wherein the second group of components comprise:
- one or more platforms, wherein each platform of the one or more platforms is configured to carry a biological fluid of the one or more biological fluids; and
- one or more light engines, wherein each light engine is configured to illuminate a biological fluid of the one or more biological fluids.

Embodiment 22: The method of embodiment 20 or embodiment 21, wherein the second group of components are configured to operate only in response to one or more commands transmitted from the second controller using the second communications protocol.

Embodiment 23: The method of any one of embodiments 20-22, wherein a message transmitted in the second communications protocol includes information about the component that generated the message.

Embodiment 24: The method of any one of embodiments 20-23, wherein the first group of components include one or more components configured to allow an external user to interface with the device.

Embodiment 25: The method of any one of embodiments 20-24, wherein the first group of components includes a display configured to provide visual cues to the user of the device and configured to accept one or more inputs.

Embodiment 26: The method of embodiment 25, wherein the display is a touchscreen display configured to accept one or more touch inputs from the user of the device.

Embodiment 27: The method of any one of embodiments 20-26, wherein the first group of components includes a scanner configured to collect identifying information associated with a biological fluid being treated.

Embodiment 28: The method of any one of embodiments 20-27, wherein the second group of components further includes one or more agitators, wherein each agitator is configured to agitate a biological fluid of the one or more biological fluids so as to distribute the biological fluid within a container that is disposed on a platform of the one or more platforms of the device.

Embodiment 29: The method of any one of embodiments 20-28, wherein the electronic device comprises one or more treatment chambers configured to receive a biological fluid of the one or more biological fluids, and wherein each platform of the one or more platforms are configured to be positioned in a treatment chamber of the one or more treatment chambers.

Embodiment 30: The method of any one of embodiments 20-29, wherein the second group of components further comprise one or more sensors configured to an operating condition of the device or a property of the biological fluid.

Embodiment 31: The method of any of embodiments 20-30, wherein the one or more light engines includes one or more arrays of light sources positioned to illuminate a biological fluid of the one or more biological fluids and wherein the one or more arrays of light sources are configured to emit light in an ultraviolet light spectrum.

Embodiment 32: The method of embodiment 31, wherein the one or more arrays of light sources each comprise a first light source channel configured to emit ultraviolet light with a first peak wavelength from about 315 nm to about 350 nm.

Embodiment 33: The method of embodiment 31 or embodiment 32, wherein the one or more arrays of light sources comprise one or more light sources each of which emits light having a full-width half-maximum (FWHM) spectral bandwidth of less than 20 nanometers.

Embodiment 34: The method of any one of embodiments 31-33, wherein the one or more arrays of light sources comprise one or more light sources, and wherein the one or more light sources are light emitting diodes (LEDs).

Embodiment 35: The method of any one of embodiments 20-34, wherein the one or more light engines further comprise one or more sensors configured to detect light energy from the one or more arrays of light sources.

Embodiment 36: The method of any one of embodiments 30-35, wherein the second controller is configured to turn one or more of the second group of components on or off based on one or more signals transmitted by the one or more sensors.

Embodiment 37: The method of any one of embodiments 20-36, wherein the electronic device comprises:
- a first treatment chamber configured to receive a first biological fluid;
- a second treatment chamber configured to receive a second biological fluid:
- a first platform configured to carry the first biological fluid and to be positioned in the first treatment chamber;
- a second platform configured to carry the second biological fluid and to be positioned in the second treatment chamber; and
- a first array of light sources positioned to illuminate the first biological fluid in the first treatment chamber and a second array of light sources positioned to illuminate the second biological fluid in the second treatment chamber.

Embodiment 38: The method of any one of embodiments 20-37, wherein treating the one or more biological fluids comprises illuminating the biological fluids for a duration and at an intensity sufficient to inactivate a pathogen in the biological fluids.

Embodiment 39: A computer readable storage medium storing one or more programs, the one or more programs comprising instructions, which when executed by an electronic device configured to treat one or more biological fluids, cause the device to:
- receive one or more inputs from a user of the device;
- transmit one or more commands using a first communications protocol to a first controller of the device, wherein the one or more commands are configured to initiate a treatment process on a biological fluid of the one or more biological fluids, and wherein the first controller is communicatively coupled to a first group of components device and configured to operate the first group of components using one or more commands formatted using the first communications protocol;
- at the first controller, convert the one or more commands in the first communications protocol into one or more commands in a second communications protocol and transmitting the one or more commands in the second communications protocol to a second controller of the device; and
- at the second controller, convert the received one or more commands in the second communications protocol into one or more commands to control one or more components of a second group of components of the device and transmitting the one or more commands to one or more components of the second group of components, wherein the one or more commands to control the one or more components of the second group of components are configured to cause the device to treat a biological fluid of the one or more biological fluids.

Embodiment 40: The computer readable storage medium of embodiment 39, wherein the second group of components comprise:

one or more platforms, wherein each platform of the one or more platforms is configured to carry a biological fluid of the one or more biological fluids; and one or more light engines, wherein each light engine is configured to illuminate a biological fluid of the one or more biological fluids;

Embodiment 41: The computer readable storage medium of embodiment 39 or embodiment 40, wherein the second group of components are configured to operate only in response to one or more commands transmitted from the second controller using the second communications protocol.

Embodiment 42: The computer readable storage medium of any one of embodiments 39-41, wherein a message transmitted in the second communications protocol includes information about the component that generated the message.

Embodiment 43: The computer readable storage medium of any one of embodiments 39-42, wherein the first group of components include one or more components configured to allow an external user to interface with the device.

Embodiment 44: The computer readable storage medium of any one of embodiments 39-43, wherein the first group of components includes a display configured to provide visual cues to the user of the device and configured to accept one or more inputs.

Embodiment 45: The computer readable storage medium of embodiment 44, wherein the display is a touchscreen display configured to accept one or more touch inputs from the user of the device.

Embodiment 46: The computer readable storage medium of any one of embodiments 39-45, wherein the first group of components includes a scanner configured to collect identifying information associated with a biological fluid being treated.

Embodiment 47: The computer readable storage medium of any one of embodiments 39-46, wherein the second group of components further includes one or more agitators, wherein each agitator is configured to agitate a biological fluid of the one or more biological fluids so as to distribute the biological fluid within a container that is disposed on a platform of the one or more platforms of the device.

Embodiment 48: The computer readable storage medium of any one of embodiments 39-47, wherein the electronic device comprises one or more treatment chambers configured to receive a biological fluid of the one or more biological fluids, and wherein each platform of the one or more platforms are configured to be positioned in a treatment chamber of the one or more treatment chambers.

Embodiment 49: The computer readable storage medium of any one of embodiments 39-48, wherein the second group of components further comprise one or more sensors configured to detect an operating condition of the device or a property of the biological fluid.

Embodiment 50: The computer readable storage medium of any of embodiments 39-49, wherein the one or more light engines includes one or more arrays of light sources positioned to illuminate a biological fluid of the one or more biological fluids and wherein the one or more arrays of light sources are configured to emit light in an ultraviolet light spectrum.

Embodiment 51: The computer readable storage medium of embodiment 50, wherein the one or more arrays of light sources each comprise a first light source channel configured to emit ultraviolet light with a first peak wavelength from about 315 nm to about 350 nm.

Embodiment 52: The computer readable storage medium of embodiment 50 or embodiment 51, wherein the one or more arrays of light sources comprise one or more light sources each of which emits light having a full-width half-maximum (FWHM) spectral bandwidth of less than 20 nanometers.

Embodiment 53: The computer readable storage medium of any one of embodiments 50-52, wherein the one or more arrays of light sources comprise one or more light sources, and wherein the one or more light sources are light emitting diodes (LEDs).

Embodiment 54: The computer readable storage medium of any one of embodiments 39-53, wherein the one or more light engines further comprise one or more sensors configured to detect light energy from the one or more arrays of light sources.

Embodiment 55: The computer readable storage medium of any one of embodiments 49-54, wherein the second controller is configured to turn one or more of the second group of components on or off based on one or more signals transmitted by the one or more sensors.

Embodiment 56: The computer readable storage medium of any one of embodiments 39-55, wherein the electronic device comprises:
  a first treatment chamber configured to receive a first biological fluid;
  a second treatment chamber configured to receive a second biological fluid:
  a first platform configured to carry the first biological fluid and to be positioned in the first treatment chamber;
  a second platform configured to carry the second biological fluid and to be positioned in the second treatment chamber; and
  a first array of light sources positioned to illuminate the first biological fluid in the first treatment chamber and a second array of light sources positioned to illuminate the second biological fluid in the second treatment chamber.

Embodiment 57: The computer readable storage medium of any one of embodiments 39-56, wherein treating the one or more biological fluids comprises illuminating the biological fluids for a duration and at an intensity sufficient to inactivate a pathogen in the biological fluid.

The foregoing description, for purpose of explanation, has made reference to specific embodiments. However, the illustrative discussions above are not intended to be exhaustive or to limit the disclosure to the precise forms disclosed. Many modifications and variations are possible in view of the above teachings. The embodiments were chosen and described in order to best explain the principles of the techniques and their practical applications. Others skilled in the art are thereby enabled to best utilize the techniques and various embodiments, with various modifications, that are suited to the particular use contemplated.

Although the disclosure and examples have been fully described with reference to the accompanying figures, it is to be noted that various changes and modifications will become apparent to those skilled in the art. Such changes and modifications are to be understood as being included within the scope of the disclosure and examples as defined by the claims.

What is claimed is:

1. A method for treating one or more biological fluids at an electronic device, the method comprising:
  receiving one or more inputs from a user of the electronic device;

transmitting one or more commands using a first communications protocol to a first controller of the electronic device, wherein the one or more commands are configured to initiate a treatment process on a biological fluid of the one or more biological fluids, and wherein the first controller is communicatively coupled to a first group of components of the electronic device and configured to operate the first group of components using one or more commands formatted using the first communications protocol;

at the first controller, converting the one or more commands in the first communications protocol into one or more commands in a second communications protocol and transmitting the one or more commands in the second communications protocol to a second controller of the electronic device; and at the second controller, converting the received one or more commands in the second communications protocol into one or more commands to control one or more components of a second group of components of the electronic device and transmitting the one or more commands to one or more components of the second group of components, wherein the one or more commands to control the one or more components of the second group of components are configured to cause the electronic device to treat a biological fluid of the one or more biological fluids, wherein the second group of components comprises: one or more light engines, wherein each light engine is configured to illuminate a biological fluid of the one or more biological fluids.

2. The method of claim 1, wherein the second group of components is configured to operate only in response to one or more commands transmitted from the second controller using the second communications protocol.

3. The method of claim 1, wherein a message transmitted in the second communications protocol includes information about the component that generated the message.

4. The method of claim 1, wherein the first group of components includes one or more components configured to allow an external user to interface with the electronic device.

5. The method of claim 1, wherein the first group of components includes a display configured to provide visual cues to the user of the electronic device and configured to accept one or more inputs.

6. The method of claim 5, wherein the display is a touchscreen display configured to accept one or more touch inputs from the user of the electronic device.

7. The method of claim 1, wherein the first group of components includes a scanner configured to collect identifying information associated with a biological fluid being treated.

8. The method of claim 1, wherein the second group of components comprises:

one or more platforms, wherein each platform of the one or more platforms is configured to carry a biological fluid of the one or more biological fluids.

9. The method of claim 8, wherein the second group of components comprises:

one or more agitators, wherein each agitator is configured to agitate a biological fluid of the one or more biological fluids so as to distribute the biological fluid within a container that is disposed on a platform of the one or more platforms of the device.

10. The method of claim 8, wherein the electronic device comprises:

one or more treatment chambers configured to receive a biological fluid of the one or more biological fluids, and wherein each platform of the one or more platforms are configured to be positioned in a treatment chamber of the one or more treatment chambers.

11. The method of claim 8, wherein the one or more light engines includes one or more arrays of light sources positioned to illuminate a biological fluid of the one or more biological fluids and wherein the one or more arrays of light sources are configured to emit light in an ultraviolet light spectrum.

12. The method of claim 11, wherein the one or more arrays of light sources each comprise a first light source channel configured to emit ultraviolet light with a first peak wavelength from about 315 nm to about 350 nm.

13. The method of claim 11, wherein the one or more arrays of light sources comprise one or more light sources each of which emits light having a full-width half-maximum (FWHM) spectral bandwidth of less than 20 nanometers.

14. The method of claim 13, wherein the one or more arrays of light sources comprise one or more light sources, and wherein the one or more light sources are light emitting diodes (LEDs).

15. The method of claim 13, wherein the one or more light engines further comprise one or more sensors configured to detect light energy from the one or more arrays of light sources.

16. The method of claim 1, wherein the second group of components comprises:

one or more sensors configured to sense an operating condition of the electronic device or a property of a biological fluid of the one or more biological fluids.

17. The method of claim 16, wherein the second controller is configured to turn one or more of the second group of components on or off based on one or more signals transmitted by the one or more sensors.

18. The method of claim 1, wherein the electronic device comprises:

a first treatment chamber configured to receive a first biological fluid;

a second treatment chamber configured to receive a second biological fluid:

a first platform configured to carry the first biological fluid and to be positioned in the first treatment chamber;

a second platform configured to carry the second biological fluid and to be positioned in the second treatment chamber; and a first array of light sources positioned to illuminate the first biological fluid in the first treatment chamber and a second array of light sources positioned to illuminate the second biological fluid in the second treatment chamber.

19. The method of claim 1, comprising:

treating the one or more biological fluids comprising illuminating the one or more biological fluids for a duration and at an intensity sufficient to inactivate a pathogen in the one or more biological fluids.

20. A computer readable storage medium storing one or more programs, the one or more programs comprising instructions, which when executed by an electronic device configured to treat one or more biological fluids, cause the electronic device to:

receive one or more inputs from a user of the electronic device;

transmit one or more commands using a first communications protocol to a first controller of the electronic device, wherein the one or more commands are configured to initiate a treatment process on a biological fluid of the one or more biological fluids, and wherein the first controller is communicatively coupled to a first group of components of the electronic device and configured to operate the first group of components using one or more commands formatted using the first communications protocol;

at the first controller, convert the one or more commands in the first communications protocol into one or more commands in a second communications protocol and transmitting the one or more commands in the second communications protocol to a second controller of the electronic device; and at the second controller, convert the received one or more commands in the second communications protocol into one or more commands to control one or more components of a second group of components of the electronic device and transmitting the one or more commands to one or more components of the second group of components, wherein the one or more commands to control the one or more components of the second group of components are configured to cause the electronic device to treat a biological fluid of the one or more biological fluids.

\* \* \* \* \*